US009096868B2

(12) United States Patent
Deng et al.

(10) Patent No.: US 9,096,868 B2
(45) Date of Patent: *Aug. 4, 2015

(54) POLYNUCLEOTIDES ALLOWING THE EXPRESSION AND SECRETION OF RECOMBINANT PSEUDO-VIRUS CONTAINING FOREIGN EPITOPES, THEIR PRODUCTION, AND USE

(75) Inventors: Qiang Deng, Shanghai (CN); Marie-Louise Michel, Paris (FR)

(73) Assignees: INSTITUT PASTEUR, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 564 days.

This patent is subject to a terminal disclaimer.

(21) Appl. No.: 12/678,046

(22) PCT Filed: Sep. 12, 2008

(86) PCT No.: PCT/EP2008/062208
§ 371 (c)(1), (2), (4) Date: Mar. 12, 2010

(87) PCT Pub. No.: WO2009/034182
PCT Pub. Date: Mar. 19, 2009

(65) Prior Publication Data
US 2011/0142878 A1 Jun. 16, 2011

Related U.S. Application Data

(60) Provisional application No. 60/960,091, filed on Sep. 14, 2007, provisional application No. 61/136,125, filed on Aug. 13, 2008, provisional application No. 61/136,154, filed on Aug. 14, 2008.

(51) Int. Cl.
*C12N 15/86* (2006.01)
*C07K 14/005* (2006.01)
*A61K 39/00* (2006.01)

(52) U.S. Cl.
CPC .............. *C12N 15/86* (2013.01); *C07K 14/005* (2013.01); *A61K 2039/57* (2013.01); *C07K 2319/00* (2013.01); *C12N 2730/10122* (2013.01)

(58) Field of Classification Search
CPC ......... A61K 39/29; A23K 1/14; C12M 23/14; C12M 35/04
See application file for complete search history.

(56) References Cited

U.S. PATENT DOCUMENTS 5,650,309 A * 7/1997 Wong-Staal et al. ......... 435/456
5,981,274 A * 11/1999 Tyrrell et al. ............. 435/320.1
6,133,244 A * 10/2000 Michel et al. ............... 514/44 R
7,001,760 B2 * 2/2006 Ryu et al. .................. 435/320.1

FOREIGN PATENT DOCUMENTS

EP          0783038 A1      7/1997
WO     WO96/36705 A1  *  11/1996
WO       WO 98/11916    *   3/1998

OTHER PUBLICATIONS

Ge et al. J. Viol. 2007, vol. 81 (1), pp. 155-158.*
Yang et al. Cellular Immunology, Available on line Jul. 27, 2006, pp. 14-21.*
Casimiro et al. (A) J. Virol. 2003, vol. 77, No. 11, pp. 6305-6313.*
Casimiro et al. (B) J. vol. 2003, vol. 77, No. 13, pp. 7663-7668.*
Han et al. Gene Therapy, 2008, vol. 15, pp. 700-701.*
Lachmann et al. Intervirology 1999, vol. 42, pp. 51-56.*
Pumpens et al. Intervology 2001, vol. 44, pp. 98-1414.*
Sun, Dian-xing et al., "Study on anti-HBV effects of genetically engineered replication-defective hepatitis B virus expressing dominant negative mutants of core protection," Chinese J. Exp. Clin. Virol., Jun. 2004, vol. 18, No. 2, pp. 145-149.
Wang, Liqun et al., "Approach to establishing a liver targeting gene therapeutic vector using naturally occurring defective hepatitis B viruses devoid of immunogenic T cell epitope," Virus Research, 85:2002, pp. 187-197.
Mancini-Bourgine, Maryline et al., "Induction or Expansion of T-Cell Responses by a Hepatitis B DNA Vaccine Administered to Chronic HBV Carriers," Hepatology, vol. 40, No. 4 (2004), pp. 874-881.
Lauterbach, Henning, "Reduced immune responses after vaccination with a recombinant herpes simplex virus type 1 vector in the presence of antiviral immunity," Journal of General Virology (2005), 86:pp. 2401-2410.
Yao, Feng et al., "Highly Efficient Regulation of Gene Expression by Tetracycline in a Replication-Defective Herpes Simplex Viral Vector," Molecular Therapy, vol. 13, No. 6, Jun. 2006, pp. 1133-1141.
Casimiro, Danilo R. et al., "Comparative Immunogenicity in Rhesus Monkeys of DNA Plasmid, Recombinant Vaccinia Virus, and Replication-Defective Adenovirus Vectors Expressing a Human Immunodeficiency Virus Type 1 *gag* Gene," Journal of Virology, Jun. 2003, pp. 6305-6313.
Bertoletti, Antonio et al., "The immune response during hepatitis B virus infection," Journal of General Virology (2006), 87:pp. 1439-1449.
Chisari, Francis V. et al., "Hepatitis B Virus Immunopathogenesis," Annu. Rev. Immunol. (1995), 13:pp. 29-60.
Ganem, Don et al., "Hepatitis B Virus Infection—Natural History and Clinical Consequences," The New England Journal of Medicine (2004), 350:pp. 1118-1129.

(Continued)

*Primary Examiner* — Bao Li
(74) *Attorney, Agent, or Firm* — Law Office of Salvatore Arrigo and Scott Lee, LLP

(57) ABSTRACT

This invention provides a new approach to the design of a virus with a defective replication cycle, which can be rescued by wild type virus co-infection, and which expresses foreign antigenic epitopes that contribute to the elimination of virus infected cells and then to viral clearance. The vector of the invention, by expression of epitopes derived from common pathogens, by-passes existing tolerance of virus specific T cell responses. The vector will only replicate in virus infected cells.

14 Claims, 27 Drawing Sheets

(56) References Cited

OTHER PUBLICATIONS

Günther, Stephan et al., "Enhanced Replication Contributes to Enrichmant of Hepatitis B Virus with a Deletion in the Core Gene," Virology (2000), 27:pp. 286-299.

Mancini, Maryline et al., "DNA-mediated immunization in a transgenic mouse model of the hepatitis B surface antigen chronic carrier state," Proc. Natl. Acad. Sci. USA, vol. 93, (Oct. 1996), pp. 12496-12501.

Morosan, Serban et al., "Liver-Stage Development of *Plasmodium falciparum*, in a Humanized Mouse Model," JID (2006), 193:pp. 996-1004.

Rehermann, Barbara et al., "Immunology of Hepatitis B Virus and Hepatitis C Virus Infection," Nature Reviews (2005), vol. 5:pp. 215-229.

Yang, Priscilla L. et al., "Hydrodynamic injection of viral DNA: A mouse model of acute hepatitis B virus infection," PNAS (Oct. 2002), vol. 99, No. 21:pp. 13825-13830.

Nakabayashi, Hidekazu et al., "Growth of Human Hepatoma Cell Lines with Differentiated Functions in Chemically Defined Medium," Cancer Research, vol. 42, pp. 3858-3863.

Pajot, Anthony et al., "A mouse model of human adaptive immune functions: *HLA-A2.1-/HLA-DR1*-transgenic *H-2 class I-/class II*-knockout mice," Eur. J. Immunol. (2004), 34:pp. 3060-3069.

Guidotti, Luca G. et al., "Noncytolytic Control of Viral Infections by the Innate and Adaptive Immune Response," Annu. Rev. Immunol. (2001), 19:pp. 65-91.

\* cited by examiner

| anti-HBs/HBsAg | anti-FLAG/rHBc | |
|---|---|---|
| 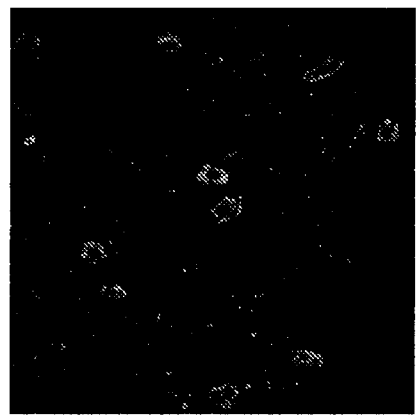 | 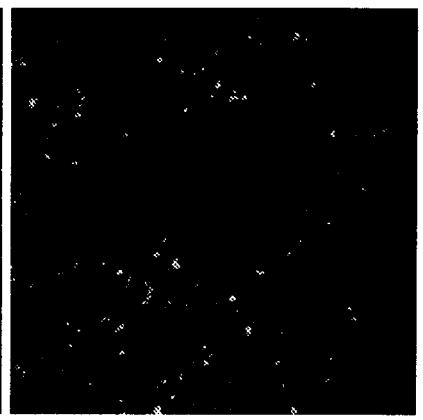 | prHBV1.3III |
| FIGURE 6A | FIGURE 6B | |
|  | 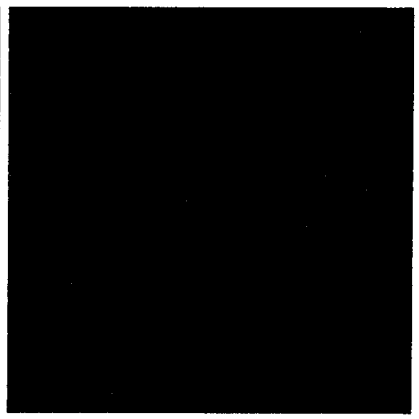 | PBS |
| FIGURE 6C | FIGURE 6D | |

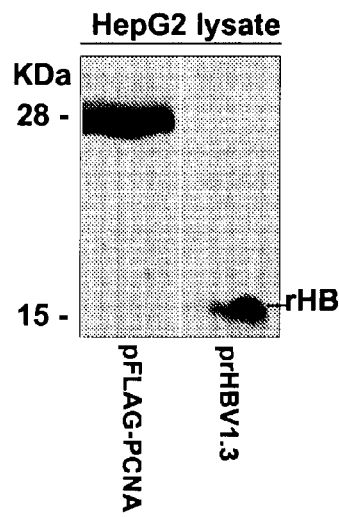
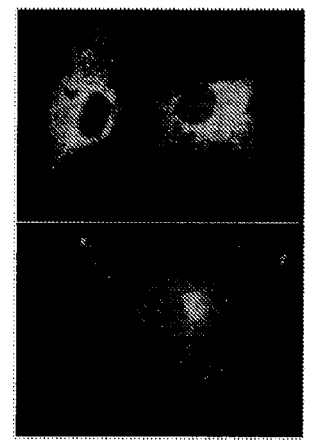
FIGURE 12A  FIGURE 12B
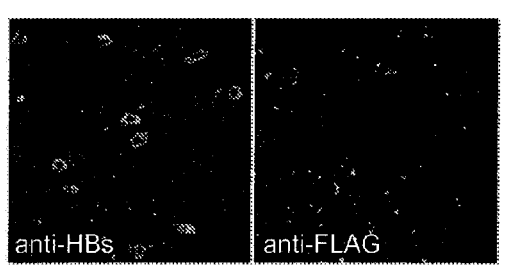
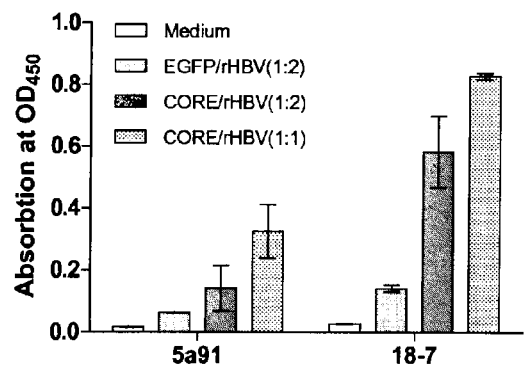
FIGURE 12C  FIGURE 12D

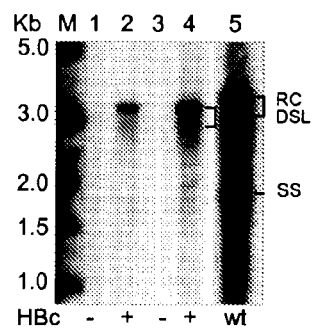
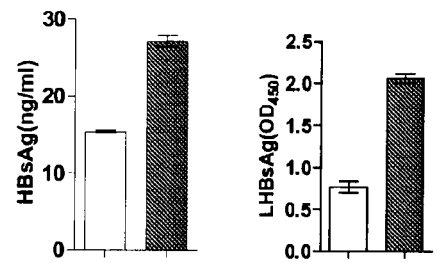
FIGURE 13A
FIGURE 13B
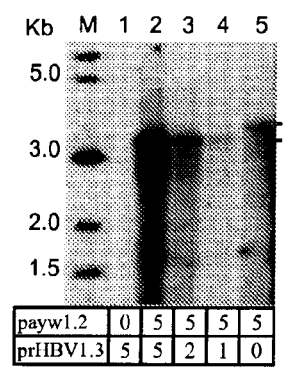
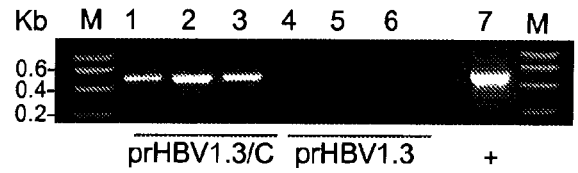
FIGURE 13C
FIGURE 13D

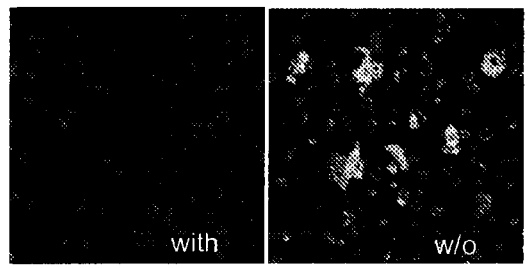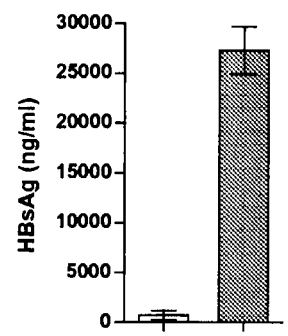
FIGURE 16D  FIGURE 16E
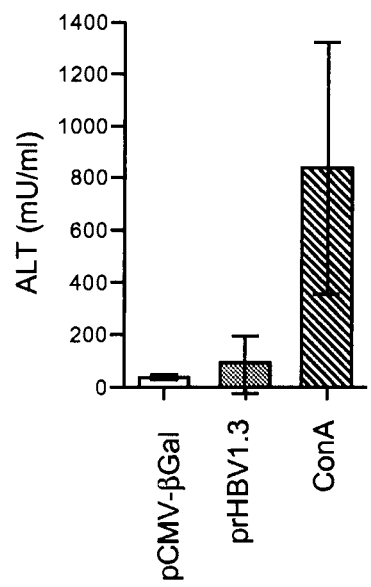
FIGURE 16F

Sequence for prHBV-1.3-III (SEQ ID NO: 4)
(polyepitope (polytope) sequence shadowed (SEQ ID NO: 5))

```
GACGGATCGGGAGATCTCCCGATCCCCTATGGTCGACTCTCAGTACAATCTGCTCTGATGCCGCATAGTTAAGCCAGTAT
CTGCTCCCTGCTTGTGTGTTGGAGGTCGCTGAGTAGTGCGCGAGCAAAATTTAAGCTACAACAAGGCAAGGCTTGACCGA
CAATTGCATGAAGAATCTGCTTAGGGTTAGGCGTTTTGCGCTGCTTCGCAATCTAAGCAGGCTTTCACTTTCTCGCCAAC
TTACAAGGCCTTTCTGTGTAAACAATACCTGAACCTTTACCCCGTTGCCCGGCAACGGCCAGGTCTGTGCCAAGTGTTTG
CTGACGCAACCCCCACTGGCTGGGGCTTGGTCATGGGCCATCAGCGCATGCGTGGAACCTTTTCGGCTCCTCTGCCGATC
CATACTGCGGAACTCCTAGC
CGCTTGTTTTGCTCGCAGCAGGTCTGGAGCAAACATTATCGGGACTGATAACTCTGTTGTCCTATCCCGCAAATATACAT
CGTTTCCATGGCTGCTAGGCTGTGCTGCCAACTGGATCCTGCGCGGGACGTCCTTTGTTTACGTCCCGTCGGCGCTGAAT
CCTGCGGACGACCCTTCTCGGGGTCGCTTGGGACTCTCTCGTCCCCTTCTCCGTCTGCCGTTCCGACCGACCACGGGGCG
CACCTCTCTTTACGCGGACTCCCCGTCTGTGCCTTCTCATCTGCCGGACCGTGTGCACTTCGCTTCACCTCTGCACGTCG
CATGGAGACCACCGTGAACGCCCACCAAATATTGCCCAAGGTCTTACATAAGAGGACTCTTGGACTCTCAGCAATGTCAA
CGACCGACCTTGAGGCATACTTCAAAGACTGTTTGTTTAAAGACTGGGAGGAGTTGGGGGAGGAGATTAGGTTAAAGGTC
TTTGTACTAGGAGGCTGTAGGCATAAATTGGTCTGCGCACCAGCACCATGCAACTTTTTCACCTCTGCCTAATCATCTCT
TGTTCATGTCCTACTGTTCAAGCCTCCAAGCTGTGCCTTGGGTGGCTTTGGGGCATGGACATCGACCCTTATAAAGAATT
TGGAGCTACTGTGGAGTTACTCTCGTTTTTGCCTTCTGACTTCTTTCCTTCAGTAAGCTTCGACTACAAGGACGACGACG
ACAAGAGCCTGTTAACACCGTGGCCACCCTGTACACCAAGGGCATCCTGGCTTCGTGTTCACCCTGAAGAACGCCGC
CTGTGCACCCTGGTGCCATGCTGCGCCCGGCCCGGCAAGGCCAAGTTCGTGCCGCCTGGACCCTGAAGGCTGCAGC
CGAACATGGAGCCCCTATCCTATCAACACTTCCGGAGACTACTGTTGTTAGACGACGAGGCAGGTCCCCTAGAAGAAGAA
CTCCCTCGCCTCGCAGACGAAGGTCTCAATCGCCGCGTCGCAGAAGATCTCAATCTCGGGAATCTCAATGTTAGTATTCC
TTGGACTCATAAGGTGGGGAACTTTACTGGGCTTTATTCTTCTACTGTACCTGTCTTTAATCCTCATTGGAAAACACCAT
CTTTTCCTAATATACATTTACACCAAGACATTATCAAAAAATGTGAACAGTTTGTAGGCCCACTCACAGTTAATGAGAAA
AGAAGATTGCAATTGATTATGCCTGCCAGGTTTTATCCAAAGGTTACCAAATATTTACCATTGGATAAGGGTATTAAACC
TTATTATCCAGAACATCTAGTTAATCATTACTTCCAAACTAGACACTATTTACACACTCTATGGAAGGCGGGTATATTAT
ATAAGAGAGAAACAACACATAGCGCCTCATTTTGTGGGTCACCATATTCTTGGGAACAAGATCTACAGCATGGGGCAGAA
TCTTTCCACCAGCAATCCTCTGGGATTCTTTCCCGACCACCAGTTGGATCCAGCCTTCAGAGCAAACACCGCAAATCCAG
ATTGGGACTTCAATCCCAACAAGGACACCTGGCCAGACGCCAACAAGGTAGGAGCTGGAGCATTCGGGCTGGGTTTCACC
CCACCGCACGGGAGGCCTTTTGGGGTGGAGCCCTCAGGCTCAGGAGCATACTACAAACTTTGCCAGCAAATCCGCCTCCTGC
CTCCACCAATCGCCAGTCAGGAAGGCAGCCTACCCCGCTGTCTCCACCTTTGAGAAACACTCATCCTCAGGCCATGCAGT
GGAATTCCACAACCTTCCACCAAACTCTGCAAGATCCCAGAGTGAGAGGCCTGTATTTCCCTGCTGGTGGCTCCAGTTCA
GGAACAGTAAACCCTGTTCTGACTACTGCCTCTCCCTTATCGTCAATCTTCTCGAGGATTGGGGACCCTGCGCTGAACAT
GGAGAACATCACATCAGGATTCCTAGGACCCCTTCTCGTGTTACAGGCGGGGTTTTCTTGTTGACAAGAATCCTCACAA
TACCGCAGAGTCTAGACTCGTGGTGGACTTCTCAATTTTCTAGGGGGAACTACCGTGTGTCTTGGCCAAAATTCGCAG
TCCCCAACCTCCAATCACTCACCAACCTCTTGTCCTCCAACTTGTCCTGGTTATCGCTGGATGTGTCTGCGGCGTTTAT
CATCTTCCTCTTCATCCTGCTGCTATGCCTCATCTTCTTGTTGGTTCTTCTGGACTATCAAGGTATGTTGCCCGTTTGTC
CTCTAATTCCAGGATCCTCAACAACCAGCACGGGACCATGCCGGACCTGCATGACTACTGCTCAAGGAACCTCTATGTAT
CCCTCCTGTTGCTGTACCAAACCTTCGGACGGAAATTGCACCTGTATTCCCATCCCATCATCCTGGGCTTTCGGAAAATT
CCTATGGGAGTGGGCCTCAGCCCGTTTCTCCTGGCTCAGTTTACTAGTGCCATTTGTTCAGTGGTTCGTAGGGCTTTCCC
CCACTGTTTGGCTTTCAGTTATATGGATGATGTGGTATTGGGGGCCAAGTCTGTACAGCATCTTGAGTCCCTTTTTACCG
CTGTTACCAATTTTCTTTTGTCTTTGGGTATACATTTAAACCCTAACAAAACAAAGAGATGGGGTTACTCTCTAAATTTT
ATGGGTTATGTCATTGGATGTTATGGGTCCTTGCCACAAGAACACATCATACAAAAAATCAAAGAATGTTTTAGAAAACT
TCCTATTAACAGGCCTATTGATTGGAAAGTATGTCAACGAATTGTGGGTCTTTTGGGTTTTGCTGCCCCTTTTACACAAT
GTGGTTATCCTGCGTTGATGCCTTTGTATGCATGTATTCAATCTAAGCAGGCTTTCACTTTCTCGCCAACTTACAAGGCC
TTTCTGTGTAAACAATACCTGAACCTTTACCCCGTTGCCCGGCAACGGCCAGGTCTGTGCCAAGTGTTTGCTGACGCAAC
CCCCACTGGCTGGGGCTTGGTCATGGGCCATCAGCGCATGCGTGGAACCTTTTCGGCTCCTCTGCCGATCCATACTGCGG
AACTCCTAGCCGCTTGTTTTGCTCGCAGCAGGTCTGGAGCAAACATTATCGGGACTGATAACTCTGTTGTCCTATCCCGC
AAATATACATCGTTTCCATGGCTGCTAGGCTGTGCTGCCAACTGGATCCTGCGCGGGACGTCCTTTGTTTACGTCCCGTC
GGCGCTGAATCCTGCGGACGACCCTTCTCGGGGTCGCTTGGGACTCTCTCGTCCCCTTCTCCGTCTGCCGTTCCGACCGA
CCACGGGGCGCACCTCTCTTTACGCGGACTCCCCGTCTGTGCCTTCTCATCTGCCGGACCGTGTGCACTTCGCTTCACCT
CTGCACGTCGCATGGAGACCACCGTGAACGCCCACCAAATATTGCCCAAGGTCTTACATAAGAGGACTCTTGGACTCTCA
GCAATGTCAACGACCGACCTTGAGGCATACTTCAAAGACTGTTTGTTTAAAGACTGGGAGGAGTTGGGGGAGGAGATTAG
```

FIGURE 18

```
GTTAAAGGTCTTTGTACTAGGAGGCTGTAGGCATAAATTGGTCTGCGCACCAGCACCATGCAACTTTTTCACCTCTGCCT
AATCATCTCTTGTTCATGTCCTACTGTTCAAGCCTCCAAGCTGTGCCTTGGGTGGCTTTGGGGCATGGACATCGACCCTT
ATAAAGAATTTGGAGCTACTGTGGAGTTACTCTCGTTTTTGCCTTCTGACTTCTTTCCTTCAGTACGAGATCCACTAGTT
CTAGAGCGGCCGCCACCGCGGTGGAGCTCCAGCTTTTGTTCCCTTTAGTGAGGGTTAATTGCGCGCATGCCCGACGGCGA
GGATCTCGTCGTGACCCATGGCGATGCCTGCTTGCCGAATATCATGGTGGAAAATGGCCGCTTTTCTGGATTCATCGACT
GTGGCCGGCTGGGTGTGGCGGACCGCTATCAGGACATAGCGTTGGCTACCCGTGATATTGCTGAAGAGCTTGGCGGCGAA
TGGGCTGACCGCTTCCTCGTGCTTTACGGTATCGCCGCTCCCGATTCGCAGCGCATCGCCTTCTATCGCCTTCTTGACGA
GTTCTTCTGAGCGGGACTCTGGGGTTCGAAATGACCGACCAAGCGACGCCCAACCTGCCATCACGAGATTTCGATTCCAC
CGCCGCCTTCTATGAAAGGTTGGGCTTCGGAATCGTTTTCCGGGACGCCGGCTGGATGATCCTCCAGCGCGGGATCTCA
TGCTGGAGTTCTTCGCCCACCCCAACTTGTTTATTGCAGCTTATAATGGTTACAAATAAAGCAATAGCATCACAAATTTC
ACAAATAAAGCATTTTTTTCACTGCATTCTAGTTGTGGTTTGTCCAAACTCATCAATGTATCTTATCATGTCTGTATACC
GTCGACCTCTAGCTAGAGCTTGGCGTAATCATGGTCATAGCTGTTTCCTGTGTGAAATTGTTATCCGCTCACAATTCCAC
ACAACATACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAGGCGGTTT
GCGTATTGGGCGCTCTTCCGCTTCCTCGCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAAAGAACATGTGAGCAAAAGGCCAGCAAAAG
GCCAGGAACCGTAAAAAGGCCGCGTTGCTGGCGTTTTTCCATAGGCTCCGCCCCCTGACGAGCATCACAAAAATCGACG
CTCAAGTCAGAGGTGGCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTTTCTCAATGCTCACGC
TGTAGGTATCTCAGTTCGGTGTAGGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCATGAGATTATCAAAAGGATCTTC
ACCTAGATCCTTTTAAATTAAAAATGAAGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAACCAAGT
CATTCTGAGAATAGTGTATGCGGCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTTACCGCTGTTGAGATCCAGTTC
GATGTAACCCACTCGTGCACCCAACTGATCTTCAGCATCTTTTACTTTCACCAGCGTTTCTGGGTGAGCAAAAACAGGAA
GGCAAAATGCCGCAAAAAAGGGAATAAGGGCGACACGGAAATGTTGAATACTCATACTCTTCCTTTTTCAATATTATTGA
AGCATTTATCAGGGTTATTGTCTCATGAGCGGATACATATTTGAATGTATTTAGAAAAATAAACAATAGGGGTTCCGCG
CACATTTCCCCGAAAAGTGCCACCTGACGTC
```

FIGURE 18(continued)

Sequence for rHBe_III_ (SEQ ID NO: 6)
(the recombinant protein; polyepitope (polytope) sequence shadowed SEQ ID NO: 7))

MDIDPYKEFGATVELLSFLPSDFFPSVSFDYKDDDDKSLFNTVATLYTKGILGFVFTLKNAGLCTLVAMLGPGPGKAKFV
AAWTLKAAAEHGAPILSTLPETTVVRRRGRSPRRRTPSPRRRRSQSPRRRRSQSRESQC

FIGURE 19

Sequence for polytope III (SEQ ID NO: 8)
(amino acids in small letters are flanking residues)

DYkDDDDKSLFNTVATLytkGILGFVFTLknaGLCTLVAMLgpgpgKAKFVAAWTLKAAA

FIGURE 20

Sequence for polytope IV (SEQ ID NO: 9)
(amino acids in small letters are flanking residues)

DYkDDDDKelrSLYNTVATLytkGILGFVFTLknaGLCTLVAMLgpgpgKAKFVAAWTLKAAA

FIGURE 21

Sequence for prHBV-1.3-IV (SEQ ID NO: 10)
(polyepitope (polytope) sequence shadowed (SEQ ID NO: 11))

```
GACGGATCGGGAGATCTCCCGATCCCCTATGGTCGACTCTCAGTACAATCTGCTCTGATGCCGCATAGTTAAGCCAGTAT
CTGCTCCCTGCTTGTGTGTTGGAGGTCGCTGAGTAGTGCGCGAGCAAAATTTAAGCTACAACAAGGCAAGGCTTGACCGA
CAATTGCATGAAGAATCTGCTTAGGGTTAGGCGTTTTGCGCTGCTTCGCAATCTAAGCAGGCTTTCACTTTCTCGCCAAC
TTACAAGGCCTTTCTGTGTAAACAATACCTGAACCTTTACCCCGTTGCCCGGCAACGGCCAGGTCTGTGCCAAGTGTTTG
CTGACGCAACCCCCACTGGCTGGGGCTTGGTCATGGGCCATCAGCGCATGCGTGGAACCTTTTCGGCTCCTCTGCCGATC
CATACTGCGGAACTCCTAGCCGCTTGTTTTGCTCGCAGCAGGTCTGGAGCAAACATTATCGGGACTGATAACTCTGTTGT
CCTATCCCGCAAATATACATCGTTTCCATGGCTGCTAGGCTGTGCTGCCAACTGGATCCTGCGCGGGACGTCCTTTGTTT
ACGTCCCGTCGGCGCTGAATCCTGCGGACGACCCTTCTCGGGGTCGCTTGGGACTCTCTCGTCCCCTTCTCCGTCTGCCG
TTCCGACCGACCACGGGGCGCACCTCTCTTTACGCGGACTCCCCGTCTGTGCCTTCTCATCTGCCGGACCGTGTGCACTT
CGCTTCACCTCTGCACGTCGCATGGAGACCACCGTGAACGCCCACCAAATATTGCCCAAGGTCTTACATAAGAGGACTCT
TGGACTCTCAGCAATGTCAACGACCGACCTTGAGGCATACTTCAAAGACTGTTTGTTTAAAGACTGGGAGGAGTTGGGGG
AGGAGATTAGGTTAAAGGTCTTTGTACTAGGAGGCTGTAGGCATAAATTGGTCTGCGCACCAGCACCATGCAACTTTTTC
ACCTCTGCCTAATCATCTCTTGTTCATGTCCTACTGTTCAAGCCTCCAAGCTGTGCCTTGGGTGGCTTTGGGGCATGGAC
ATCGACCCTTATAAAGAATTTGGAGCTACTGTGGAGTTACTCTCGTTTTGCCTTCTGACTTCTTTCCTTCAGTAAGCTT
CGACTACAAGGACGACGACGACAAGGAACTAAGAAGCCTGTACAACACCGTGGCCACCCTGTACACCAAGGGCATCCTGG
GCTTCGTGTTCACCCTGAAGAACGCCGGCCTGTGCACCCTGGTGGCCATGCTATCGGGCCCCGGCCCCGGCAAGGCCAAGTTC
GTGGCCGCCTGGACCCTGAAGGCTGCAGCCGAACATGGAGCCCCTATCCTATCAACACTTCCGGAGACTACTGTTGTTAG
ACGACGAGGCAGGTCCCCTAGAAGAAGAACTCCCTCGCCTCGCAGACGAAGGTCTCAATCGCCGCGTCGCAGAAGATCTC
AATCTCGGGAATCTCAATGTTAGTATTCCTTGGACTCATAAGGTGGGGAACTTTACTGGGCTTTATTCTTCTACTGTACC
TGTCTTTAATCCTCATTGGAAAACACCATCTTTTCCTAATATACATTTACACCAAGACATTATCAAAAAATGTGAACAGT
TTGTAGGCCCACTCACAGTTAATGAGAAAAGAAGATTGCAATTGATTATGCCTGCCAGGTTTTATCCAAAGGTTACCAAA
TATTTACCATTGGATAAGGGTATTAAACCTTATTATCCAGAACATCTAGTTAATCATTACTTCCAAACTAGACACTATTT
ACACACTCTATGGAAGGCGGGTATATTATATAAGAGAGAAACAACACATAGCGCCTCATTTTGTGGGTCACCATATTCTT
GGGAACAAGATCTACAGCATGGGGCAGAATCTTTCCACCAGCAATCCTCTGGGATTCTTTCCCGACCACCAGTTGGATCC
AGCCTTCAGAGCAAACACCGCAAATCCAGATTGGGACTTCAATCCCAACAAGGACACCTGGCCAGACGCCAACAAGGTAG
GAGCTGGAGCATTCGGGCTGGGTTTCACCCCACCGCACGGAGGCCTTTTGGGGTGGAGCCCTCAGGCTCAGGGCATACTA
CAAACTTTGCCAGCAAATCCGCCTCCTGCCTCCACCAATCGCCAGTCAGGAAGGCAGCCTACCCCGCTGTCTCCACCTTT
GAGAAACACTCATCCTCAGGCCATGCAGTGGAATTCCACAACCTTCCACCAAACTCTGCAAGATCCCAGAGTGAGAGGCC
TGTATTTCCCTGCTGGTGGCTCCAGTTCAGGAACAGTAAACCCTGTTCTGACTACTGCCTCTCCCTTATCGTCAATCTTC
TCGAGGATTGGGGACCCTGCGCTGAACATGGAGAACATCACATCAGGATTCCTAGGACCCCTTCTCGTGTTACAGGCGGG
GTTTTTCTTGTTGACAAGAATCCTCACAATACCGCAGAGTCTAGACTCGTGGTGGACTTCTCTCAATTTTCTAGGGGGAA
CTACCGTGTGTCTTGGCCAAAATTCGCAGTCCCCAACCTCCAATCACTCACCAACCTCTTGTCCTCCAACTTGTCCTGGT
TATCGCTGGATGTGTCTGCGGCGTTTTATCATCTTCCTCTTCATCCTGCTGCTATGCCTCATCTTCTTGTTGGTTCTTCT
GGACTATCAAGGTATGTTGCCCGTTTGTCCTCTAATTCCAGGATCCTCAACAACCAGCACGGGACCATGCCGGACCTGCA
TGACTACTGCTCAAGGAACCTCTATGTATCCCTCCTGTTGCTGTACCAAACCTTCGGACGGAAATTGCACCTGTATTCCC
ATCCCATCATCCTGGGCTTTCGGAAAATTCCTATGGGAGTGGGCCTCAGCCCGTTTCTCCTGGCTCAGTTTACTAGTGCC
ATTTGTTCAGTGGTTCGTAGGGCTTTCCCCCACTGTTTGGCTTTCAGTTATATGGATGATGTGGTATTGGGGGCCAAGTC
TGTACAGCATCTTGAGTCCCTTTTTACCGCTGTTACCAATTTTCTTTTGTCTTTGGGTATACATTTAAACCCTAACAAAA
CAAAGAGATGGGGTTACTCTCTAAATTTTATGGGTTATGTCATTGGATGTTATGGGTCCTTGCCACAAGAACACATCATA
CAAAAAATCAAAGAATGTTTTAGAAAACTTCCTATTAACAGGCCTATTGATTGGAAAGTATGTCAACGAATTGTGGGTCT
TTTGGGTTTTGCTGCCCCTTTTACACAATGTGGTTATCCTGCGTTGATGCCCTGTATGCATGTATTCAATCTAAGCAGG
CTTTCACTTTCTCGCCAACTTACAAGGCCTTTCTGTGTAAACAATACCTGAACCTTTACCCCGTTGCCCGGCAACGGCCA
GGTCTGTGCCAAGTGTTTGCTGACGCAACCCCCACTGGCTGGGGCTTGGTCATGGGCCATCAGCGCATGCGTGGAACCTT
TTCGGCTCCTCTGCCGATCCATACTGCGGAACTCCTAGCCGCTTGTTTTGCTCGCAGCAGGTCTGGAGCAAACATTATCG
GGACTGATAACTCTGTTGTCCTATCCCGCAAATATACATCGTTTCCATGGCTGCTAGGCTGTGCTGCCAACTGGATCCTG
CGCGGGACGTCCTTTGTTTACGTCCCGTCGGCGCTGAATCCTGCGGACGACCCTTCTCGGGGTCGCTTGGGACTCTCTCG
```

FIGURE 22

```
TCCCCTTCTCCGTCTGCCGTTCCGACCGACCACGGGGCGCACCTCTCTTTACGCGGACTCCCCGTCTGTGCCTTCTCATC
TGCCGGACCGTGTGCACTTCGCTTCACCTCTGCACGTCGCATGGAGACCACCGTGAACGCCCACCAAATATTGCCCAAGG
TCTTACATAAGAGGACTCTTGGACTCTCAGCAATGTCAACGACCGACCTTGAGGCATACTTCAAAGACTGTTTGTTTAAA
GACTGGGAGGAGTTGGGGGAGGAGATTAGGTTAAAGGTCTTTGTACTAGGAGGCTGTAGGCATAAATTGGTCTGCGCACC
AGCACCATGCAACTTTTTCACCTCTGCCTAATCATCTCTTGTTCATGTCCTACTGTTCAAGCCTCCAAGCTGTGCCTTGG
GTGGCTTTGGGGCATGGACATCGACCCTTATAAAGAATTTGGAGCTACTGTGGAGTTACTCTCGTTTTTGCCTTCTGACT
TCTTTCCTTCAGTACGAGATCCACTAGTTCTAGAGCGGCCGCCACCGCGGTGGAGCTCCAGCTTTTGTTCCCTTTAGTGA
GGGTTAATTGCGCGCATGCCCGACGGCGAGGATCTCGTCGTGACCCATGGCGATGCCTGCTTGCCGAATATCATGGTGGA
AAATGGCCGCTTTTCTGGATTCATCGACTGTGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTGCTTTACGGTATCGCCGCTCCCGATTCGCAG
CGCATCGCCTTCTATCGCCTTCTTGACGAGTTCTTCTGAGCGGGACTCTGGGGTTCGAAATGACCGACCAAGCGACGCCC
AACCTGCCATCACGAGATTTCGATTCCACCGCCGCCTTCTATGAAAGGTTGGGCTTCGGAATCGTTTTCCGGGACGCCGG
CTGGATGATCCTCCAGCGCGGGGATCTCATGCTGGAGTTCTTCGCCCACCCCAACTTGTTTATTGCAGCTTATAATGGTT
ACAAATAAAGCAATAGCATCACAAATTTCACAAATAAAGCATTTTTTTCACTGCATTCTAGTTGTGGTTTGTCCAAACTC
ATCAATGTATCTTATCATGTCTGTATACCGTCGACCTCTAGCTAGAGCTTGGCGTAATCATGGTCATAGCTGTTTCCTGT
GTGAAATTGTTATCCGCTCACAATTCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCACCTGACGTC
```

FIGURE 22(Continued)

Sequence for rHBe_IV_ (SEQ ID NO: 12)
(the recombinant protein; polyepitope (polytope) sequence shadowed (SEQ ID NO: 13))

MDIDPYKEFGATVELLSFLPSDFFPSVSF<mark>DYKDDDDKELRSLYNTVATLYTKGILGFVFTLKNAGLCTLVAMLGPGPGKA</mark>
<mark>KFVAAWTLKAAA</mark>EHGAPILSTLPETTVVRRRGRSPRRRTPSPRRRRSQSPRRRRSQSRESQC

FIGURE 23

NCBI Accession Number: V01460 Hepatitis B virus (strain ayw) genome, DNA sequence.
(ACCESSION V01460 J02203 VERSION V01460.1 GI:62276, VRL 28-JAN-2003) (SEQ ID NO: 14)

```
   1 aattccactg catggcctga ggatgagtgt ttctcaaagg tggagacagc ggggtaggct
  61 gccttcctga ctggcgattg gtggaggcag gaggcggatt tgctggcaaa gtttgtagta
 121 tgccctgagc ctgagggctc caccccaaaa ggcctccgtg cggtggggtg aaacccagcc
 181 cgaatgctcc agctcctacc ttgttggcgt ctggccaggt gtccttgttg ggattgaagt
 241 cccaatctgg atttgcggtg tttgctctga aggctggatc caactggtgg tcgggaaaga
 301 atcccagagg attgctggtg gaaagattct gccccatgct gtagatcttg ttcccaagaa
 361 tatggtgacc cacaaaatga ggcgctatgt gttgtttctc tcttatataa tatacccgcc
 421 ttccatagag tgtgtaaata gtgtctagtt tggaagtaat gattaactag atgttctgga
 481 taataaggtt taatacccct atccaatggt aaatatttgg taacctttgg ataaaacctg
 541 gcaggcataa tcaattgcaa tcttcttttc tcattaactg tgagtgggcc tacaaactgt
 601 tcacatttt tgataatgtc ttggtgtaaa tgtatattag aaaagatgg tgttttccaa
 661 tgaggattaa agacaggtac agtagaagaa taaagcccag taaagttccc caccttatga
 721 gtccaaggaa tactaacatt gagattcccg agattgagat cttctgcgac gcggcgattg
 781 agaccttcgt ctgcgaggcg agggagttct tcttctaggg gacctgcctc gtcgtctaac
 841 aacagtagtc tccggaagtg ttgataggat aggggcattt ggtggtctat aagctggagg
 901 agtgcgaatc cacactccga aagacaccaa atactctata actgtttctc ttccaaaagt
 961 gagacaagaa atgtgaaacc acaagagttg cctgaacttt aggcccatat tagtgttgac
1021 ataactgact actaggtctc tagacgctgg atcttccaaa ttaacaccca cccaggtagc
1081 tagagtcatt agttcccccc agcaaagaat tgcttgcctg agtgcagtat ggtgaggtga
1141 acaatgctca ggagactcta aggcttcccg atacagagct gaggcggtat ctagaagatc
1201 tcgtactgaa ggaaagaagt cagaaggcaa aaacgagagt aactccacag tagctccaaa
1261 ttcttttataa gggtcgatgt ccatgcccca aagccaccca aggcacagct tggaggcttg
1321 aacagtagga catgaacaag agatgattag gcagaggtga aaaagttgca tggtgctggt
1381 gcgcagacca atttatgcct acagcctcct agtacaaaga cctttaacct aatctcctcc
1441 cccaactcct cccagtcttt aaacaaacag tctttgaagt atgcctcaag tcggtcgtt
1501 gacattgctg agagtccaag agtcctctta tgtaagacct tgggcaatat ttggtgggcg
1561 ttcacggtgg tctccatgcg acgtgcagag gtgaagcgaa gtgcacacgg tccggcagat
1621 gagaaggcac agacggggag tccgcgtaaa gagaggtgcg ccccgtggtc ggtcggaacg
1681 gcagacggag aaggggacga gagagtccca agcgaccccg agaagggtcg tccgcaggat
1741 tcagcgccga cgggacgtaa acaaaggacg tcccgcgcag gatccagttg gcagcacagc
1801 ctagcagcca tggaaacgat gtatatttgc gggataggac aacagagtta tcagtcccga
1861 taatgtttgc tccagacctg ctgcgagcaa aacaagcggc taggagttcc gcagtatgga
1921 tcggcagagg agccgaaaag gttccacgca tgcgctgatg gcccatgacc aagccccagc
1981 cagtgggggt tgcgtcagca aacacttggc acagacctgg ccgttgccgg gcaacggggt
2041 aaaggttcag gtattgttta cacagaaagg ccttgtaagt tggcgagaaa gtgaaagcct
2101 gcttagattg aatacatgca tacaaaggca tcaacgcagg ataaccacat tgtgtaaaag
2161 gggcagcaaa acccaaaaga cccacaattc gttgacatac tttccaatca ataggcctgt
2221 taataggaag ttttctaaaa cattctttga tttttttgtat gatgtgttct tgtggcaagg
2281 acccataaca tccaatgaca taacccataa aatttagaga gtaacccat ctctttgttt
2341 tgttagggtt taaatgtata cccaaagaca aaagaaaatt ggtaacagcg taaaaaggg
2401 actcaagatg ctgtacagac ttggcccccca ataccacatc atccatataa ctgaaagcca
2461 aacagtgggg gaaagcccta cgaaccactg aacaaatggc actagtaaac tgagccagga
2521 gaaacgggct gaggcccact cccataggaa ttttccgaaa gcccaggatg atgggatggg
2581 aatacaggtg caatttccgt ccgaaggttt ggtacagcaa caggagggat acatagaggt
2641 tccttgagca gtagtcatgc aggtccggca tggtcccgtg ctggttgttg aggatcctgg
2701 aattagagga caaacgggca ataccttg atagtccaga gaaccaaca agaagatgag
2761 gcatagcagc aggatgaaga ggaagatgat aaaacgccgc agacacatcc agcgataacc
2821 aggacaagtt ggaggacaag aggttggtga gtgattggag gttggggact gcgaattttg
2881 gccaagacac acggtagttc cccctagaaa attgagagaa gtccaccacg agtctagact
2941 ctgcggtatt gtgaggattc ttgtcaacaa gaaaacccc gcctgtaaca cgagaagggg
3001 tcctaggaat cctgatgtga tgttctccat gttcagcgca gggtccccaa tcctcgagaa
3061 gattgacgat aagggagagg cagtagtcag aacagggttt actgttcctg aactggagcc
3121 accagcaggg aaatacaggc ctctcactct gggatcttgc agagtttggt ggaaggttgt
3181 gg
```

FIGURE 24

POLYNUCLEOTIDES ALLOWING THE EXPRESSION AND SECRETION OF RECOMBINANT PSEUDO-VIRUS CONTAINING FOREIGN EPITOPES, THEIR PRODUCTION, AND USE

This application is the U.S. national stage of International Application No. PCT/EP2008/062208, filed Sep. 12, 2008, which claims priority to U.S. Provisional Application No. 60/960,091, filed Sep. 14, 2007, U.S. Provisional Application No. 61/136,125, filed Aug. 13, 2008, and U.S. Provisional Application No. 61/136,154, filed Aug. 14, 2008.

This invention relates to polynucleotides for the expression of a recombinant, replication defective virus involved in a persistent infection, and to a recombinant, replication competent pseudo-virus, comprising the recombinant replication defective virus, and to the production of the viruses in host cells. The recombinant, replication defective virus and the replication competent pseudo-virus can contain a foreign epitope or epitopes, such as foreign amino acid residues of a pathogen. The replication defective virus and the replication competent pseudo-virus are particularly useful in immunogenic compositions and as therapeutic vaccines. This invention also relates to T cell responses to viral infection and to recombinant viruses that deliver foreign antigenic epitopes to the liver and induce epitope-specific immune responses.

BACKGROUND OF THE INVENTION

An effective vaccine against hepatitis B virus (HBV) infection has been available for more than two decades, but 400 million people—more than 5% of the world's population—are chronically infected with HBV. More than 1 million people die each year from HBV-related liver cirrhosis and hepatocellular carcinoma. (Ganem D., Prince, A. M. (2004) Hepatitis B virus infection—natural history and clinical consequences, N Engl J Med 350:1118-29).

HBV is mainly not directly cytopathic. The immune response to viral antigens is thought to be responsible for both liver disease and viral clearance following HBV infection (Ganem et al., 2004). Immune responses with virus-specific $CD8^-$ cytotoxic T lymphocytes (CTLs) and $CD4^+$ T-helper (Th) cells play key effector and regulatory roles in both liver pathogenesis and viral clearance. HBV acute infection in immunocompetent adults usually results in a transient self-limited liver disease followed by viral clearance, and is characterized by vigorous polyclonal CTLs and type 1-Th responses specific for a number of epitopes within HBV viral proteins.

Patients with acute viral infection, who successfully clear the virus, display a multispecific polyclonal cytotoxic T-lymphocyte (CTL) response specific for a number of epitopes within the core, polymerase, and envelope proteins. Viral specific, e.g., HBV-specific Th cells are also activated. Multispecific Th1-like responses have been detected in patients successfully clearing HBV after acute infection (Chisari et al., 1995, Hepatitis B virus immunopathogenesis, Annu Rev Immunol 13:29-60).

The HBV-specific T-cell response is weak or undetectable in patients who develop chronic infection and the mechanisms responsible for T cell hypo-responsiveness or tolerance in chronic infection are not completely understood. In chronically infected patients, the peripheral $CD8^+$ T cell response is undetectable or weak and the $CD4^+$ T cell response is much less vigorous than in patients who clear the infection.

Although functional effector T cells are initially generated during the early stages of infection, they gradually lose function during the course of a chronic infection by upregulating the programmed death 1 (PD-1) inhibitory receptor (Chisari et al., 1995). Accordingly, in chronic patients who spontaneously clear hepatitis B surface antigen (HBsAg) and develop neutralizing anti-HBs antibodies, HBV-specific T-cell responses have been detected in the blood just before seroconversion. It has also been shown that effective therapeutic reduction of HBV viral load resulted in a transient restoration of HBV-specific $CD4^-$ and $CD8^+$ T-cell responses in the blood from patients with chronic hepatitis B.

The mechanisms responsible for T cell hypo-responsiveness and exhaustion during HBV persistent infection are still not completely understood. (Rehermann B., Nascimbeni M., 2005, Immunology of hepatitis B virus and hepatitis C virus infection, Nat Rev Immunol 5:215-29). Exhausted T cell responses observed during persistent viral infection reflect a balance between effector functions required to eliminate the pathogen and the potential of T cells to cause immunopathology. Impaired dendritic cell functions and the presence of $CD4^+$ $CD25^-$ regulatory T cells also contribute to the viral persistence. Moreover, the liver particularly biases the intrahepatic T cell response towards tolerance or anergy.

Active immunotherapy based on specific viral-epitopes and hepatitis vaccine injection provide promising approaches in inducing efficient cellular immune responses. A previous study of a phase I clinical trial suggested that HBV DNA vaccination could specifically restore T-cell responsiveness in chronic HBV carriers. However, the activation of HBV-specific T-cells appeared to be transient and was followed by a progressive decline along the DNA injections (Mancini-Bourgine M., Fontaine H., Scott-Algara D., Pol S., Brechot C., Michel M. L., 2004, Induction or expansion of T-cell responses by a hepatitis B DNA vaccine administered to chronic HBV carriers, Hepatology 40:874-82). Bypassing the potential tolerance of T cells to HBV antigens, therefore, turns out to be a most crucial point in immunotherapy.

Collectively this suggests that, to treat chronic hepatitis, e.g., HBV, infection, the intrahepatic T cell responses should be switched from a state of exhaustion or anergy to a state in which the effector T cells are fully efficient. (Bertoletti A., Gehring A. J., 2006, The immune response during hepatitis B virus infection, J Gen Virol 87:1439-49; Rehermann et al., 2005).

Accordingly, there exists a need in the art for new therapies for the treatment of chronic hepatitis infection, for example, hepatitis B infection. These therapies should also be generally useful in the treatment of other viral persistent infections. The therapies should also be specific for the cells infected with the virus involved in the persistent infection. For example, in the case of a hepatitis viral infection, the therapies should be specific for hepatitis virus infected cells, especially human hepatocytes (Rehermann et al., 2005).

SUMMARY OF THE INVENTION

This invention aids in fulfilling these needs in the art. To achieve these results, this invention provides a recombinant, replication defective virus that co-maintains in vivo with wild type virus in cells infected with said virus, and that immunologically contributes, after complementation, to virus clearance by expressing foreign antigenic epitopes in virus infected cells. The invention provides a pseudo-virus to achieve these results. The recombinant defective virus of the invention comprises a genome defective for the expression of a protein essential for virus replication. Examples of such proteins are structural proteins and more particularly, capsid proteins.

The invention also provides a novel vaccine strategy modeled on the use of hepatitis virus as a vector to deliver foreign antigenic epitopes into the liver. Presentation of these epitopes by liver cells would, in turn, attract efficient (i.e., non-exhausted) T cell responses to the target tissue, for example, the liver, and contribute to viral clearance.

In one embodiment, the recombinant, replication defective virus is hepatitis virus that co-maintains in vivo with wild type hepatitis virus in hepatitis virus-infected hepatocytes, and that immunologically contributes, after complementation, to hepatitis virus clearance by expressing foreign antigenic epitopes in hepatitis virus-infected hepatocytes. The invention provides a hepatitis pseudo-virus to achieve these results.

More particularly, the invention involves the design of polynucleotides and expression vectors for cloning and expressing foreign peptides or polypeptides, such as Flu polyepitopes, in the pseudo-virus. In one embodiment, the polynucleotides and expression vectors are designed for cloning and expressing foreign peptides or polypeptides, such as Flu polyepitopes, in the hepatitis pseudo-virus. Polynucleotides and expression vectors comprising these polynucleotides have been designed, all preserving recombinant hepatitis pseudo-virus formation.

In one embodiment, this invention provides a recombinant replication defective hepatitis virus comprising a hepatitis virus genome defective for the expression of hepatitis virus capsid protein (HBc). The virus contains a nucleotide sequence of up to about 195 nucleotides encoding at least one immuno-dominant epitope of a pathogen. The nucleotide sequence is located between nucleotide residue 1981 and nucleotide residue 2308 of the HBV ayw3 genome (numbering starts from the EcoRI site of the HBV genome, NCBI Accession No. V01460). Hepatitis B is a preferred virus for use in practicing the invention.

A vertebrate cell, transfected by the recombinant, replication defective virus of the invention is also provided. In one embodiment, the vertebrate cell is a hepatocyte cell and the virus is hepatitis virus. In one embodiment, the recombinant virus can be produced by co-transfection of a hepatocytic cell line such as Huh 7 (11) or Hep G2 (12) by one of the two constructs prHBV1.3-III or -IV with a plasmid encoding wild type capsid (pCMV-core or pMAS-core) or by transfection with a plasmid such as prHBV1.3/HB, which carries 1.3 copies of the rHBV genome and an additional expression cassette for HBV wild type core protein. The hepatocyte cell can further comprise a nucleotide sequence encoding HBc for complementation of the recombinant, replication defective, hepatitis virus to form the hepatitis pseudo-virus.

This invention thus provides a replication competent pseudo-virus comprising the recombinant, replication defective virus, complemented by the capsid protein of the virus, wherein the pseudo-virus replicates in vitro in human cells. In one embodiment, the replication competent pseudo-virus is a hepatitis pseudo-virus comprising the recombinant, replication defective hepatitis virus complemented by HBc, wherein the pseudo-virus replicates in vitro in human hepatocytes.

Further, this invention provides a vertebrate cell, expressing the pseudo-virus. In one embodiment, the vertebrate cell is a hepatocyte cell expressing the hepatitis pseudo-virus.

In addition, this invention provides a method of forming a replication competent pseudo-virus, wherein the method comprises culturing the infected cells of the invention under conditions for expression of the nucleotide sequence encoding the capsid protein of the virus and complementation of the recombinant, replication defective virus to form the pseudo-virus, which can optionally be secreted from the host cell into extracellular space. In one embodiment, the method can be used to form a replication competent hepatitis pseudo-virus by culturing the infected hepatocyte cells of the invention under conditions for expression of the nucleotide sequence encoding HBc and complementation of the recombinant, replication defective hepatitis virus to form the hepatitis pseudo-virus, which can optionally be secreted from the host cell into the extracellular space.

A polynucleotide hybridizing under stringent conditions to the recombinant, replication defective virus or its complement is also provided. In one embodiment, the polynucleotide hybridizes under stringent conditions to the recombinant, replication defective hepatitis virus or its complement.

A cloning and/or expression vector comprising the recombinant, replication defective virus is further provided. In one embodiment, the cloning and/or expression vector comprises the recombinant, replication defective hepatitis virus.

Polypeptides encoded by the recombinant, replication defective virus and by the replication competent pseudo-virus are also provided. In one embodiment, the polypeptides are encoded by the recombinant, replication defective hepatitis virus and by the replication competent hepatitis pseudo-virus.

Further, this invention provides a eukaryotic host cell comprising a vector of the invention. In one embodiment, the vector in the eukaryotic host cell comprises a eukaryotic promoter sequence operably linked to a nucleotide sequence for expression of hepatitis pseudo-virus. Optionally, the vector can comprise a nucleotide sequence encoding a fusion protein comprising a foreign polypeptide and a viral protein, wherein the eukaryotic host cell produces pseudo-virus comprising the fusion protein. In one embodiment, the fusion protein comprises a hepatitis protein and the eukaryotic host cell produces hepatitis pseudo-virus comprising the fusion protein.

More particularly, in certain embodiments, this invention relates to a vector derived from the HBV genome. The HBV genome is modified in order to express foreign antigenic epitope(s) fused within the N-terminal part of the HBV capsid protein yielding a recombinant HBV virus that will co-maintain in the liver of HBV-infected individuals through wild type capsid complementation. The HBV genome can be further modified to allow the expression and presentation of foreign epitope(s) at the surface of hepatocytes after infection with this recombinant HBV virus. The foreign antigenic epitope(s) can be derived from common pathogens that are presented in association of MHC class 1 molecules and serve as targets of the host CD8+ T-cell immune response. The replication of the recombinant HBV vector in already HBV-infected hepatocytes can thereby immunologically contribute to HBV clearance by expressing foreign antigenic epitope(s) in HBV-infected hepatocytes.

Only virus-infected cells that allow replication of the recombinant virus vector of the invention are the targets of the immune response. In one embodiment, the virus-infected cells are hepatitis virus-infected hepatocytes that allow replication of the recombinant hepatitis virus vector of the invention. The recombinant, replication defective virus delivers foreign antigenic epitope(s) (for instance, polyepitopes) via the replication competent pseudo-virus of the invention in the cells of a vertebrate, and subsequently elicits strong (poly) epitope-specific immune responses. In one embodiment, the recombinant, replication defective virus is a recombinant, replication defective hepatitis virus and the vertebrate cells are hepatocytes. Hepatitis virus is cleared through cytolytic or non-cytolytic mechanisms.

The pseudo-virus of the invention results in the induction of robust immune responses and the enhancement of the activation state of sequence-specific CD4+ and CD8+ T lymphocytes so that the pseudo-virus can be employed in therapeutic applications. In one embodiment, the pseudo-virus of the invention is a hepatitis pseudo-virus.

The prHBV1.3 DNA may be used as a DNA vaccine for therapeutic intervention in chronically HBV-infected patients. This construct expresses the three HBV envelope proteins, the polymerase, and the HBx protein. The vector is non-replicative when administrated as DNA through a systemic route. The pCMV-rHBe construct encodes a secreted form of HBeAg carrying foreign epitopes. It induces T cell responses specific for the foreign epitope and can be used as a vector for DNA immunization against pathogens harboring those epitopes.

Accordingly, the invention provides a composition comprising the replication defective virus of the invention and a vaccine comprising said composition. The vaccines of the invention may be administered to a patient persistently infected with a virus in order to stimulate a T cell response against cells infected with the virus. Thus, the invention also contemplates the use of the recombinant replication defective viruses of the invention for the preparation of a medicament for treating a patient persistently infected with the wild type virus. The invention also contemplates a method for targeting the expression of an epitope in a cell infected with a virus by providing to the cell the recombinant replication defective virus of the invention.

The invention provides antibodies to the chimeric antigenic fusion proteins produced by the pseudoviruses of the invention.

The invention also provides a mouse, for example, an HLA-A2/DR1 or an HbsAg/HLA-A2 double transgenic mouse, comprising a plasmid described herein. The plasmid may have entered the cells of the mouse using any method known in the art for producing transgenic animals. In an embodiment, the animal is injected intramuscularly or hydrodynamically, e.g., through a tail vein.

In an embodiment, the animal comprises prHBV-1.3, e.g., prHBV-1.3-III or prHBV-1.3-IV. In an embodiment, the transgenic animal comprises a plasmid comprising a polynucleotide sequence encoding rHBe_III, rHBe_IV, polytope III, or polytope IV.

In an embodiment, the percentage of CD8+ T cells of the transgenic animal increases in response to infection with a pseudo-virus of the invention. In an embodiment, the transgenic animal mounts an epitope-specific T-cell response to a pseudo-virus of the invention. In an embodiment, a rHBV is expressed in liver cells, with an encoded foreign antigen processed into polypeptides for immune recognition.

The invention provides a method of vaccinating an animal chronically infected with a pathogenic virus by providing a recombinant replication-competent pseudo-virus comprising the recombinant, replication defective virus, complemented by the capsid protein of the virus. In an embodiment, the animal is a mammal, e.g., a human. In an embodiment, the plasmid is any of the plasmids of the invention, as described in greater detail herein.

BRIEF DESCRIPTION OF THE DRAWINGS

This invention will be described with reference to the drawings in which:

FIG. 3A: HBV DNA was PCR amplified.

FIG. 3B: depicts the production of HBsAg carrying particles in the supernatant from these cells.

FIG. 3C: depicts LHBs-virion rescue. This is also depicted in FIG. 12D.

FIGS. 6A-6D show immunostaining of the foreign recombinant antigen in liver sections after hydrodynamic injection of prHBV1.3-III into mice (ATCC number HB-8065). This is also shown in FIG. 12C.

FIG. 10A: Immunization time-line; prHBV1.3 (dotted square), pCMV-βGal (control plasmid, empty square), pCMV-rHBe (grey square).

FIG. 10B: Fluorescence Activated Cell Sorting (FACS) analysis of liver infiltrating lymphocytes; non-injected mice (panel B1), mice receiving pCMV-βGal (panel B2), mice receiving prHBV1.3 (panel B3); lower panels show Flu-specific T cells staining for each treatment.

FIG. 10C: Localization of T cells and Flu-specific T cells in spleen (upper panel) and liver (lower panel); mice receiving hydrodynamic injection of prHBV1.3 (dotted bars), mice receiving pCMV-βGal (empty bars), mice receiving pCMV-rHBe (grey bars).

FIG. 11A: HBV pregenomic RNA (HBV/pgRNA) is represented by a thin blue line with a capping site (cap), encapsidation (E), and polyadenylation ($A_n$) signals indicated. The distance between AUG codons of the core and polymerase (pol) open reading frames is 406 nucleotides (nts).

FIG. 11B: rHBV pregenomic RNA is shown; a short DNA sequence (in blue) encoding the foreign antigenic polyepitope was inserted in-frame within the core open reading frame, allowing the expression of a chimeric protein (rHBc).

FIG. 11C: A schematic representation of the rHBc-encoding domain shows two in-frame ATG codons for the expression of HBe antigen and for core protein, respectively. A polyepitope comprising a B cell epitope (FLAG) used as a detection marker; three HLA-A2 restricted CD8 T-cell epitopes derived respectively from HIV Gag, influenza matrix, and EBV BMLF-1 proteins; and a universal CD4-T cell epitope PADRE. The polyepitope sequences were inserted in-frame within the amino terminal portion of the core gene.

FIG. 11D: A schematic representation of plasmids is shown. The pCMVrHBc plasmid allows expression of rHBc as well as the rHBV genome under the control of CMV early gene promoter (P-CMV). The prHBV1.3 plasmid carries 1.3 copies of the rHBV genome. The prHBV1.3/HBc plasmid carries, in addition to the 1.3 copies of rHBV genome, a cassette for the expression of wild type HBV core gene, under the control of an SV40 early gene promoter (P-SV40), and uses one or more bovine growth hormone gene-derived polyadenylation signal (BGH pA). Positions of core ORFs with the inserted polyepitope-encoding sequence is indicated by arrows. Nucleotide positions are indicated according to the sequence of the HBV genotype D ayw subtype. Position 0 corresponds to the EcoR1 site and position 1981 corresponds to the 3'-end of the polyadenylation signal for mRNA in the HBV genome.

FIGS. 12A-12D show the expression of rHBV and chimeric antigenic protein.

FIG. 12A: Western blot analysis of cell lysate obtained after transfection of the HepG2 cell line (ATCC number HB-8065) with pFLAG-PCNA or prHBV1.3 plasmids. The molecular weights of proliferating cell nuclear antigen (PCNA) fused with Flag (lane 1; control) and rHBc (lane 2) are estimated according to molecular weight markers (kilodaltons (KDa)).

FIG. 12B: Immunofluorescence staining of HepG2 cells transfected with prHBV1.3 plasmid using anti-HBs (upper panel) or anti-FLAG antibodies (lower panel). DAPI stained nuclei are in blue.

FIG. 12C: Antibody labeling (anti-HBs, left panel and anti-FLAG, right panel) and immunofluorescence staining on liver sections taken from mice (ATCC number HB-8065) four days following hydrodynamic injection of prHBV1.3.

FIG. 12D: Quantification of HBsAg particles containing HBV-L protein by sandwich ELISA. PreS1-specific monoclonal antibodies (5a91 and 18-7) were used as capture antibodies to detect L protein in culture supernatants of Huh-7 cells transfected with two different ratios of prHBV1.3 (rHBV) and pMAS-C (CORE) plasmids or with a control plasmid pIRES-EGFP (EGFP). Results are expressed as optical densities (OD) at 450 nm, by ELISA.

FIGS. 13A-13D show the encapsidation rHBV genome by wild type core protein.

FIG. 13A: Viral DNA detected by Southern blot assay with an HBV-specific probe in the cell culture supernatants of Huh 7 cells transfected with two different concentrations of prHBV1.3 (lanes 1, 3) or prHBV1.3/HBc plasmids (lanes 2, 4). Wild type HBV DNA was extracted from the HepAD38 cell line as a control (lane 5). Bands corresponding to relaxed circular (RC), double-stranded linear (DSL) and single-stranded (SS) HBV DNA are indicated. M: molecular weight markers (Kb). HBc+ indicates expression of capsid protein by the vector used in transfection experiments.

FIG. 13B: ELISA assay results comparing HbsAg (left) and LHBsAg (right) production in culture medium (from day 3-5) of Huh 7 cells transfected with either prHBV1.3 (empty columns) or prHBV1.3/HBc (grey columns). HBsAg (ng/ml) was quantified by Monolisa detection kit (Bio-Rad, Hercules, Calif.). LHBsAg production was expressed as optical densities (OD) at 450 nm.

FIG. 13C: Southern blot assay of the viral DNA in Huh 7 cells 3 days after cotransfection with payw 1.2 and prHBV 1.3. The concentrations of each are shown in the table below the blot.

FIG. 13D: Detection of viral DNA by PCR in sera of C57/BL6 mice four days after hydrodynamic injection of prHBV1.3 with either pMAS-C (lanes 1-3) or pCMV-bGal (lanes 4-6). pFC80 plasmid was used as a positive control (lane 7).

FIG. 14A: ELIspot assay performed on splenocytes from ten HLA-A2/DR1 transgenic mice taken 15 days after one intramuscular injection of pCMV-rHBe. Each bar represents the number of IFN-γ-secreting T cells per million splenocytes for each individual mouse. Peptides used to stimulate splenocytes ex vivo are derived from HIV gag (HIV-G), Influenza matrix (Flu-M), EBV-BMLF1 (EBV-B), HBV capsid (HBc/18-27), and HBV envelope (HBs 5) proteins. PADRE is a promiscuous HLA-class II-binding peptide.

FIG. 14B: FACS analysis of Flu-specific T cells from a non-immunized mouse (left panel) and from a representative HLA-A2/DR1 transgenic mouse (right panel) taken 15 days after one intramuscular injection of pCMV-rHBe. Spleen cells were stained with an APC-labeled anti-CD8 antibody and a HLA-A2-pentamer carrying the Flu peptide. Flu-specific T cells represent around 10% of CD8 T cells from the spleen (red circle).

FIG. 14C: Proliferative response of splenocytes from pCMV-rHBc-immunized HLA-A2/DR1 transgenic mice following in vitro stimulation with PADRE peptide. Responses are expressed as the proliferation index. The dotted line corresponds to the mean value of the stimulation index. SI>2 is considered positive.

FIG. 15A: The protocol for active immunization includes priming of T cell responses at day 0 (D0) by intramuscular injection of pCMV-rHBc. At day 15 (D15), mice were injected via the hydrodynamic route with either prHBV1.3 or control pCMV-βGal plasmid. Lymphocytes from spleen and liver were collected at day 22 (D22) for FACS analysis.

FIG. 15B: FACS analysis of intrahepatic lymphocytes stained with anti-CD3-PerCP and anti-CD8-APC antibodies (upper panels), and with PE-labeled Flu-specific tetramer and APC-labeled anti-CD8 (lower panels). Lymphocytes were prepared from non-immunized mice (B1, left panels), mice receiving pCMVrHBc priming/pCMVβGal hydrodynamic injection (B2, middle panels), and mice receiving pCMVrHBc priming/prHBV1.3 hydrodynamic injection (B3, right panels). The percentages of CD8$^+$ (circle) and CD4$^+$ (square) T cells among the splenocytes are indicated.

FIG. 15C: Analysis of intrahepatic lymphocytes from three groups of mice. The first group received pCMVrHBc priming/pCMVβGal hydrodynamic injection (empty bars, n=5); the second group received pCMVrHBc priming/prHBV1.3 hydrodynamic injection (dotted bars, n=6); the third group were injected twice with pCMVrHBc via the intramuscular route (grey bars, n=3). Results are given as the mean±SEM percentage of CD8$^+$, CD4$^+$ and Flu-specific T cells in the total lymphocyte population.

FIG. 15D: Analysis of the intrasplenic lymphocytes from the mice described in FIG. 15C.

FIGS. 16A-16F show an analysis of liver-infiltrating lymphocytes.

FIG. 16A: Histological analysis of liver sections taken four days after hydrodynamic injection. Hematoxylin/eosin staining of liver sections from a representative HLA-A2/DR1 mouse receiving pCMVrHBc priming/pCMVβGal hydrodynamic injection (left panel, 100×); and from a representative mouse receiving pCMVrHBc priming/prHBV1.3 hydrodynamic injection (middle panel, 100×). The right panel shows an area from the middle panel at a magnification of 200×. Cell clusters of inflammatory foci are indicated with frames. Arrows indicate cells undergoing degeneration.

FIG. 16B: Phenotype of intrahepatic lymphocytes taken from a representative mouse after pCMVrHBc priming/prHBV1.3 hydrodynamic injection. CD8+ T cells were gated for analysis of Flu+ or Flu negative cells following Flu-pentamer labeling (left panel). Quantification of CD69+ and CD62L+ cells was done on pentamer positive (middle panel) and pentamer negative (right panel) CD8 T cells.

FIG. 16C: Functional profile of CD3+CD8+ intrahepatic T cells. Cells were analyzed for CD107, a surface marker, intracellular INFγ, and TNFα, following ex vivo stimulation with polyepitope-derived peptides (mix of three) (lower panel) or without stimulation (upper panel).

FIG. 16D: Immunostaining of HBsAg on liver sections taken four days after prHBV1.3 hydrodynamic injection from mice that were either primed by pCMVrHBc intramuscular injection (left panel) or unprimed (right panel) before hydrodynamic injection of prHBV1.3.

FIG. 16E: Mean level of HBsAg (ng/ml) in the sera of the mice of FIG. 16D with priming (empty columns) or without priming (grey columns), before hydrodynamic injection of prHBV1.3.

FIG. 16F: Mean level of transaminase (ALT mU/ml) in the sera of the mice following pCMV-rHBc priming/prHBV1.3 hydrodynamic injection (grey column, n=11), and of mice with pCMV-rHBc primin/pCMV-βGal hydrodynamic injection (empty column, n=4). Concanavalin A (ConA) injection was used as a positive control for ALT increase.

FIG. 17A: Protocol for active immunization in HBsAg/HLA-A2 transgenic mice.

FIG. 17B: Decrease in HBsAg in the sera of individual HBsAg/HLA-A2 transgenic mice after priming by intramuscular injection of pCMV-rHBc at week 0 (W0), followed by prHBV1.3 hydrodynamic injection two weeks later (W2). Mice were bled weekly and HBsAg (ng/ml) was quantified using a commercial ELISA.

FIG. 17C: The percentage of HBsAg decrease over eight weeks in the sera of mice receiving prHBV1.3 (filled bars) or pCMV-βGal (empty bars). HBsAg concentration at week 0 was set at 100% and the results are expressed as mean±SEM.

FIG. 18 shows sequence for prHBV-1.3-III (SEQ ID NO: 4) (polyepitope (polytope) sequence shadowed (SEQ ID NO: 5)).

FIG. 19 shows sequence for rHBe_III_(SEQ ID NO: 6) (the recombinant protein; polyepitope (polytope) sequence shadowed (SEQ ID NO: 7)).

FIG. 20 shows sequence for polytope III (SEQ ID NO: 8) (amino acids in small letters are flanking residues).

FIG. 21 shows sequence for polytope IV (SEQ ID NO: 9) (amino acids in small letters are flanking residues).

FIG. 22 shows sequence for prHBV-1.3-IV (SEQ ID NO: 10) (polyepitope (polytope) sequence shadowed (SEQ ID NO: 11)).

FIG. 23 shows sequence for rHBe_IV_(SEQ ID NO: 12) (the recombinant protein; polyepitope (polytope) sequence shadowed (SEQ ID NO: 13)).

FIG. 24 shows NCBI Accession Number: V01460 Hepatitis B virus (strain ayw) genome, DNA sequence (ACCESSION V01460 J02203 VERSION V01460.1 GI:62276, VRL 28 Jan. 2003) (SEQ ID NO: 14).

DETAILED DESCRIPTION OF THE INVENTION

Hepadnaviruses are small, enveloped hepatotropic DNA viruses. The prototype member of this family is the human hepatitis B virus (HBV). The hepadnaviral genome consists of a partially double-stranded, relaxed circular DNA, which has a compact organization employing widely overlapping open reading frames and regulatory sequences. HBV genome is precisely-organized by various cis- or trans-elements that are overlapping each other.

Figure 1:
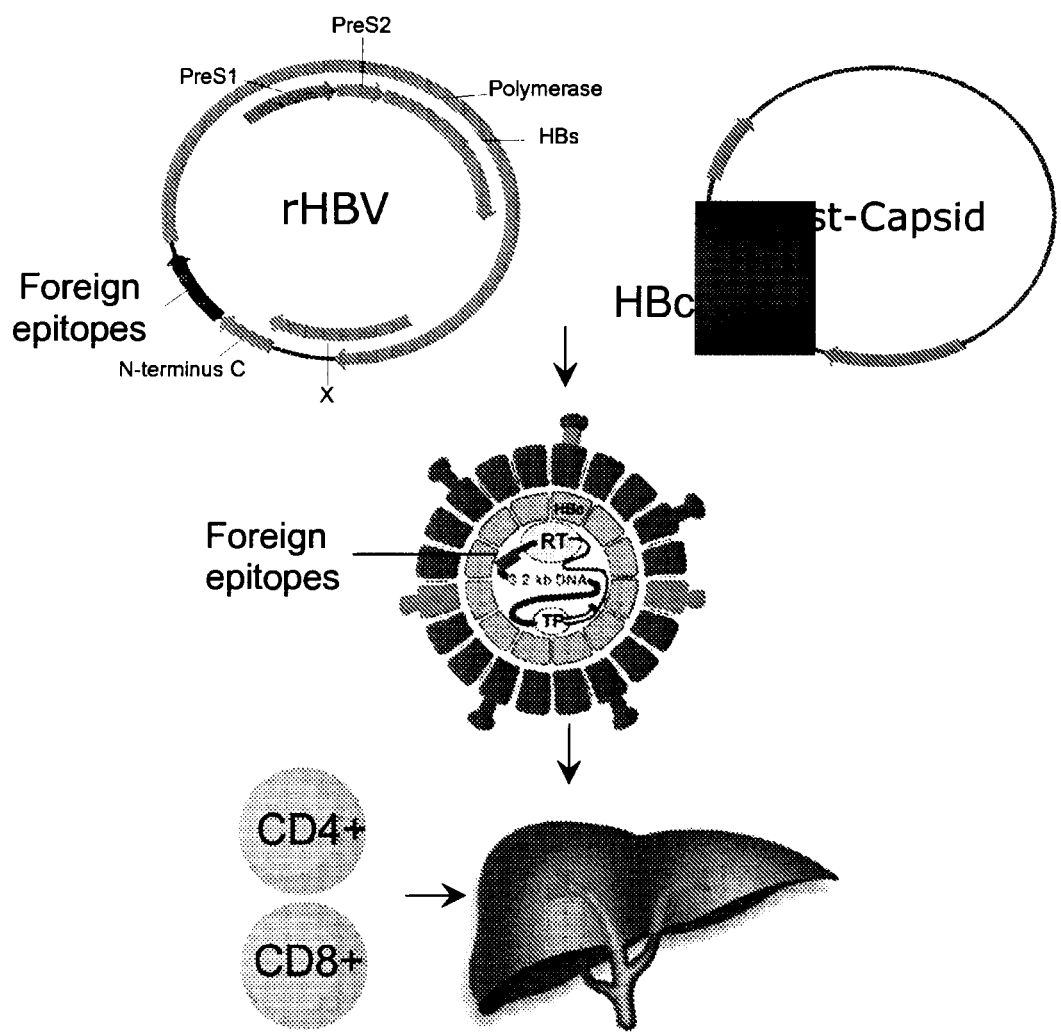
FIG. 1 is a schematic diagram of a recombinant vector designated rHBV complemented by a plasmid expressing HBc to form a pseudo-virus of the invention containing foreign epitopes, which can stimulate CD4+ and CD8+ responses to hepatocytes infected by the pseudo-virus.

By investigation of the viral genome, it was found that it might accommodate a piece of foreign sequence in the N-terminal part of the capsid-coding region to create a pseudo-virus that would maintain in hepatocytes, while the interrupted protein would be complemented in trans by wild type HBV during natural infection. (Gunther S., Piwon N., Jung A., Iwanska A., Schmitz H., Will H., 2000, Enhanced replication contributes to enrichment of hepatitis B virus with a deletion in the core gene, Virology 273:286-99). Thus, recombinant HBV would act as a targeting vector with liver-tropism for gene delivery (see FIG. 1).

Thus, this invention provides a vector derived from the hepatitis virus genome. The hepatitis virus genome was modified in order to express foreign epitopes fused within the N-terminal part of the hepatitis virus capsid protein. The resulting virus is replication defective. This recombinant, replication defective, hepatitis virus co-maintains in the liver of hepatitis virus-infected individuals through wild type capsid complementation. Infection with this recombinant virus leads to expression and presentation of foreign epitopes at the surface of hepatocytes. These epitopes presented in association with MHC molecules are the target of the host T-cell immune response. Therefore, only hepatitis virus-infected hepatocytes that allow replication of the recombinant hepatitis virus vector will be the target of the immune response and cured. The invention exploits the pre-existing immunity against foreign epitopes, for example from common pathogens, such as Flu. Hepatitis virus is cleared through cytolytic or non-cytolytic mechanisms.

In patients, viral clearance can be quantified by measuring HBV DNA in sera using commercially available kits. Clearance in the liver can be quantified by measuring DNA in biopsy. Sero-conversion from HBeAg, which is a marker of viral replication, to anti-HBe antibodies can be used as a marker for viral elimination. Elimination of HBsAg from the sera and seroconversion to anti-HBs antibodies indicates the complete elimination of the virus.

This invention also provides a recombinant, replication competent hepatitis pseudo-virus based on the replication defective hepatitis virus of the invention. The pseudo-virus comprises the recombinant, replication defective, hepatitis virus of the invention complemented by HBc, wherein the pseudo-virus replicates in vitro in human hepatocytes.

More particularly, this invention provides a recombinant, replication defective, hepatitis virus comprising a hepatitis virus genome defective for the expression of hepatitis virus capsid protein (HBc), wherein the virus contains a nucleotide sequence of up to about 195 nucleotides encoding at least one immuno-dominant epitope of a pathogen, wherein the nucleotide sequence is located between nucleotide residue 1981 and nucleotide residue 2308 of the HBV ayw3 genome (numbering starts from the fourth nucleotide in the EcoRI site of the HBV genome, NCBI Accession No. V01460). This virus is referred to herein as "the recombinant, replication defective, hepatitis virus" of the invention.

The recombinant, replication defective, hepatitis virus of the invention is complemented in the infected cell by expression of HBc by the hepatitis virus infecting cell. The genome of the replication incompetent virus is completely enclosed within the capsid produced by the wild hepatitis virus infecting the cell. The complemented virus is referred to herein as "the hepatitis pseudo-virus".

This invention thus provides polynucleotides and expression vectors for the production of proteins, which assemble into pseudo-virus, and which are efficiently produced in host cells. It is thus possible to make self-assembling, recombinant, pseudo-virus with residues of a foreign peptide. This provides efficient monovalent, bivalent, and multivalent immunogenic compositions and therapeutic vaccines.

While the replication defective hepatitis virus and the hepatitis-pseudo-virus of the invention will be described in detail with reference to HBV, it will be understood that this invention is applicable to other hepatitis viruses, including Hepatitis A Virus (HAV) (Picornavirus); Hepatitis Delta Virus (HDV) (Deltavirus); Hepatitis C Virus (HCV) (Flavivirus); and Hepatitis E Virus (HV). Thus, as used herein, the term "hepatitis" includes hepatitis B and other hepatitis viruses. Hepatitis B is the preferred virus for use in practicing this invention. More generally, the invention is applicable to other viruses.

In practicing the invention using other hepatotrophic viruses, such as HCV, and more generally all viruses involved in persistent infection, the viral genome can be examined to identify an appropriate site for the insertion of foreign epitopes. For example, due to overlapping open reading frames encoding the structural and non-structural viral proteins of HBV, the only gene that can be targeted for epitope insertion is the nucleocapsid-encoding gene. However, other RNA or DNA viruses have different tolerances for genomic insertions. In addition, different viruses infect different tissues that can be targeted and destroyed by the induced T cell responses, without damaging other non-infected tissues.

The term "peptide" is generally understood in the art to refer to a small amino acid molecule, whereas the term "polypeptide" is generally understood to refer to a larger amino acid molecule. Both peptides and polypeptides are within the scope of this invention. Thus, for example, the foreign sequences can be either a peptide or a polypeptide. The terms are used interchangeably herein.

In one aspect, the invention provides hepatitis pseudo-viruses comprising epitope-bearing portions of foreign peptide(s) or polypeptide(s). As used herein, the terms foreign peptides and polypeptides or epitopes means a peptide or polypeptide or an epitope not found in wild-type hepatitis virus.

The epitopes are immunogenic or antigenic epitopes of the foreign peptides or polypeptides. An "immunogenic epitope" is defined as a part of a protein that elicits a humoral or cellular response in vivo when the whole polypeptide, or fragment thereof, is the immunogen. A region of a polypeptide to which an antibody can bind is defined as an "antigenic determinant" or "antigenic epitope". The antigenic epitope can also elicit a humoral or cellular response in vivo when employed in the hepatitis pseudo-virus. Thus, included in the present invention are hepatitis pseudo-viruses containing both immunogenic epitopes and antigenic epitopes, or either one of them. Foreign peptides or polypeptides comprising immunogenic or antigenic epitopes are at least 8 amino acids residues in length for epitopes binding to MHC class I molecules, and at least 12 amino acids in length for epitopes binding to MHC class II molecules (cellular response). B cell (humoral response) epitopes are at least four amino acids in length.

In some embodiments, the foreign peptide or polypeptide can contain from about 8 to about 140 amino acid residues, preferably from about 20 to about 140 amino acid residues, especially from about 60 to about 140 amino acid residues. In the case of HBV, it can contain up to about 68 amino acids. In one embodiment, in the case of HBV, the foreign peptide or polypeptide contains 68 amino acids. In another embodiment, it contains about 65 amino acids. Flanking residues on either the N-terminal, C-terminal, or both N- and C-terminal ends may be added to the foreign peptide or polypeptide to generate the hepatitis pseudo-viruses.

The foreign peptide or polypeptide can also be derived from any number of foreign proteins. The foreign peptide or polypeptide can be derived from any protein of any plant, animal, bacterial, viral, or parasitic organism.

In one embodiment, the foreign peptide or polypeptide can be derived from a polypeptide of a pathogen. The term "pathogen" as used herein, means a specific causative agent of disease, and may include, for example, any bacteria, virus, or parasite.

The term "disease" as used herein, means an interruption, cessation, or disorder of body function, system, or organ. Typical diseases include infectious diseases. For example, the foreign peptide or polypeptide can be from the immunogenic proteins of an RNA virus, such as HIV-1, HIV-2, SIV, HCV, Ebola virus, Marburg virus, HTLV-I, and HTLV-II. Specific examples are the structural or NS1 proteins of Dengue virus; the G1, G2, or N proteins of Hantaan virus; the HA proteins of Influenza A virus; the Env proteins of Friend murine leukemia virus; the Env proteins of HTLV-1 virus; the preM, E, NS1, or NS2A proteins of Japanese encephalitis virus; the N or G proteins of Lassa virus; the G or NP proteins of lymphocytic choriomeningitis virus; the HA or F proteins of measles virus; the F or HN proteins of parainfluenza 3 virus; the F or HN proteins of parainfluenza SV5 virus; the G proteins of Rabies virus; the F or G proteins of respiratory syncytial virus; the HA or F proteins of Rinderpest; or the G proteins of vesicular stomatitis virus. These are just some of the possibilities and do not represent an exhaustive or restricted list.

The foreign peptide or polypeptide can also be derived from the immunogenic proteins of a DNA virus, such as gp89 of cytomegalovirus; gp340 of Epstein-Barr; gp13 or 14 of equine herpesvirus; gB of herpes simplex 1; gD of Herpes simplex 1; gD of herpes simplex 2; or gp50 of pseudorabies. Once again, these are just some of the possibilities and do not represent an exhaustive or restricted list.

Further, the foreign peptide or polypeptide can be derived from the immunogenic proteins of bacteria, such as Streptococci A M6 antigens, or tumor antigens, such as human melanoma p97, rat Neu oncogene p185, human epithelial tumor ETA, or human papilloma virus antigens. Again, these do not comprise an exhaustive or restricted list.

In an embodiment of this invention, the foreign peptide or polypeptide is derived from a human immunodeficiency virus. Following are HIV-1 epitopes that can be employed in designing the foreign peptide or polypeptide.

| | | | |
|---|---|---|---|
| GAG | P17 (77-85) | SLYNTVATL (S9L) | (SEQ ID NO: 15) |
| | P24 (19-27) | TLNAWVKW (T9V) | (SEQ ID NO: 16) |
| POL | (79-88) | LLDTGADDTV (L10V) | (SEQ ID NO: 17) |
| | (263-273) | VLDVGDAYFSV (V11V) | (SEQ ID NO: 18) |
| | (334-342) | VIYQYMDDL (V9L) | (SEQ ID NO: 19) |
| | (464-472) | ILKEPVHGV (I9V) | (SEQ ID NO: 20) |
| | (576-584) | PLVKLWYQL (P9L) | (SEQ ID NO: 21) |
| | (669-679) | ESELVNQIIEQ (E11Q) | (SEQ ID NO: 22) |
| | (671-680) | ELVNQIIEQL (E10L) | (SEQ ID NO: 23) |
| | (956-964) | LLWKGEGAV (L9V) | (SEQ ID NO: 24) |
| ENV | Gp41 (260-268) | RLRDLLLIV (R9V) | (SEQ ID NO: 25) |
| NEF | (188-196) | AFHHVAREL (A9L) | (SEQ ID NO: 26) |

Numbering is based on the amino acid sequence of the HIV-1 WEAU clone 1.60 (Genbank accession No. U21135). The WEAU sequence may not be always identical to that of the reactive peptide and simply indicates its location in the viral proteins.

The foreign peptide or polypeptide can comprise one epitope or a multiplicity of epitopes linked to each other. In addition, it will be understood that the hepatitis pseudo-virus of the invention can contain multiple epitopes of one or more origins, such as epitopes from different immunogenic proteins of the same pathogen. It will also be understood that the hepatitis pseudo-virus can contain one or more epitopes from different origins, such as epitopes from different pathogens. In addition, mixtures of hepatitis pseudo-viruses having different epitopes in different particles are contemplated by this invention.

The proteins containing the foreign sequence can be exposed on the surface of cells infected with the wild-type virus. The resulting exposed epitopes provide excellent configurational mimics of the epitopes as they exist, for example, in pathogens, such as other infectious viruses. For these reasons, the virus-infected cells are suitable for exploitation as carriers for foreign peptides or polypeptides, such as protective determinants of etiologic agents, via the replication defective, hepatitis virus and the resulting hepatitis pseudo-virus of the invention.

Recombinant expression vectors containing a nucleic acid encoding proteins of the pseudo-viruses of the invention can be prepared using well known methods. The expression vectors include the sequence encoding the foreign peptide or polypeptide operably linked to suitable transcriptional or translational regulatory nucleotide sequences, such as those derived from a mammalian, viral, or insect gene. A transcriptional or translational regulatory nucleotide sequence is operably linked if the nucleotide sequence controls the transcription or translation of another coding DNA sequence. Examples of regulatory sequences include transcriptional promoters, operators, or enhancers, an mRNA ribosomal binding site, tissue specific promoters and post-transcriptional regulatory elements (PRE), and appropriate sequences that control transcription and translation initiation or termination. The ability to replicate in the desired host cells, usually conferred by an origin of replication, and a selection gene by which transformants are identified, may additionally be incorporated into the expression vector.

Among eukaryotic vectors for use in the preparation of vectors of the invention are pWLNEO, pSV2CAT, pOG44, pXT1, and pSG available from Stratagene (La Jolla, Calif.); and pSVK3, pBPV, pMSG, and pSVL available from Pharmacia (Piscataway, N.J.). Other suitable vectors will be readily apparent to the skilled artisan.

Among vectors for use in the preparation of vector of the invention, non-integrative eucaryotic vectors are not only useful, but integrative/transformant vectors (i.e. vectors that integrate a part of their nucleic acid material in the genome of the eukaryotic host cell) can also be employed. Typical of these vectors are lentiviral vector Trips, adenovirus, and yeast integrative vectors.

In a preferred embodiment, the expression vectors of the invention include at least one selectable marker. Such markers include, for example, dihydrofolate reductase, G418, ampicilin or neomycin resistance for eukaryotic cell culture.

Any strong promoter known to those skilled in the art can be used for driving expression. Suitable promoters include adenoviral promoters, such as the adenoviral major late promoter; heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the β-actin promoter; and human growth hormone promoters. The promoter also can be a native promoter from a hepatitis virus, such as HBV.

In vivo delivery of the recombinant viruses of the invention requires production of viral stocks. In the case of hepatitis virus, this can be achieved by using a hepatocytic cell line expressing wild type hepatic virus capsid. A method for the production of viral stocks is described in Gunther S. et al., Virology, 273:286-99 (2000).

Suitable host cells for expression of pseudo-virus include higher eukaryotic cells. For example, in the case of hepatitis virus, differentiated hepatocytes are required for HBV, HCV, and HDV replication. Appropriate cloning and expression vectors for use with plant, fungal, yeast, and mammalian cellular hosts are described, for example, in Pouwels et al. Cloning Vectors: A Laboratory Manual, Elsevier, N.Y., (1985). Representative examples of appropriate hosts include, but are not limited to, fungal cells, such as yeast cells; insect cells, such as *Drosophila* S2 and *Spodoptera* Sf9 cells; animal cells, such as CHO, COS, 293, and Bowes melanoma cells; and plant cells. Appropriate culture mediums and conditions for the above-described host cells are known in the art.

Introduction of the vector of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986).

In another aspect, the invention is directed to an in vitro method for producing pseudo virus, comprising culturing in vitro, in a suitable culture medium, a cell incorporating an expression vector of the invention and collecting in the culture medium pseudo-virus produced by these cells.

Therefore, the invention is also concerned with cells, such as recombinant eucaryotic cells, infected, transformed, or transfected by a polynucleotide or vector of the invention for expressing the pseudo-virus. Methods for producing such cells and methods for using these cells in the production of recombinant viruses are well known in the art. The pseudo-virus can be recovered and purified from recombinant cell cultures by well-known methods, including ammonium sulfate precipitation, anion or cation exchange chromatography, phosphocellulose chromatography, hydrophobic interaction chromatography, affinity chromatography, hydroxyapatite chromatography, and lectin or heparin chromatography.

While this invention relates to hepatitis pseudo-virus carrying one or more (poly)epitopes of foreign peptides or polypeptides, this invention contemplates the use of (poly) epitopes that have been optimized for incorporation in hepatitis pseudo-virus. The (poly)epitope nucleic and amino acid sequences can be modified in view of increasing the overall hydrophilicity of the (poly)epitope and ensuring a modified processing of epitopes. Epitopes in a polyepitope can be permutated in order to obtain the best hydrophilic profile. Hydrophilic spacers can be added to counterbalance the generally hydrophobic epitopes.

The polypeptides or polynucleotides of this invention can be in isolated or purified form. The terms "isolated" or "purified", as used in the context of this specification to define purity, means that the protein, polypeptide, or polynucleotide is substantially free of other proteins of natural or endogenous origin and contains less than about 1% by mass of protein or polynucleotide, of other contaminants residual of production processes.

In practicing the method of the invention, the replication defective virus is administered to a host using one of the modes of administration commonly employed for administering drugs to humans and other animals. Thus, for example, the replication defective virus can be administered to the host by the oral route or parenterally, such as by intravenous or intramuscular injection. Other modes of administration can also be employed, such as intrasplenic, intrahepatic, perfusion, intradermal, and mucosal routes. Preferably, the replication defective virus of the invention is administered according to the natural route of infection of the virus. For purposes of injection, the replication defective virus as described above can be prepared in the form of solutions, suspensions, or emulsions in vehicles conventionally employed for this purpose.

Accordingly, the invention contemplates compositions comprising the recombinant replication defective virus of the invention in combination with a pharmaceutically acceptable carrier. The invention also contemplates a vaccine comprising such compositions. The vaccines of the invention may be administered to a patient persistently infected with a virus in order to stimulate a T cell response against cells infected with the virus. Thus, the invention also contemplates the use of the recombinant replication defective viruses of the invention for the preparation of a medicament for treating a patient persistently infected with the wild type virus. The invention also contemplates a method for targeting the expression of an epitope in a cell infected with a virus by providing to the cell the recombinant replication defective virus of the invention.

It will be understood that the replication defective viruses of the invention can be used in combination with other microorganism antigens, antibodies, or mitogens or other prophylactic or therapeutic substances. For example, mixtures of different parasite antigens, antibodies, or mitogens or mixtures of different viral or bacterial antigens, antibodies, or mitogens can be employed in the method of the invention. Similarly, mixtures of different replication defective viruses can be employed in the same composition. The replication defective viruses can also be combined with other vaccinating agents, such as immunodominant, immunopathological, and immunoprotective epitope-based vaccines, or inactivated attenuated or subunit vaccines.

The replication defective viruses of the invention are employed in an effective amount sufficient to provide an adequate concentration to clear virus in infected cells. The amount of the replication defective hepatitis viruses thus depends upon absorption, distribution, and clearance by the host. Of course, the effectiveness of the replication defective hepatitis viruses is dose related. The dosage of the replication defective viruses should be sufficient to produce a minimal detectable effect, but the dosage preferably should be less than the dose that activates a non-specific polyclonal lymphocyte response.

The dosage of the replication defective viruses of the invention administered to the host can be varied over wide limits. The viruses can be administered in the minimum quantity, which is therapeutically effective, and the dosage can be increased as desired up the maximum dosage tolerated by the patient. The replication defective viruses can be administered as a relatively high amount, followed by lower maintenance dose, or the viruses can be administered in uniform dosages.

The dosage and the frequency of administration will vary with the replication defective viruses employed in the method of the invention. The amount administered to a human can vary from about 50 ng per Kg of body weight to about 1 μg per Kg of body weight, preferably about 100 ng per Kg of body weight to about 500 ng per Kg of body weight. For chimpanzee infection, $2 \times 10^7$ to $5 \times 10^7$ HBV genome equivalents (which corresponds to about 35-90 pg DNA) are required (Guidotti L. G., et al., Science, 284:825-29 (1999)) This corresponds to 0.7 to 1.8 pg/Kg of body weight. Optimum amounts can be determined with a minimum of experimentation using conventional dose-response analytical techniques or by scaling up from studies based on animal models of disease.

The term "about" as used herein in describing dosage ranges means an amount that has the same effect as the numerically stated amount as indicated by clearance of chronic viral infection in the host to which the replication defective viruses are administered, with an absence or reduction in the host of determinants of pathogenicity, including an absence or reduction in persistence of the infectious virus in vivo, and/or the absence of pathogenesis and clinical disease, or diminished severity thereof, as compared to individuals not treated by the method of the invention.

The dose of the replication defective viruses of the invention is specified in relation to an adult of average size. Thus, it will be understood that the dosage can be adjusted by 20-25% for patients with a lighter or heavier build. Similarly, the dosage for a child can be adjusted using well known dosage calculation formulas.

The replication defective viruses of the invention can be used in therapy in the form of pills, tablets, lozenges, troches, capsules, suppositories, injectable in ingestible solutions, and the like in the treatment of hepatitis infection in humans and susceptible non-human primates and other vertebrate animals and mammals.

Appropriate pharmaceutically acceptable carriers, diluents, and adjuvants can be combined with the replication defective viruses described herein in order to prepare the pharmaceutical compositions for use in the treatment of pathological conditions in animals. The pharmaceutical compositions of this invention contain the replication defective viruses together with a solid or liquid pharmaceutically acceptable nontoxic carrier. Such pharmaceutical carriers can be sterile liquids, such as water and oils, including those of petroleum, animal, vegetable, or synthetic origin. Examples of suitable liquids are peanut oil, soybean oil, mineral oil, sesame oil, and the like. Water is a preferred carrier when the pharmaceutical composition is administered intravenously. Physiological solutions can also be employed as liquid carriers, particularly for injectable solutions.

Suitable pharmaceutical excipients include starch, glucose, lactose, sucrose, gelatin, malt, rice, flour, chalk, silica gel, magnesium carbonate, magnesium stearate, sodium stearate, glycerol monstearate, talc, sodium chloride, dried skim milk, glycerol, propylene glycol, water, ethanol, and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. The pharmaceutical compositions contain an effective therapeutic amount of the replication defective virus of the invention together with a suitable amount of carrier so as to provide the form for proper administration to the host.

The ability of the replication defective viruses of the invention to induce protection in a host can be enhanced by emulsification with an adjuvant, incorporation in a liposome, coupling to a suitable carrier, or by combinations of these techniques. For example, the replication defective viruses of the invention can be administered with a conventional adjuvant, such as aluminum phosphate and aluminum hydroxide gel. Similarly, the replication defective viruses can be bound to lipid membranes or incorporated in lipid membranes to form liposomes. The use of nonpyrogenic lipids free of nucleic acids and other extraneous matter can be employed for this purpose.

The host or patient can be an animal susceptible to infection by a virus, and is preferably a mammal. More preferably, the mammal is selected from the group consisting of a human, a dog, a cat, a bovine, a pig, and a horse. In an especially preferred embodiment, the mammal is a human.

Another aspect of the invention includes administering nucleic acids encoding the replication defective virus of the invention with or without carrier molecules to an individual. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids encoding replication defective virus of the invention, naked or encapsulated, directly to tissues and cells, especially muscle cells or keratinocytes, without the need for production of encoded proteins prior to administration. The technology is based on the ability of these nucleic acids to be taken up by cells of the recipient organism and expressed to produce a replication defective virus to which the recipient's immune system responds. Such nucleic acid vaccine technology includes, but is not limited to, delivery of expression vectors encoding a replication defective virus of the invention. Although the technology is termed "vaccine" it is equally applicable to immunogenic compositions that do not result in a completely curative response. Such partial-protection-inducing compositions and methods are encompassed within the present invention.

The present invention also encompasses delivery of replication defective virus as part of larger or more complex compositions. Included among these delivery systems are viruses, virus-like particles, or bacteria containing the nucleic acids encoding the replication defective virus of the invention. Also, complexes of the invention's nucleic acids and carrier molecules with cell permeabilizing compounds, such as liposomes, are included within the scope of the invention. Other compounds, such as molecular vectors (EP 696,191, Samain et al.) and delivery systems for nucleic acid vaccines are known to the skilled artisan and exemplified in, for example, WO 93/06223 and WO 90/11092, U.S. Pat. No. 5,580,859, and U.S. Pat. No. 5,589,466 (Vical patents), which are incorporated by reference herein, and can be made and used without undue or excessive experimentation.

During the replication cycle, HBV pregenomic RNA serves as the mRNA template for translation of the viral core and polymerase proteins. It is encapsidated together with the viral polymerase into a nucleocapsid consisting of around 200 subunits of the core protein. The viral envelope is densely packed with the large (L), middle (M) and predominantly small (S) viral envelope proteins. In addition to envelope proteins, the virus encodes a regulatory protein (X), all translated from subgenomic RNAs.

HBV infects only human and chimpanzees. As alternative animal models, the invention provides HBV- or HBsAg transgenic mice, which replicate or express HBV genes in the liver. Expression of the transgene from birth tolerizes dHBV-specific T cells responses in these animals.

The invention provides that hydrodynamic injection of rHBV to mimic gene expression in mouse livers circumvents the tolerization of dHBV-specific T cells response.

The invention also provides that, in HLA-transgenic mice, priming with a DNA vector encoding foreign HLA-A2 restricted epitopes activates T cell responses that subsequently localize to the liver of mice following hydrodynamic injection of recombinant HBV (rHBV). Since rHBV is expected to replicate only in hepatocytes bearing the wild type HBV and sharing the same mechanism in the viral cycle, the strong immune responses elicited by the foreign polyepitope dominates over the exhausted T cell responses present during natural HBV persistent infection.

A key question in the development of immunotherapeutic strategies against hepatitis B chronic infection is whether HBV-specific T cells can be functionally restored using vaccination or other immunomodulatory approaches. It is also important to assess whether vaccine or otherwise activated T cells can enter the liver and eliminate HBV-infected cells. In the current study, we used HBV as an immunotherapy vector to deliver a modified core protein fused with foreign immunogenic epitopes in liver cells. Following gene expression of this modified virus, functional epitope-specific T cells were attracted to liver in which they were able to control HBV gene expression in hepatocytes.

An ideal vector for gene therapy can target abnormal cells without harming healthy neighboring cells. The invention provides an artificial rHBV, with the core gene interrupted by insertion of a short sequence encoding immunodominant epitopes derived from common viruses. This modified virus was not competent for replication except in hepatocytes providing wild type viral capsids in trans. rHBV is, therefore, not expected to maintain in healthy hepatocytes, but only in cells from patients with chronic HBV replication. Once the natural HBV infection is eliminated, the rHBV pseudo-viral life is subsequently interrupted.

The 3.2-Kb HBV genome is highly compacted, with overlapping open reading frames (ORF) for structural genes and various regulatory elements. It is technically difficult to engineer this virus, mainly because of space limitation. The present invention provides that the foreign sequence in rHBV was inserted in a region located between polyadenylation signal for HBV mRNA and the start of the polymerase reading frame. No obvious cis-acting element has been found in this region that may participate to viral replication. However, a potential internal site for ribosome entry has been described. Thus, translation of the polymerase is a small probability event, with a mechanism of ribosome shunting along the messenger RNA. HBV polymerase functions in cis to find the epsilon signal in pgRNA and to initiate the viral replication. Therefore, the size of foreign insertion should be compatible with the translation of HBV polymerase. Interestingly, the rHBV in our study is similar to a naturally occurring HBV variant (DC-144), identified by Will H et al during fulminant hepatitis. This variant could produce 2- to 4.5-fold more progeny DNA than wild-type HBV when sufficiently complemented with wild-type core protein (Gunther S., Piwon N., Jung A., Iwanska A., Schmitz H., Will H., 2000, Enhanced replication contributes to enrichment of hepatitis B virus with a deletion in the core gene, Virology 273:286-99.) In addition, rHBV has a short viral genome that favors pgRNA packaging. It is thus expected that rHBV could dominate the cccDNA pool in the cell nucleus, leading to the inhibition of wild type HBV replication.

Increasing evidence suggests that the host immune response plays a critical role in determining the various outcomes of HBV infection. In particular, HBV-specific CD8 T-cell responses are believed to be of considerable importance in viral control and immune-mediated disease. However, during chronic infection, these responses are generally weak and narrowly focused. Virus-specific T cells from chronic patients rapidly become exhausted. T cell dysfunction has been attributed to high levels of persisting viral antigens. But in chronic patients immune responses to other pathogens remain intact. We therefore thought to design a novel therapeutic approach based on activation of non-HBV specific T cells that were further redirected to liver following rHBV injection.

Figure 2:
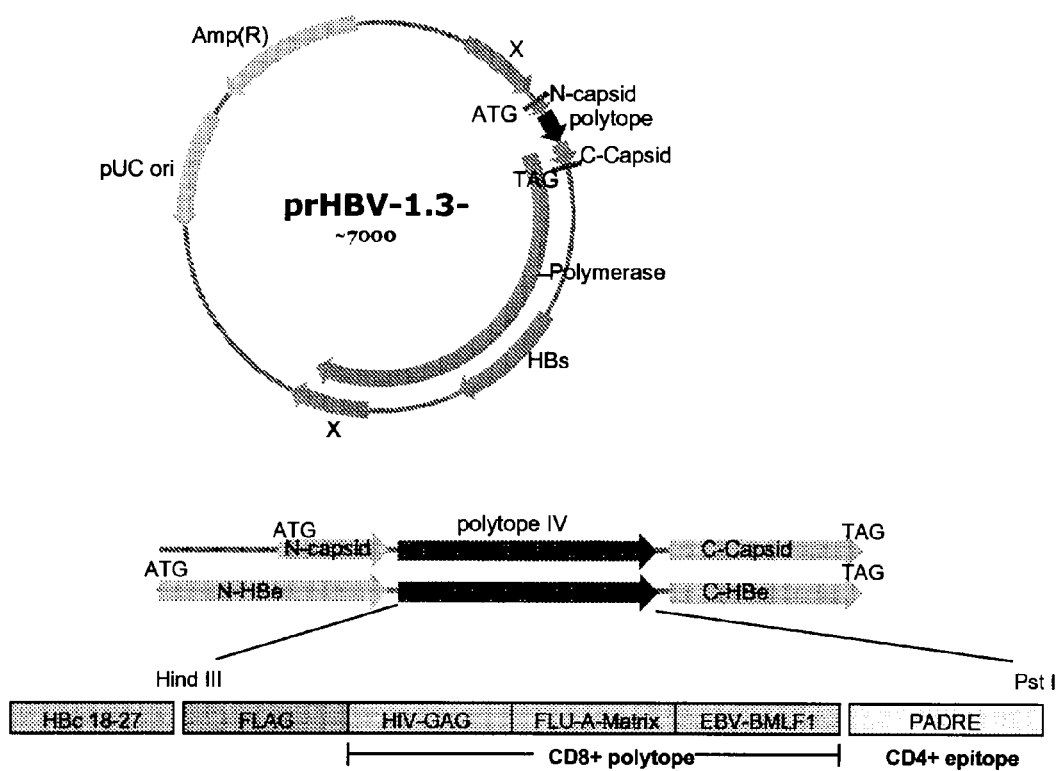
FIG. 2 depicts a construct designated prHBV-1.3-IV containing a polytope (polyepitope), as well as the construct designated polytope IV.

In summary, this invention provides a new approach to the design of a virus with a defective replication cycle, which can be rescued by wild type virus co-infection, and which expresses foreign antigenic epitopes that contribute to the elimination of virus infected cells and then to viral clearance. The vector of the invention, by expression of epitopes derived from common pathogens, by-passes existing tolerance of virus specific T cell responses. The vector will only replicate in virus infected cells.

In a particular embodiment, this invention provides a new approach to the design of a hepatitis virus with a defective replication cycle, which can be rescued by wild type hepatitis virus co-infection, and which expresses foreign antigenic epitopes that contribute to the elimination of hepatitis virus infected hepatocytes and then to viral clearance. The vector of the invention, by expression of epitopes derived from common pathogens, by-passes existing tolerance of hepatitis virus specific T cell responses. The vector will only replicate in hepatitis virus infected hepatocytes.

According to this invention, the foreign antigenic polyepitope can break or help to break the hepatitis immune tolerance. The induced T cell responses can silence, specifically or nonspecifically, hepatitis genes through non-cytolytic mechanisms. The recombinant hepatitis virus carrying the polyepitope can be tested for replication in hepatocytes of UPA-SCID mice reconstituted with human liver cells.

*E. coli* strains carrying the following plasmids were deposited at the Collection Nationale de Cultures de Microorganismes (C.N.C.M.), 25, rue du Docteur Roux, F-75724 Paris, Cedex 15, France, and assigned the following Accession Nos.:

| Plasmid | Accession No. |
|---|---|
| prHVB1.3-IV | CNCM I-3833 |
| pCMVrHbc-IV | CNCM I-3834 |
| prHVB1.3-III | CNCM I-3832 |

-continued

| Plasmid | Accession No. |
|---|---|
| pCMVrHBc | CNCM I-4077 |
| prHBV1.3 | CNCM I-4078 |
| prHBV1.3/HBc | CNCM I-4079 |

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges including either or both of the upper and lower limits of the range, unless specifically excluded from the stated range.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

It must be noted that, as used herein and in the appended claims, the singular forms "a", "or" and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about" unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperatures, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In vitro Assay for Recombinant HBV (rHBV) Replication

A polyepitope sequence was inserted into a 1.3 copy of HBV genome in the N-terminal part of the original capsid-encoding fragment to create the recombinant HBV (prHBV-1.3 and its derivatives-III or -IV, see FIG. 2). Co-transfection of prHBV1.3-III with the plasmid expressing capsid gene under a CMV promoter (pMAScore) to a liver cell line was carried out to initiate a replicating cycle mimicking the wild HBV replication in vitro (detection of cccDNA genome and other intermediate forms by Southern blot assay). Results are presented in FIG. 3A (detection of HBV genome in secreted viral particles by PCR).

Figure 3A:
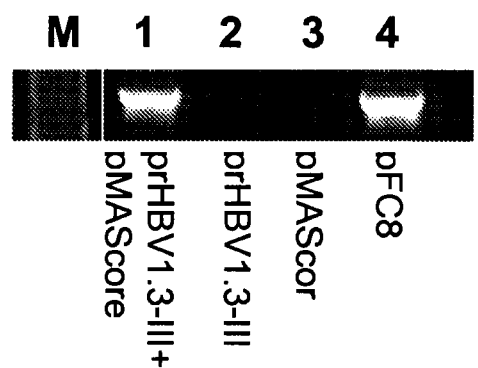
FIGS. 3A-3C depict the rescue of rHBV DNA from a human hepatocytic cell line co-transfected with prHBV 1.3-III and a plasmid expressing the capsid (PMAS core).

The human hepatocytic cell line Huh7 (Nakabayashi H., Taketa K., Mlyano K., Yamane T., Sato J., 1982, Growth of human hepatoma cell lines with differentiated functions in chemically defined medium, Cancer Res 42(9):3858-63) was transfected with prHBV1.3-III with or without pMAS-core, with pMAS-core alone, or with pFC80 (positive control, plasmid containing two HBV genomes in tandem). Supernatants were collected and viral particles were precipitated using PEG 8000. After a DNase treatment to remove the residual plasmid DNA, particles were lysed and HBV genome was PCR amplified (PCR primers on N part of core gene and middle of HBs-encoding gene). Alternatively, the primers may be on any part of the HBV genome, more particularly, before the S gene. The results are shown in FIG. 3A. The expected fragment is detected only after cotransfection of prHBV1.3 and pMAS-core, but not after transfection of either pMAS-core or prHBV1.3 alone.

Figure 3B:
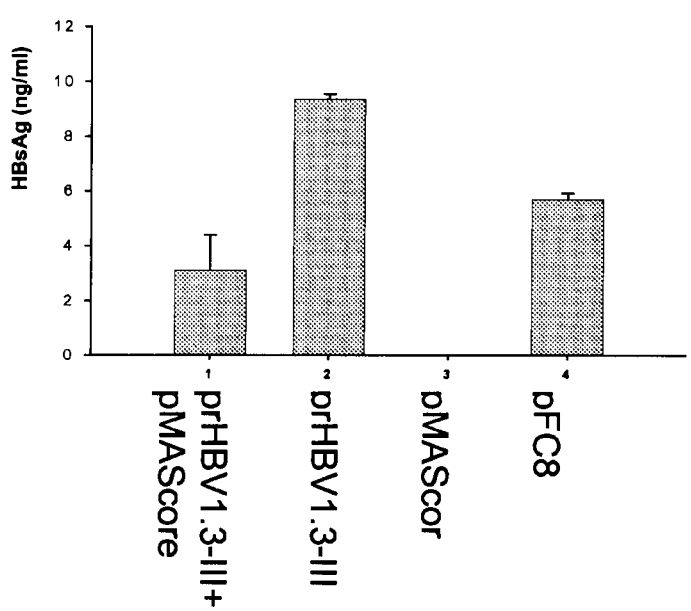

Hepatitis B surface antigen (HBsAg) was also detected in supernatant from cells cotransfected with prHBV1.3 and pMAS-core or transfected with pFC80, but not after transfection of pMAScore alone (see FIG. 3B).

Figure 3C:
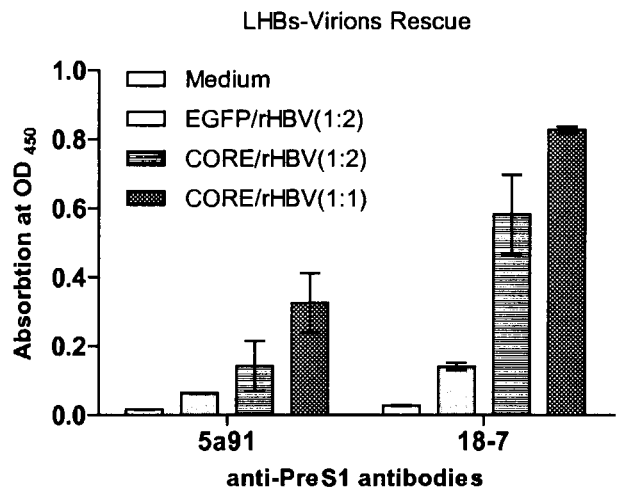
Figure 4:
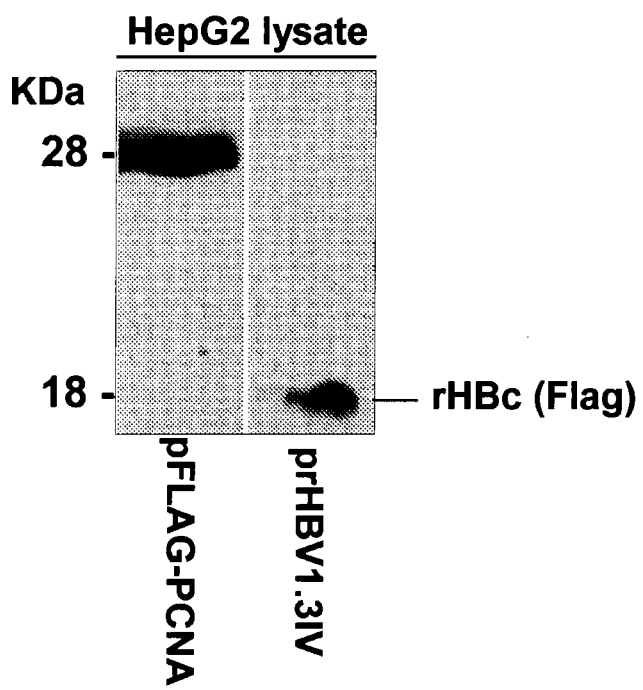
FIG. 4 shows the detection by Western blot of the recombinant antigen rHBe after transient transfection in HepG2 cell line (ATCC number HB-8065).
Figure 5A:
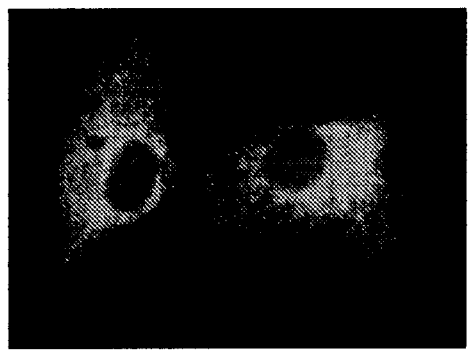
FIGS. 5A-5B show the detection by immunofluorescence staining with antibodies of the recombinant antigen rHBe after transient transfection in the HepG2 cell line. This is also shown in FIG. 12B.
Figure 5B:

To assess LHBs-virion rescue, two different ratios for co-transfection (1:1 and 1:2) and a control plasmid not expressing core but EGFP were used. After co-transfection of the prHBV1.3-III and pMAScore plasmids to the hepatocytic Huh 7 cell line, supernatants of transfected cells were collected. Viral particles containing the large HBV envelope protein (LHBs) were quantified by a specific ELISA using two monoclonal antibodies specific for the large HBV envelope protein (MoAb 5a91 and MoAb 18-7) as capture antibodies and a labeled anti-HBs MoAb for detection. Results are shown in FIG. 3C. This experiment shows that expression of core is required for efficient secretion of particles containing the LHBs in a dose-dependent way. LHBs is known to be localized on the surface of 42 nm HBV Dane particles.

Example 2

In Vivo Assay for rHBV Infection

An investigation is made to determine whether the in vitro produced rHBV virion could be infectious in vivo. Since there is no small animal model, a UPA transgenic mouse with transplanted human liver tissue can be useful. (Morosan S., et al., 2006, Liver-stage development of *Plasmodium falciparum*, in a humanized mouse model, J Infect Dis, 193:996-1004). For infection, a small stock of infectious rHBV is required. This will be obtained by first creating a stable HepG2 (ATCC number HB-8065) cell line expressing the rHBV genome constitutively and second by transducing this cell line with a lentiviral vector expressing the HBV core gene.

Example 3

Creation of a String of Immunodominant Epitopes

Figure 7:
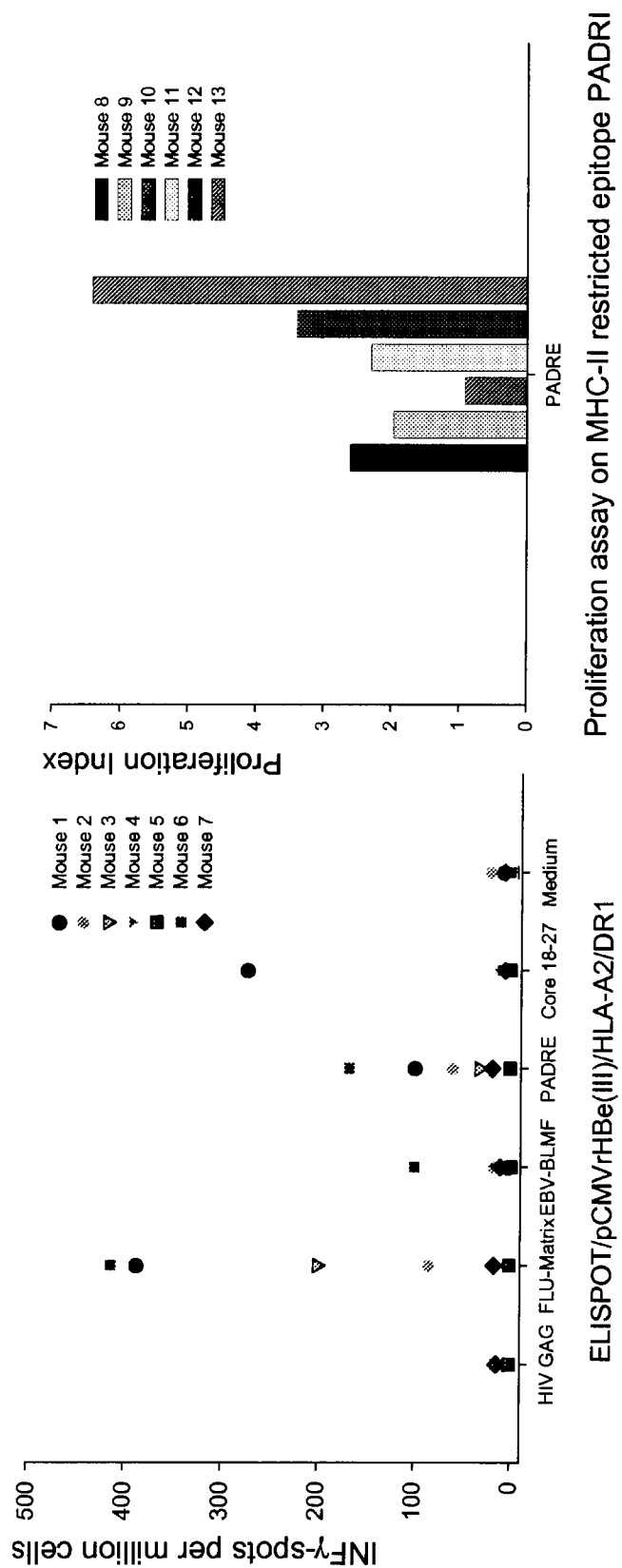
FIG. 7 shows cellular responses to the polyepitope in the rHBV genome of HLA-A2/DR1 Tg mice, detected by ELISPOT assay (left panel) and by a proliferation assay (right panel; this is also shown in FIG. 14C).

Based on the kn moter (pCMV-rHBe) was tested by intramuscular DNA immunization (two injections) in HLA-A2/DRB1*01 transgenic mice (Pajot et al., 2004). Specific T cell responses against the foreign epitopes were analyzed by proliferation and ELISPOT assays one week after the second injection in mice. The CD4 T-cell epitope PADRE activated IFN-γ-secreting cells (FIG. 7, left panel) and was able to induce proliferation of lymphocytes from immunized mice (FIG. 7, right panel).

Figure 8:
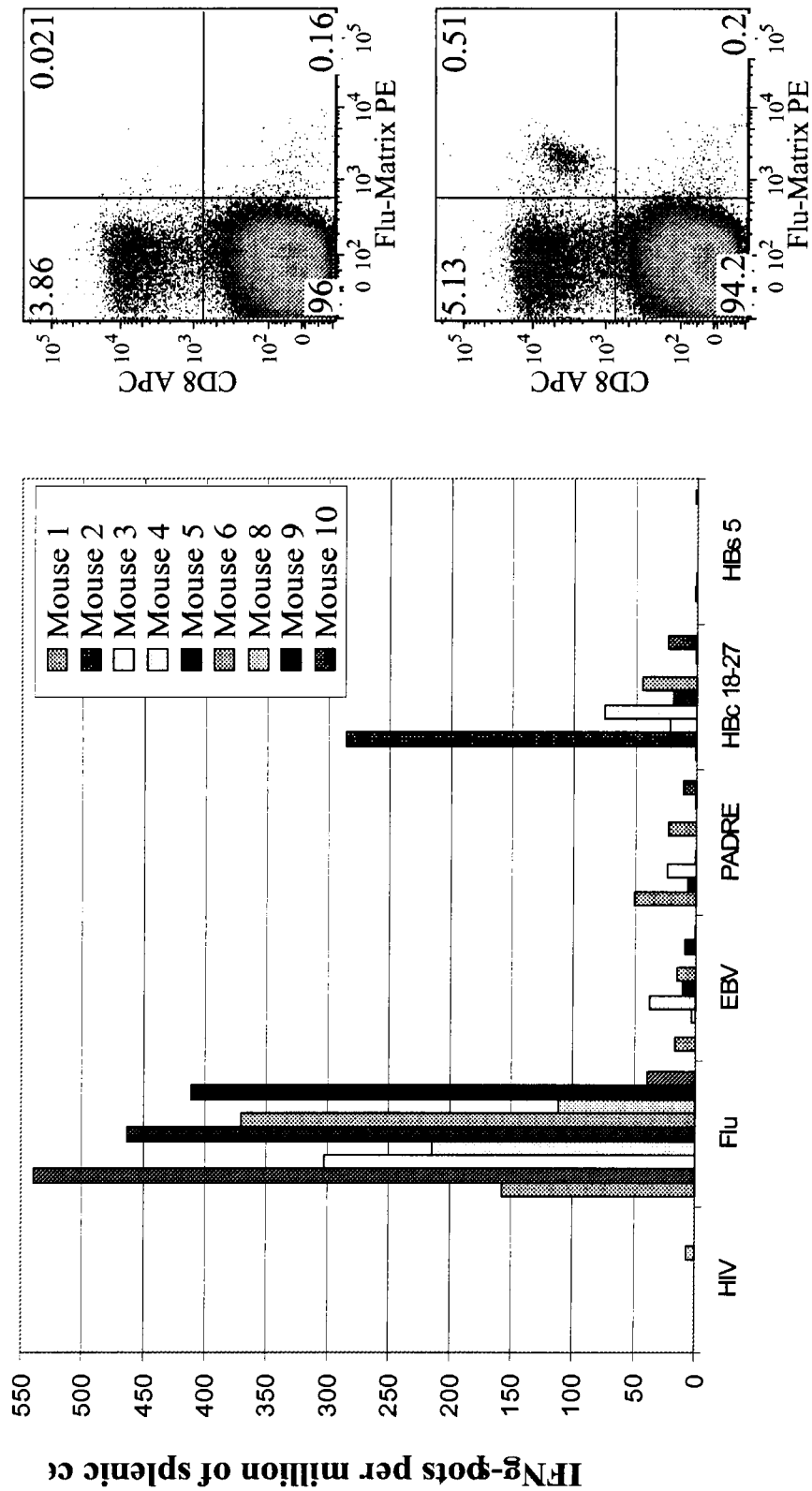
FIG. 8 shows the immune response of HLA-A2/DRB1 Tg mice immunized with pCMV-rHBe-IV. The left panel shows the immunodominant response to an epitope derived from influenza matrix protein. This is also shown in FIG. 14A. The right panel shows the detection in spleen cells of Flu-specific CD8+ T cells labeled with HLA-A2 tetramers carrying the Flu epitope in HLA-A2/DRB1 non-immunized (upper right) or immunized mice (lower right). This is also shown in FIG. 14B.

The Flu matrix-derived epitope was the most frequently recognized among the $CD8^+$ epitopes present in the polyepitope (4/6 responder mice). T cell responses to EBV and core-derived epitopes were found in only one mouse. The immunodominant response to the Flu-derived epitope probably resulted from competition between peptides for fixation to the HLA-A2 molecule. This was confirmed in a second experiment with 8/10 immunized mice having T cell responses to the Flu-derived epitope and only 3/10 to the HBc 18-27-derived HLA-A2 epitope (FIG. 8, left panel). Nevertheless the Gag- and EBV-derived epitopes activated T cells were detectable after one week in vitro stimulation of splenocytes with the corresponding peptides before IFN-γ ELISPOT assays.

T cell responses to the Flu matrix epitope was also quantified using a HLA-A2-tetramer carrying the Flu epitope in splenocytes from DNA-immunized mice (two injections of pCMV-rHBe). Flu-specific T cells represent around 10% of $CD8^+$ T cells from the spleen (FIG. 8, right panel).

Figure 9:
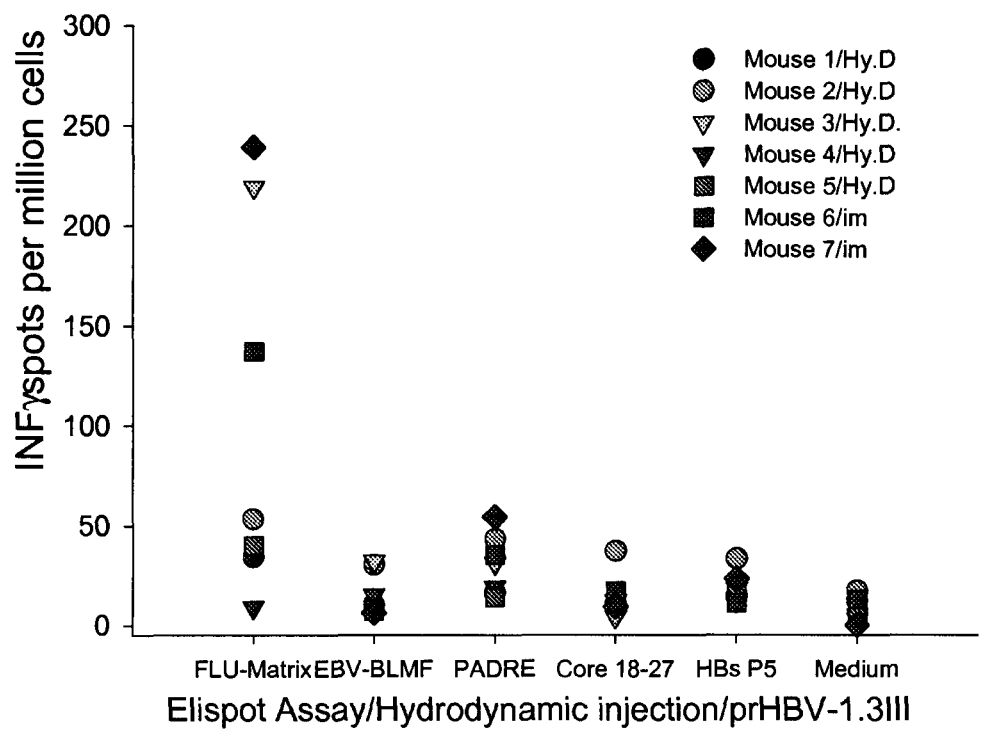
FIG. 9 shows the T cell response after hydrodynamic injection of prHBV-1.3III through the tail vein of the mouse (ELISPOT assay).

The immune response to the polyepitope expressed by the recombinant virus was also assessed after one hydrodynamic injection of prHBV1.3-III into HLA-A2/-DRB1*01 transgenic mice. IFN-γ ELISPOT assays were performed on splenocytes taken 16 days after hydrodynamic injection. T cells specific for the Flu matrix epitope were detected in 4 out of 5 mice (FIG. 9). In this experiment, 2 mice were immunized by intramuscular injection with prHBV1.3-III as control (mouse 6 and 7). Intravenous injection of recombinant HBV is less immunogenic than intramuscular injection. This could be related to the route of injection and to the expression of antigens in the liver, which is known to be a tolerogenic organ.

Example 7

Figure 10A:
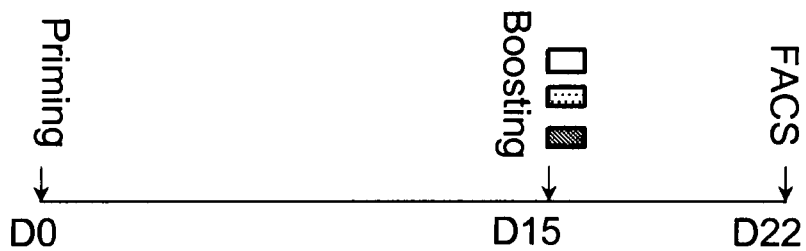
FIGS. 10A-10C show the T-cell responses to a polyepitope in vivo and the localization of Flu-specific T cells in the liver of mice after hydrodynamic injection of prHBV1.3. This is also shown in FIGS. 15A-15D.

Assessing T-Cell Response to Polyepitope In Vivo and Localization of Flu-Specific T-Cells Groups of HLA-A2/DRB1*01 mice (Pajot et al., 2004) were immunized intramuscularly with the plasmid pCMV-rHBe to prime T cell responses specific for foreign epitopes. Fifteen days after the priming, mice were injected by the hydrodynamic route with either prHBV 1.3 or pCMV-βGal (control plasmid), or by intramuscular injection of pCMV-rHBe. FIG. 10A presents a graphical depiction of the immunization time-line.

Figure 10B:
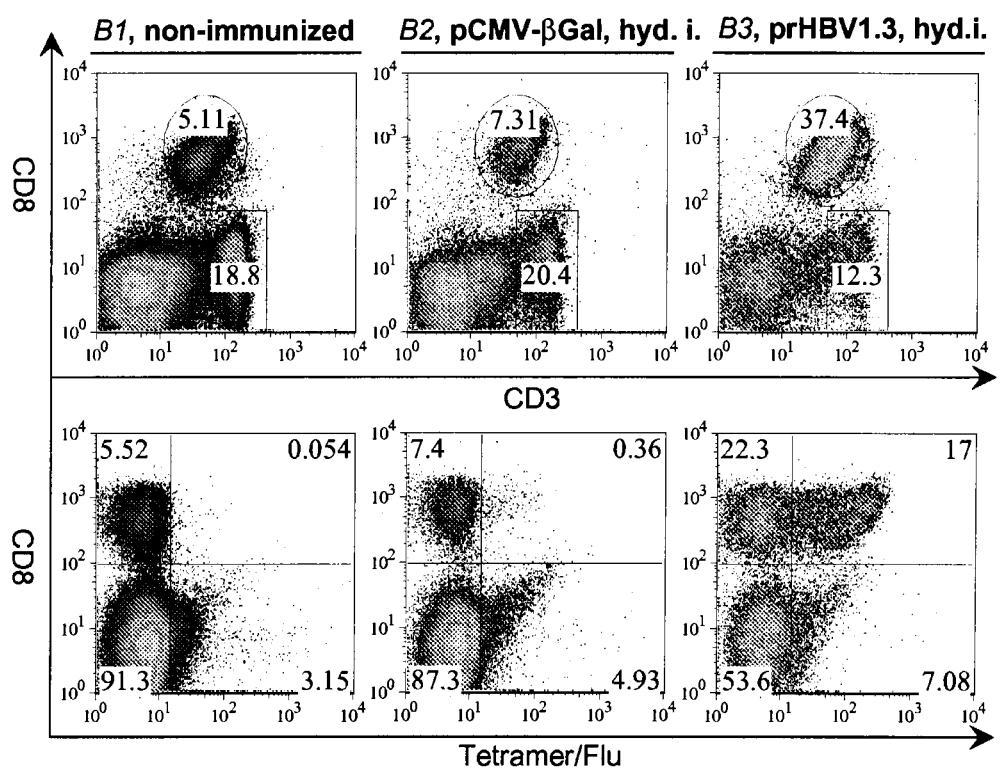

Liver infiltrating lymphocytes were prepared and stained with anti-CD8, anti-CD3 antibodies and with Flu-tetramers for FACS analysis. Non-immunized control mice were used as a control. Quantification of CD8 T cells was performed after staining with anti-CD8, anti-CD3 antibodies. $CD3^+$, $CD8^-$ cells were considered as $CD4^+$ T cells. FACS analysis showed that the number of $CD8^+$ T cells infiltrating liver was much higher in mice receiving prHBV1.3 (FIG. 10B, panel B3, 37.4%) compared to those receiving pCMV-βGal (FIG. 10B, panel B2, 7.31%) and non-injected mice (FIG. 10B, panel B1, 5.11%). Flu-specific T cells staining is shown on the lower panels for non-immunized mice, for mice receiving pCMV-βGal or for mice receiving prHBV1.3 by hydrodynamic injection. For mice receiving prHBV1.3, 17% of T cells are Flu-specific. These cells represent 42% of $CD8^+$ T cells. A comparable analysis was performed on spleen-derived lymphocytes.

Figure 10C:
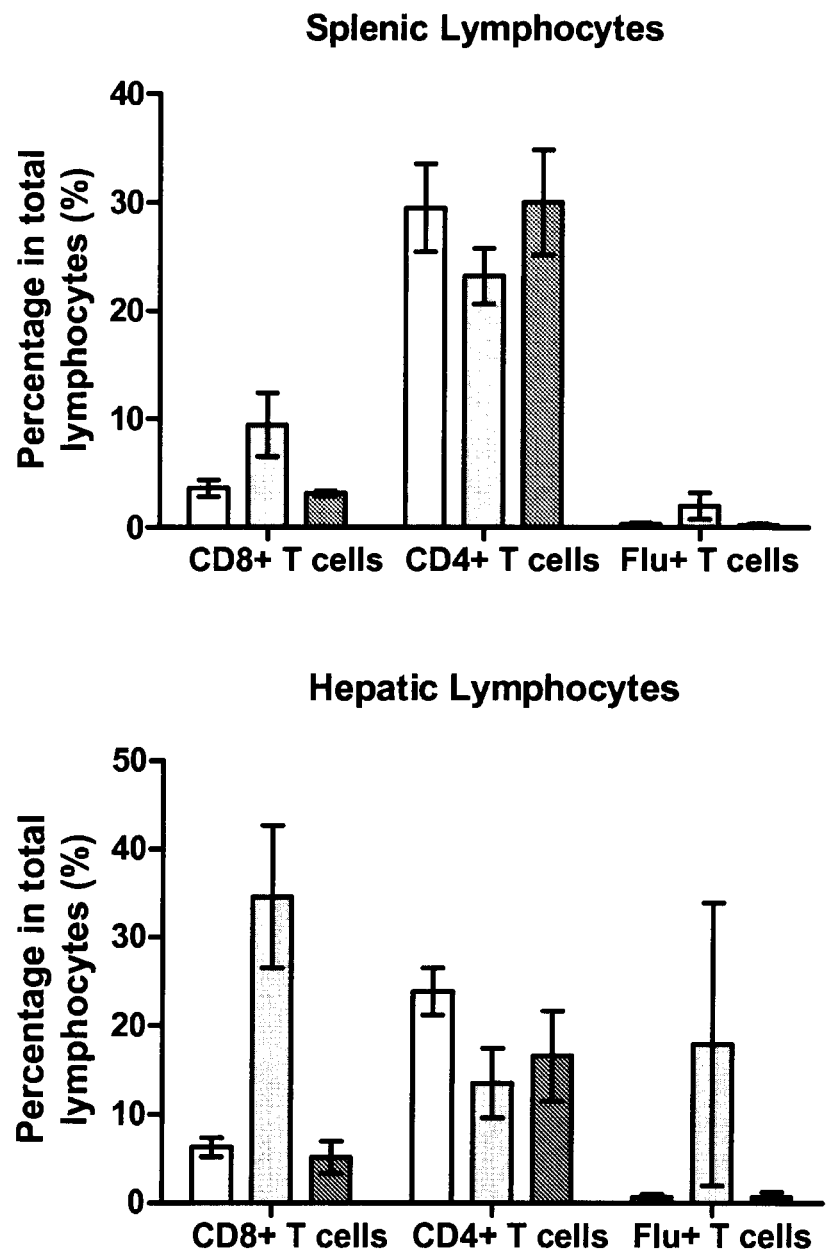

T cells and Flu-specific T cells were localized in spleen and liver. Results are shown in FIG. 10C. A strong increase of the % of $CD8^+$ T cells infiltrating liver and to a lesser extent in spleen was shown after hydrodynamic injection of prHBV1.3, compared to mice receiving pCMV-βGal or pCMV-rHBe. In contrast, the percentage of CD4 T cells in spleen or liver is comparable for the three groups of mice. In the liver, the majority of the lymphocyte population consists of Flu-specific $CD8^+$ T cells, as detected by tetramer-staining. These experiments indicate that after hydrodynamic injection of prHBV1.3, the Flu-specific T lymphocytes re-localize from the spleen to the liver.

Example 8

Construction of rHBV Genome Bearing a Foreign Polyepitope prHBV1.3 was constructed in the HBV ayw3 genotype background (Accession No. V01460, GenBank). The invention provides a plasmid of pCMV-Pol bearing a full length of polymerase gene and all the downstream viral elements in the HBV genome. Sequence adjacent to the start codon of the polymerase gene was modified as, 5'CCGAACATGGAG (SEQ ID NO: 1), consistent with the Kozak rule. Additionally, two restriction enzyme sites (Hind III and Pst I) were arranged prior to an ATG start codon, in order to adopt a 180 nucleotide fragment coding for the foreign polyepitope (synthesized by Genscript Corp., Piscataway, N.J.), that resulted in a new plasmid named pCMV-F-Pol. The embedded foreign sequence (F) shares the same reading frame with the remaining HBV core fragments (FIGS. 11A-11D).

Figure 11A:
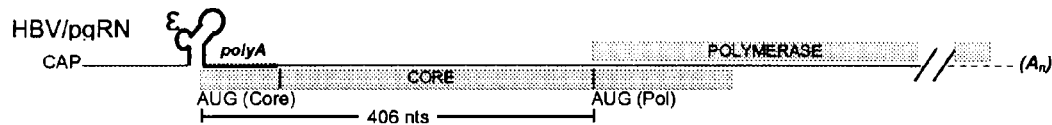
FIGS. 11A-11D show a schematic representation of rHBV constructs and plasmids.
Figure 11B:
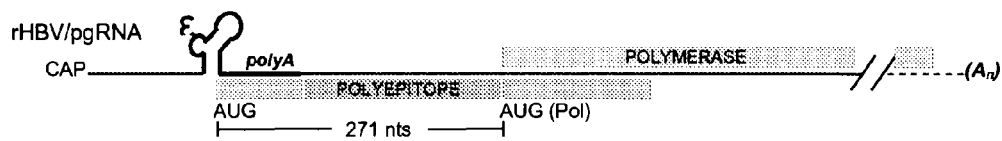

To generate 1.3 copies of the rHBV genome, a DNA fragment covering nt1075 to nt1981 of the HBV genome was PCR amplified, and took the place of the CMV promoter in the parental plasmid by digestion with Nru I and Hind III. pCMV-rHBc encodes the recombinant foreign antigen (rHBc) driven by CMV promoter. pMAS-C comprises the HBV core gene, under a CMV promoter. The plasmid prHBV1.3HBc has an additional expression cassette of HBV core protein. Briefly, a SV40 early promoter sequence (from pCDNA3, Invitrogen) was PCR amplified and inserted downstream of the rHBV genome in prHBV1.3, being separated by an f1 origin. The HBV core gene, together with a BGH polyA processing site, was further sublconed under the SV40 early promoter (FIG. 11D). Plasmids were purified using Qiagen DNA purification columns (Endofree Plasmid Kit™; Qiagen, Hilden, Germany).

Figure 11C:
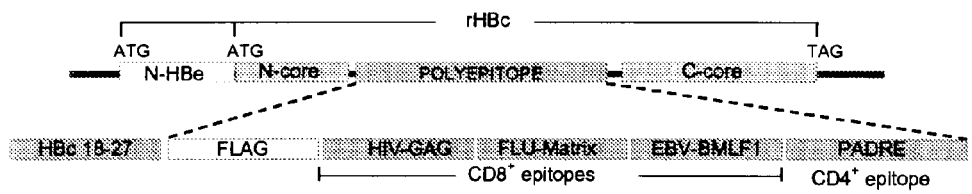
Figure 11D:
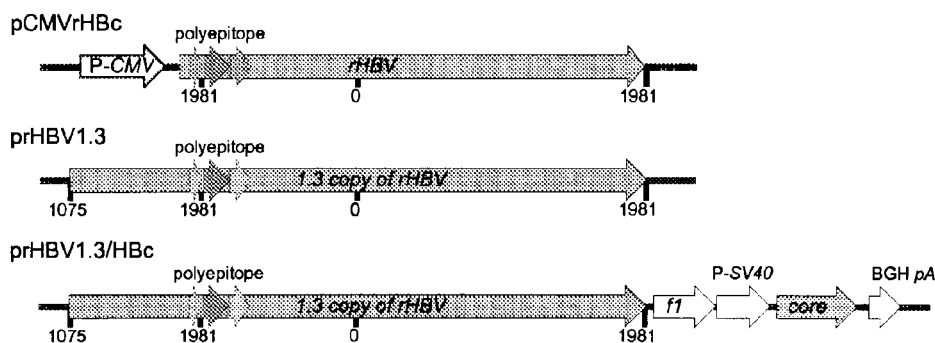

PCR amplification was performed by extracting viral DNA from mice sera with QIAamp DNA Blood Kit™ (Qiagen). The extracted DNA was treated with Pvu II digestion, to linearize the residual prHBV1.3 DNA contaminant plasmid. DNA bands covering an area of 2.5-3.5 kb in the gel after electrophoresis were purified as a template for PCR amplification, with the specific primers (3042F, 5'GTGGAGCCCTC AGGCTCAGGG (SEQ ID NO: 2); 459R, 5'GGA-CAAACGGGCAACATACC (SEQ ID NO: 3)).

rHBV was constructed to share most of its features with the wild type HBV genome (FIGS. 11A, 11B), with the exception of a 325-bp fragment within the HBV core gene, which was removed and substituted for by an in-frame 190-bp foreign sequence encoding a string of immunodominant T cell epitopes (FIG. 11C). As a result of the deletion, the open reading frame of the polymerase gene was shifted forward by 135 bp, bringing the ATG of the pol ORF much closer to the 5' CAP in the HBV pregenomic RNA (FIGS. 11A, 11B). The ATG starting signal of the polymerase gene was optimized according to Kozak's rules, in order to facilitate ribosome entry for the translation.

The foreign polyepitope was engineered with three immunodominant CD8+ T-cell epitopes combined with a promiscuous CD4+ T-cell epitope (PADRE) which could universally match up most of prevalent MHC class II molecules. Considering the clinical relevance, three well-known HLA-A2-restricted epitopes derived from common human viruses (HIV gag, Influenza matrix, EBV BML-F1) were chosen, in order to elicit a vigorous immune response in vivo. In this construct, the well known HBc18-27 HLA-A2 restricted epitope present in the amino-terminal part of the core gene was preserved. Additionally, a short B-cell epitope (FLAG) was introduced at the N-terminal part of the foreign sequence as a convenient detection marker (FIG. 11C). The core gene of HBV encodes two types of protein, the pre-core/HBeAg and the core proteins, which are translated from two distinct messenger RNA species. Two in-frame start codons are used for the translation of the two types of proteins. The core protein is the major constituent of the nucleocapsid, which carries HBcAg. HBeAg is a secreted protein produced by post-translational modifications of a precursor protein initiated at the first ATG of the core ORF. Therefore, a chimeric antigenic protein referred to as rHBc could be generated, with the foreign polyepitope fused in frame with the truncated HBe/capsid proteins (FIG. 11C).

prHBV1.3/HBc is a plasmid with two expression cassettes, one for rHBV genome expression and the other for expression of the capsid protein (FIG. 11D). The plasmid prHBV1.3 bears 1.3 copies of the rHBV genome only. Both plasmids were used for replication assays in vitro and in vivo. In pCM-VrHBc, the expression of the rHBc is driven by the CMV early gene promoter. A polyadenylation signal for mRNA is provided by HBV sequences (FIG. 11D). This plasmid was among those used to immunize mice.

Example 9

Expression of the Recombinant Protein Carrying the Polyepitope

The expression of the chimeric rHBc protein was first studied in a cell culture system. The human hepatoma cell lines HepG2 and Huh 7 were maintained in Dulbecco's Modified Eagle's Medium (DMEM) supplemented with 10% fetal calf serum (FCS). Polyethylenimine (PEI) was purchased from Sigma-Aldrich (St. Louis, Mo.), and used for transient transfection assays. Cell culture supernatant was harvested at day four post PEI transfection and used to prepare rHBV viral DNA.

The immuno fluorescence experiments were performed on HepG2 cells three days after DNA transfection, using published methods. Briefly, cells were fixed with 4% paraformaldehyde in phosphate buffered saline (PBS). Cells or tissue sections were incubated with anti-Flag mAb (1084; 1:100; Sigma-Aldrich) or anti-HBs mAb (3E7; 1:100; Dako, Glostrup, Denmark) at 4° C. overnight. After extensive washing, the bound primary antibody was detected by Alexa 488-labeled rabbit anti-mouse immunoglobulin G (Molecular Probes, Carlsbad, Calif.).

Histological staining was performed on freshly prepared mouse liver, frozen in isopentane pre-cooled in liquid nitrogen, and embedded in OCT compound in cryomolds. Five micron thick cryostat sections were mounted on superfrost plus slides and stored at −80° C. Before staining, slides were fixed in ice-cold acetone for 5-10 minutes. Liver sections were stained with hematoxylin and eosin, or immunostained with FITC labeled anti-HBs antibody (1:50; ab32914, Abcam, Cambridge, Mass.). After extensive washing with PBST and PBS, the liver sections were mounted with an anti-fade reagent containing DAPI.

After transient transfection of prHBV1.3 plasmid into hepatocyte-derived HepG2 cell line, a recombinant protein with the expected size (15 kD) was detected by Western blot in cell lysates using anti-FLAG antibody (FIG. 12A). The rHBc protein was also detected by antibody staining and immunoflorescence in the cytoplasm of HepG2 transfected cells, using anti-Flag antibody (FIG. 12B, lower panel). Expression of HBV envelope proteins in cells transfected with the rHBV was detected using an antibody against HBsAg, which is the major antigenic determinant of the envelope (FIG. 12B, upper panel). Interestingly, labeling of intracellular HBsAg was homogeneously dispersed in the cytoplasm, whereas the rHBe localized in the perinuclear area, with polarization. In addition, HBsAg particles carrying the HBV large envelope protein (L) were also detected by ELISA in cell culture supernatant after prHBV1.3 transfection (see below and FIG. 12D).

Example 10

Rescue of rHBV Particles and Replication by In Trans Encapsidation rHBV is a defective HBV virus owing to the disrupted core gene. However, it replicates and maintains in hepatocytes with the help of a wild type HBV capsid produced in trans in infected hepatocytes. The invention provides replicative forms of rHBV viral DNA in cell culture supernatant, e.g., from the Huh-7 hepatic cell line, after transfection of prHBV1.3/HBc plasmid encoding both rHBV genome and capsid protein but not after transfection of prHBV1.3.

Viral DNA associated with rHBV virions was extracted from the cell culture supernatants of HepG2- or Huh 7-transfected cells. Briefly, the virus particles in the medium were precipitated by incubation with 10% PEG 8000 overnight on ice. After centrifugation at 11,000 rpm for 30 minutes, the pellets were suspended in buffer (100 mM Tris/HCl (pH 8.0)), and further treated with DNase I (Invitrogen, Carlsbad, Calif.) in the presence of 10 mM $MgCl_2$. After proteinase K digestion (1 mg/ml), the viral DNA was precipitated using ethanol and glycogen as carrier. A Southern blot assay was performed by methods known in the art, with a $^{32}P$ labeled probe specific to the HBV genome.

Following DNA extraction and HBV-specific probe hybridization in Southern blot assays, the viral DNA was detected, in both its typical relaxed circular (RC) and double stranded linear (DSL) forms (FIG. 13A), indicating normal packaging and maturation of rHBV nucleocapsid. In addition, the core-rescued rHBV exhibited a more efficient viral cycle than wild type HBV. Upon co-transfection with pwtHBV, the replicative intermediates of rHBV were expressed at significantly greater levels than the wild type replicative forms, indicating the rescue, packaging, and maturation of rHBV virions in the presence of wild type capsid protein (FIG. 13C).

Hydrodynamic injection technology (Liu F., 1999, Gene Therapy) was used to introduce the rHBV genome into mouse liver. Four days after hydrodynamic injection of prHBV1.3 through the tail vein, both recombinant antigenic protein (rHBc) and HBV envelope proteins were detected in mouse liver by immunoflorescence staining of liver sections with anti-FLAG and anti-HBs antibodies respectively (FIG. 12C). Taken together, these experiments suggest that HBV envelope proteins and rHBc protein carrying the polyepitope are expressed after in vitro or in vivo transfection of the plasmid bearing 1.3 copies of rHBV genome.

In addition, recombinant rHBV virions were detected in the sera of mice receiving both prHBV1.3 and pMAS-C by hydrodynamic injection, using specific PCR amplification at day four after the injection. In contrast, in the absence of pMAS-C, injection of prHBV1.3 alone or with co-injection of a plasmid encoding beta-galactosidase (pCMV-βGal), no viral DNA was detected (FIG. 13D). Therefore, the rHBV genome can be complemented in trans by capsid proteins in vitro and in vivo giving rise to complete viral particles containing replicative forms of viral DNA.

The large envelope protein (L) is known to be localized on the surface of 42 nm HBV complete viral particles and on the filamentous sub-viral particles present in the sera of HBV-infected individuals. To demonstrate that complete viral particles can be produced from the rHBV genome, cotransfection experiments of prHBV1.3 and a plasmid encoding the core protein (pMAS-C) in Huh-7 cell line were performed. Cotransfection with the core-encoding plasmid resulted in an increase in the production of L protein-carrying particles in cell culture supernatant, compared with transfection of prHBV1.3 alone or cotransfection with pIRES-GFP as control. The increase in L protein production was dose-dependent as shown in a specific ELISA using two different monoclonal antibodies recognizing the amino-terminal part of L protein (FIG. 13B).

Example 11

Activation of Polyepitope-specific T-cell Responses

IFN-γ producing splenocytes were quantified by ex vivo Elispot assays after stimulation with peptide, as known in the art. Briefly, 96-well nitrocellulose HA plates (Millipore, Bedford, Mass.) were coated by incubation overnight at 4° C. with capture antibody against IFN-γ (551216; BD Pharmingen, San Diego, Calif.). Freshly isolated splenocytes ($10^6$/well) were incubated with individual peptide at a concentration of 1 µg/ml in supplemented α-MEM medium for 24 hours. Spots were developed by a secondary biotin-conjugated antibody (554410; BD Pharmingen, San Diego, Calif.) and alkaline phosphatase conjugated streptavidin (Roche, Basel, Switzerland). A Zeiss Elispot automatic counter was used to score the number of spots. The response was considered positive if the median number of spot-forming cells (SFC) in triplicate wells was at least twice that in control wells containing medium alone.

For the proliferation assay, splenocytes ($10^6$ cells/well) were incubated with 20 µg/ml of peptide for three days in supplemented HL1 serum-free medium (Biowhitaker, Walkersville, Md.) (Pajot et al., 2004). Cells were pulsed for the final 16 h with 1 µCi of ($^3$H)-thymidine per well. The incorporated radioactivity was measured on a micro-β counter.

Figure 14A:
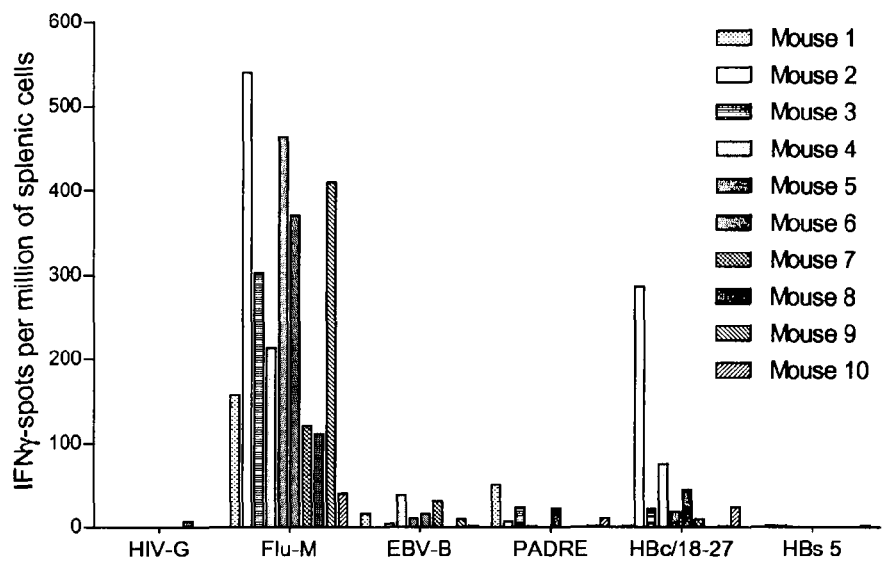
FIGS. 14A-14C show polyepitope-specific T-cell responses in mice injected with pCMV-rHBe.

To evaluate T-cell responses against the foreign polyepitope, a DNA plasmid encoding rHBc (pCMV-rHBc, as described in Example 1) was used to immunize HLA-A2/DR1 transgenic mice (Pajot et al., 2004). Two weeks after intramuscular injection, nine of the ten mice tested mounted epitope-specific T cell responses, as detected using ex vivo IFNγ-ELISPOT assays (FIG. 14A).

The Flu matrix-derived epitope is obviously the most frequently recognized and most powerful among the three foreign CD8$^+$ T cell epitopes (9 out of 10 responder mice). Flu-specific T cell response even dominated over the response to the well-described capsid-derived HBc18-27 HLA-A2 epitope that is present in the N-terminal part of the protein. The immunodominant response to the Flu-derived epitope probably resulted from competition between peptides for fixation to the HLA-A2 molecule. Nevertheless, Gag- and EBV-specific T cells were detectable after one week in vitro stimulation of splenocytes with individual peptides. T cell responses to the Flu matrix epitope were also quantified using a HLA-A2-pentamer (ProImmune, Oxford, UK) carrying the Flu peptide to label splenocytes from DNA-immunized mice. Accordingly, Flu-specific T cells represent around 10% of CD8$^+$ T cells from the spleen (FIG. 14B, right panel).

Figures 14B, 14C:
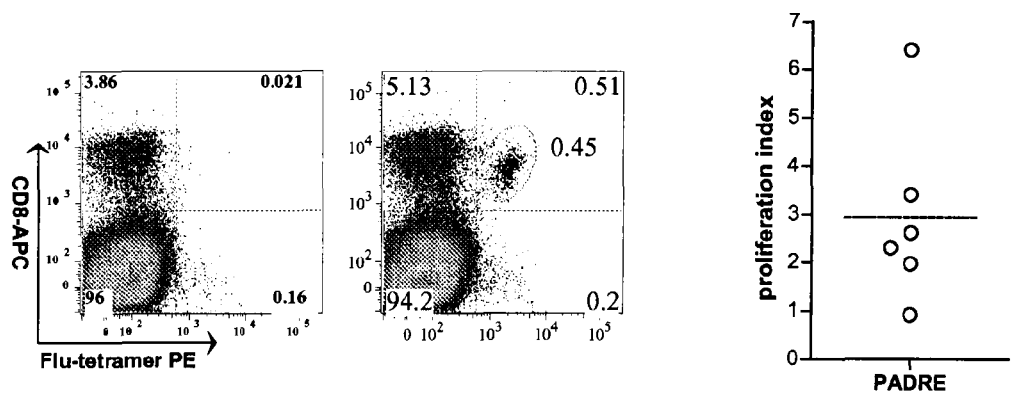

Mice receiving pCMV-rHBe injection also developed T helper responses against the MHC class II-restricted epitope PADRE, as demonstrated by both I IFNγ-ELISPOT assay (FIG. 14A) and specific proliferation observed in five out of six immunized mice, upon stimulation of splenocytes with PADRE peptide (FIG. 14C).

Example 12

Retargeting Polyepitope-Specific T Cell Responses to Liver

Mice were perfused with 20 ml PBS via ventricle route. The liver was smashed with a syringe plunger in a 100 µm cell strainer (100 µm Nylon, BD, Franklin Lakes, N.J.). Cell pellets were resuspended in 15 ml of 40% Purcell (Sigma, St. Louis, Mo.) and centrifuged at 2000 rpm for 20 minutes, to remove the hepatocyte clumps. The intrahepatic lymphocytes in the pellets were further purified through a Ficoll gradient centrifugation as for the separation of mouse splenocytes. Freshly isolated lymphocytes were stained by PerCP-labeled anti-CD3, APC-labeled anti-CD8 antibodies, or by PE-labeled HLA class I tetramer conjugated with Flu peptide.

Figure 15A:
FIGS. 15A-15D show T cell responses in the liver and spleen of HLA-A2/DR1 transgenic mice, following hydrodynamic injection of rHBV.

For FACS analysis, at least 10000 events gated among the population of interest were analyzed on a FACSCalibur cytometer using CellQuest program (BD Biosciences, Franklin Lakes, N.J.). To demonstrate that rHBV co-maintains with wild type HBV virus in liver, and in the absence of a mouse model of HBV infection and replication, the invention provides a protocol of rHBV-based active immunotherapy in HLA-A2/DR1 transgenic mice (FIG. 15A).

HLA-A2/DR1 mice were immunized by intramuscular injection of plasmid pCMV-rHBc at day 0 to prime polyepitope-specific T cell responses in periphery. Two weeks later, prHBV1.3 was injected via a hydrodynamic route to bypass hepatocyte infection and mimic HBV replication in liver (Yang P., Althage L. A., Chung J., Chisari F. V., 2002, Hydrodynamic injection of viral DNA: a mouse model of acute hepatitis B virus infection, Proc Natl Acad Sci, U.S.A. 99:13825-30). Thus, rHBV can be expressed in liver cells with the encoded foreign antigen being processed into peptides and presented in situ providing, in turn, intrahepatic targets for a CD8$^+$ T cell response. pCMV-βGal was used as a control plasmid for hydrodynamic injection.

Figure 15B:
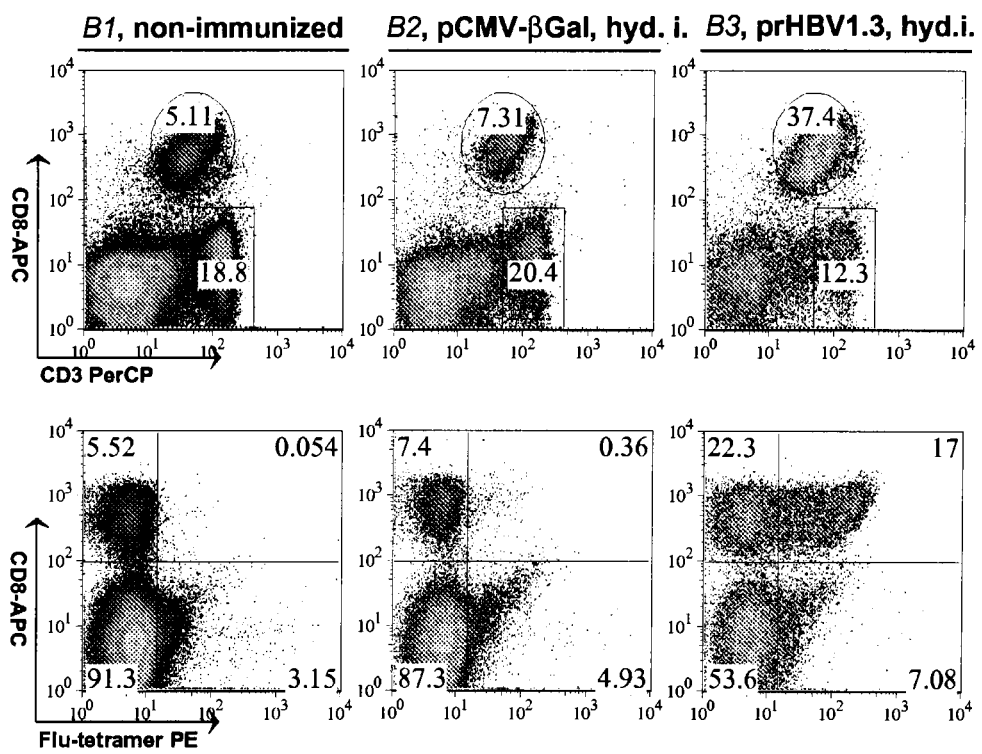

Following priming and hydrodynamic injection of prHBV1.3, mice mounted a vigorous intrahepatic T-cell response, with a large number of CD8$^+$ T lymphocytes infiltrating the liver. CD8$^+$ T lymphocytes accumulated in the mouse livers, as detected by FACS analysis of liver-infiltrating lymphocytes taken at days 3, 4 and 7. At day 7, the percentage of liver-infiltrating CD8$^+$ T cells represented up to 37.4% of total lymphocytes in mice receiving prHBV1.3, compared to mice receiving pCMV-βGal (7.31%) and to non immunized mice (5.11%) (FIG. 15B). 17% of the T cells, representing 42% of the total liver-infiltrating lymphocytes, in the mice that received prHBV1.3 were Flu-specific. In comparison, only 0.36% of the Flu-specific CD8$^+$ T cells primed by intramuscular injection were present in the liver seven days after pCMV-βGal hydrodynamic injection.

Figure 15C:
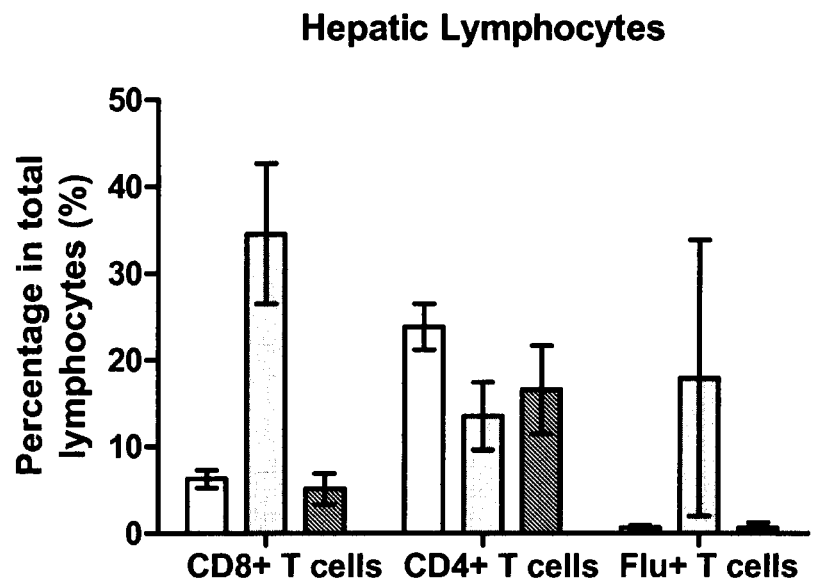
Figure 15D:
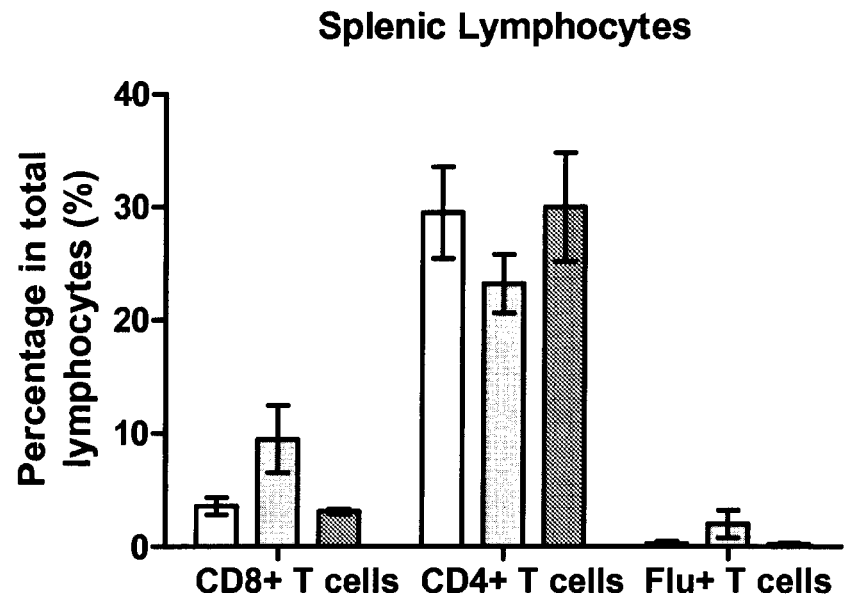

FIGS. 15C and 15D demonstrate the relative distribution of CD8$^+$ and CD4$^+$ T cells in the livers and spleens from groups of primed mice receiving either prHBV1.3 or pCMV-βGal by hydrodynamic injection, or receiving two intramuscular injections of pCMV-rHBc. A strong increase in the percentage of CD8+ T cells was observed in the liver and, to a lesser extent, in the spleens of mice after hydrodynamic injection of prHBV1.3, compared to mice receiving pCMV-βGal and to mice receiving pCMV-rHBc only.

Remarkably, a large increase in the percentage of Flu-specific CD8+ T cells was observed in the livers of mice receiving prHBV1.3. Following immunization, Flu-specific CD8$^+$ T cells comprised a very high percentage of hepatic lymphocytes, compared to the percentage of splenic lymphocytes (p=0.0002). In contrast, the percentages of CD4$^+$ T cells in the spleen and the liver were not significantly different in the three groups of mice. In the presence of the vigorous CD8$^+$ T cell response, the CD4$^+$ T cell reservoir was relatively reduced in the liver, but not in the spleen. These experiments demonstrate that the majority of Flu-specific peripheral CD8$^+$ T lymphocytes relocalized to the liver following rHBV-based active immunization.

The increase in the percentage of total lymphocytes derived after immunization reached statistical significance in both the liver and the spleen. As shown in FIG. 15C, the percentage of CD8$^+$ lymphocytes observed in the livers of mice receiving pCMVrHBe priming followed by prHBV1.3 hydrodynamic injection was significantly higher than in the livers of mice receiving pCMVrHBe priming followed by pCMVβGal hydrodynamic injection (p=0.0001), and significantly higher than mice injected twice with pCMVrHBe via the intramuscular route (p=0.0009).

A similar increase in the percentage of CD8$^+$ lymphocytes observed in the spleens of mice receiving pCMVrHBe priming followed by prHBV1.3 hydrodynamic injection was significantly higher than in the spleens of mice receiving pCMVrHBe priming followed by pCMVβGal hydrodynamic injection (p=0.0011), and significantly higher than mice injected twice with pCMVrHBe via the intramuscular route (p=0.0114).

Example 13

Figure 16A:
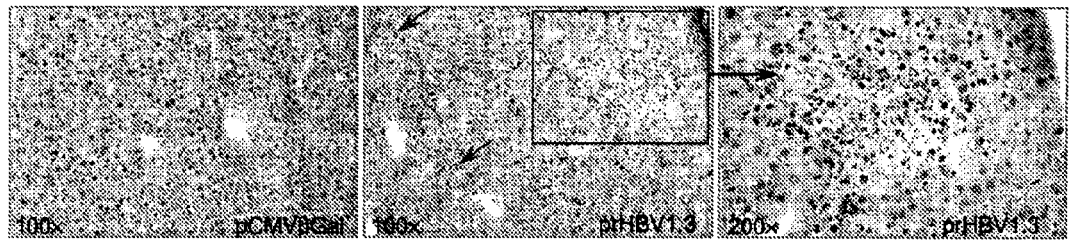

Non-Cytolytic Control of HBV Gene Expression in Liver Mediated by Polyepitope-Specific T Cells CD8$^+$ T cells are the major population in hepatic infiltrates on day seven after hydrodynamic injection, as described above. Further analysis of the liver infiltrates was performed by histochemical analysis of liver sections taken four days after prHBV1.3 injection (FIG. 16A). A remarkable infiltration of inflammatory cells was observed in the liver, and was predominantly centered into clusters of various sizes, suggesting that they developed quickly to form inflammatory foci. The presence of these infiltrates was dependant on priming peripheral T cell responses, as few cell clusters were found in liver sections taken from mice receiving hydrodynamic injection of prHBV1.3 without previous priming.

Little or no clustered infiltrates were observed in mice receiving pCMV-rHBe priming followed by pCMV-βGal hydrodynamic injection (FIG. 16A).

Figure 16B:
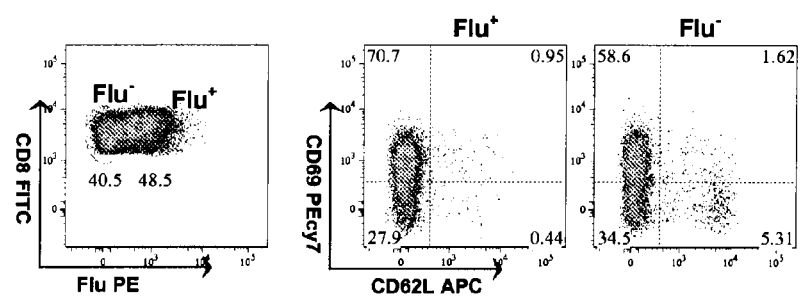
Figure 16C:
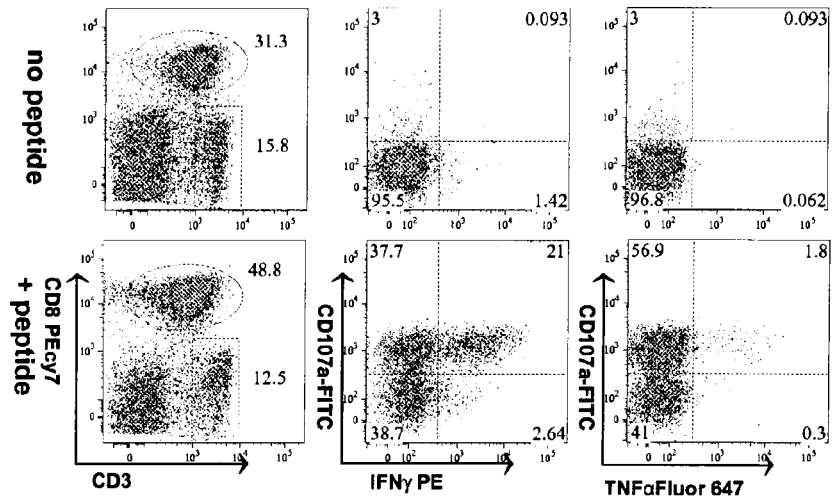

Flu-specific T cells were further phenotyped as CD44$^+$, CD62L$^{low}$, and CD69$^{high}$ (FIG. 16B), corresponding to activated or effector memory T cells undergoing an in vivo expansion. Upon an ex vivo stimulation by Flu peptide, these cells, freshly isolated from liver, produced mostly INFγ but also produced TNFα, detected by intracellular staining (FIG. 16C). Around 58% of CD8$^-$ T cells were positive for surface staining with CD107a, a marker of cellular degranulation (FIG. 16C). Taken together, these data demonstrate that the liver infiltrating cells were predominantly functional CD8$^+$ effector T cells.

Knowing that HBV gene expression in liver is susceptible to a non-lytic control by IFN-γ-secreting T cells following antigen recognition, we monitored the expression of rHBV expression in the liver and sera of mice. Four days after prHBV1.3 hydrodynamic injection intrahepatic expression of HBsAg was undetectable in mice receiving pCMV-rHBe priming (FIG. 16D, left panel) compared to mice receiving prHBV1.3 only (FIG. 16D, right panel). Accordingly a 100 fold decrease in HBsAg was observed in sera of mice in which T cells were primed before prHBV1.3 injection (FIG. 16E). In contrast, in the absence of peripherally primed T cells, mice exhibited a strong HBsAg expression after prHBV1.3 hydrodynamic injection. HbsAg expression was demonstrated by immunofluorescence staining of liver sections (FIG. 16D, right panel) and HbsAg measurement in sera using a commercial detection kit (Monolisa HBsAg ULTRA, Bio-Rad) (FIG. 16E, left panel). Taken together these experiments demonstrate a rapid non-cytolytic control of rHBV gene expression by polyepitope-activated CD8$^+$ T cells.

These infiltrating T cells can hypothetically be responsible for liver injury. However, no significant increase in the injury marker ALT was observed in the sera of mice receiving prHBV1.3 via hydrodynamic injection, as compared to those receiving pCMV-βgal as a control, four days following prHBV1.3 hydrodynamic injection (FIG. 16F). At day four post hydrodynamic injection, the mean serum alanine transferase (ALT) level was 94.18±30.33 mU/ml in the 11 mice receiving rHBV-based immunization. In comparison, the serum ATL levels remained normal in mice receiving pCMV-rHBc priming followed by pCMV-βGal hydrodynamic injection (mean=38.00±5.35), while a striking increase was observed in the sera of mice with Concanavalin A-induced acute hepatitis (FIG. 16F) (Zhu R., et al., 2007, The Pro-Th1 cytokine IL-12 enhances IL-4 production by invariant NKT cells: relevance for T cell-mediated hepatitis, J. Immunol., 178:5435-42). It therefore suggests that, in the presence of the peripherally built-up T cell response, expression of rHBV rapidly attracted T cell response in liver without raising a major liver injury.

Example 14

Active Immunotherapy in HBsAg Transgenic Mice

The invention further demonstrates organ-specific viral targeting and expression of the pseudo-viruses of the invention, using a transgenic mouse lineage expressing HBV envelope proteins in liver and secreting HBsAg in sera. This lineage was previously back-crossed with HLA-A2 transgenic mice and is devoid of murine MHC class I molecules. The HLA-A2/DR1 (HLA-A02.01/DR1-transgenic, H-2 class I/class II KO) and HBsAg/HLA-A2 transgenic mice used in this study were bred in the animal facilities of Institut Pasteur (Pajot et al., 2004).

The HBsAg/HLA-A2 double transgenic lineage (H-2 class I KO) is endowed with HLA-A2 background and produces HBsAg in mouse liver following transgene expression. Intramuscular DNA immunization was carried out by injecting 100 µg of plasmid DNA into regenerating (i.e. cardiotoxin-treated) tibialis anterior muscles. For hydrodynamic injection, female mice around 12-15 weeks old were used. Briefly, 25 µg of plasmid DNA was injected through the tail vein in a volume of PBS equivalent to 8% of the mouse's body weight. The total volume was delivered within five seconds. Mice were bled and sera assayed for HBsAg by specific ELISA at indicated times. All experiments involving mice were performed according to European guidelines.

Figure 17A:
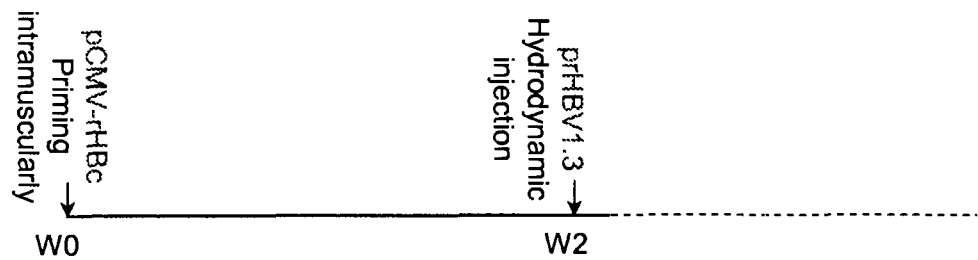
FIGS. 17A-17C show the control of HBsAg expression in HBsAg/HLA-A2 transgenic mice.
Figure 17B:
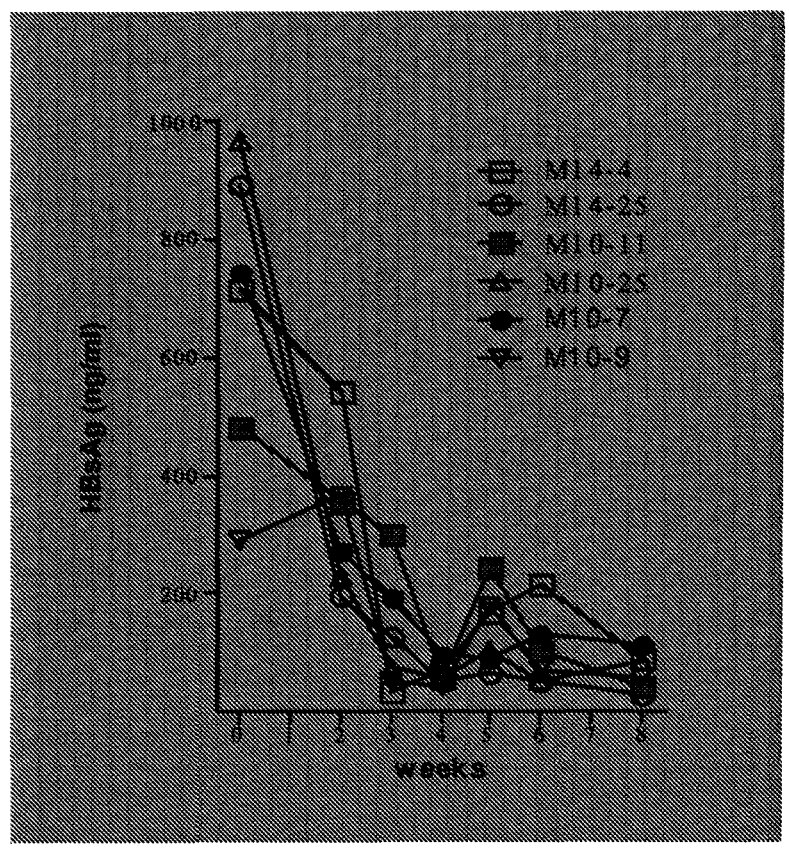
Figure 17C:
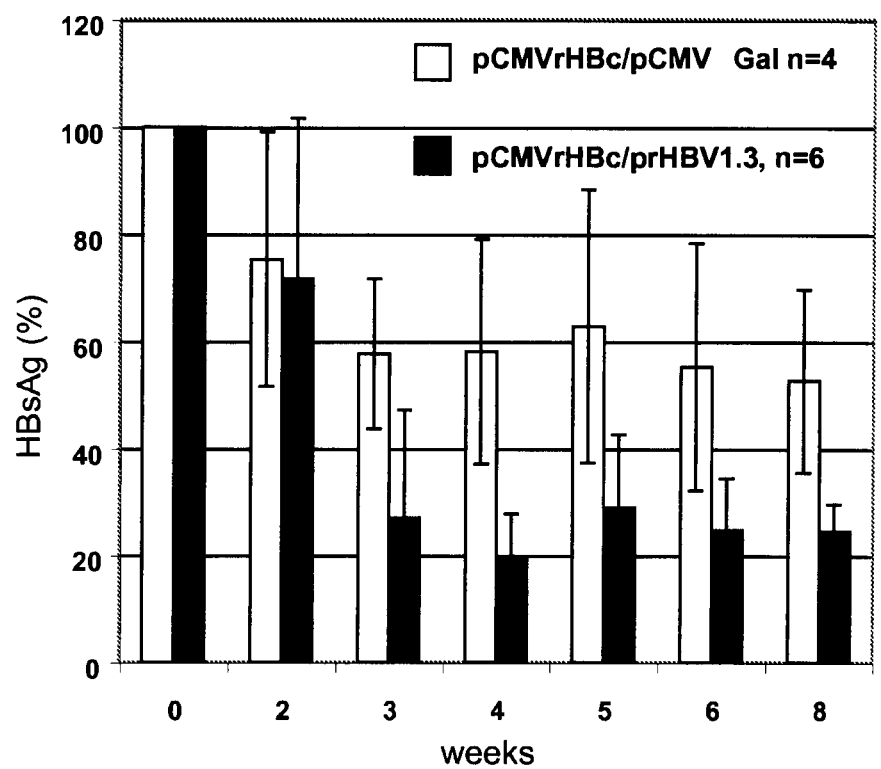

Following priming and hydrodynamic injection, mice were bled weekly to monitor HBsAg concentration in sera. A decrease in HBsAg in sera was first observed two weeks after priming and was followed by a second sharp decrease in all mice examined one to two weeks after prHBV1.3 hydrodynamic injection (FIG. 17B). The decrease after priming corresponds to the influx of polypeptide specific T cells from the circulation to the liver. The decrease in HBsAg reached up to 90%, compared to the starting level in some of the mice tested (FIG. 17B). In contrast, in mice receiving pCMV-βGal as control, no significant HBsAg decrease was observed following hydrodynamic injection (FIG. 17C).

Clearance of HBsAg was not complete, and antigen level fluctuated around 25% of basal level during a two-month follow up. HbsAg clearance was strong and long-lasting, however, when compared to the pCMV-βGal control animals eight weeks after immunization (p<0.0001).

We have previously shown that HBV mRNA in the liver is susceptible to down regulation by INF-γ secreted by HBsAg-specific vaccine-activated T cells (Mancini-Bourgine et al., 2004). Mice with HBsAg/HLA-A2 backgrounds transgenic for HbsAg also display an antiviral response to rHBV-based active immunization.

The clearance of HBsAg demonstrated by the methods of the invention is likely to be related to the non-HBV, polyepitope specific influx of Flu-specific T cells into the liver and to a bystander effect of INFγ-secreting T cells on HBsAg-expressing hepatocytes. This suggests that these functional effector T cells not only control rHBV expression, as shown in FIG. 16E, but also demonstrates HBV transgene expression in the liver.

In summary, the instant application presents a novel, efficient, and feasible strategy for the use of active immunization for the treatment of persistent viral infections, satisfying a long-felt need in the art.

Throughout this application, the terms "rHBe" and "rHBc" refer, without distinction, to the translational products of the modified preCC open reading frame.

REFERENCES

The following references are cited herein. The entire disclosure of each reference cited below, and also of those cited above, is relied upon and incorporated by reference herein.

1. Bertoletti A., and A. J. Gehring. 2006. The immune response during hepatitis B virus infection. J Gen Virol 87:1439-49.
2. Chisari F. V., and C. Ferrari. 1995. Hepatitis B virus immunopathogenesis Annu Rev Immunol 13:29-60.
3. Ganem D., and A. M. Prince. 2004. Hepatitis B virus infection—natural history and clinical consequences. N Engl J Med 350:1118-29.
4. Guidotti L. G., and F. V. Chisari. 2001. Noncytolytic control of viral infections by the innate and adaptive immune response. Annu Rev Immunol 19:65-91.
5. Gunther S., N. Piwon, A. Jung, A. Iwanska, H. Schmitz, and H. Will. 2000. Enhanced replication contributes to enrichment of hepatitis B virus with a deletion in the core gene. Virology 273:286-99.
6. Mancini M., M. Hadchouel, H. L. Davis, R. G. Whalen, P. Tiollais, and M. L. Michel. 1996. DNA-mediated immunization in a transgenic mouse model of the hepatitis B surface antigen chronic carrier state. Proc. Natl. Acad. Sci. USA 93:12496-12501.
7. Mancini-Bourgine M., H. Fontaine, D. Scott-Algara, S. Pol, C. Brechot, and M. L. Michel. 2004. Induction or expansion of T-cell responses by a hepatitis B DNA vaccine administered to chronic HBV carriers. Hepatology 40:874-82.
8. Morosan S., S. Hez-Deroubaix, F. Lunel, L. Renia, C. Giannini, N. Van Rooijen, S. Battaglia, C. Blanc, W. Eling, R. Sauerwein, L. Hannoun, J. Belghiti, C. Brechot, D. Kremsdorf, and P. Druilhe. 2006. Liver-stage development of *Plasmodium falciparum*, in a humanized mouse model. J Infect Dis 193:996-1004.
9. Rehermann B., and M. Nascimbeni. 2005. Immunology of hepatitis B virus and hepatitis C virus infection. Nat Rev Immunol 5:215-29.
10. Yang P. L., A. Althage, J. Chung, and F. V. Chisari. 2002. Hydrodynamic injection of viral DNA: a mouse model of acute hepatitis B virus infection. Proc Natl Acad Sci U.S.A., 99:13825-30.
11. Nakabayashi H., K. Taketa, K. Mlyano, T. Yamane, and J. Sato. 1982. Growth of human hepatoma cell lines with differentiated functions in chemically defined medium. Cancer Res. 42(9):3858-63.
12. ATCC number HB-8065.
13. Pajot A., M. L. Michael, N. Fazilleau, V. Pancre, C. Auriault, D. M. Ojcius, F. A. Lemonnier, and Y. C. Lone. 2004. A mouse model of human adaptive immune functions: HLA-A2.1/HLA-DR1-transgenic H-2 class I/class II-knockout mice. Eur J Immunol. 34(11):3060-9.

---

The invention claimed is:

1. A recombinant replication defective hepatitis B virus (HBV) comprising:
   a hepatitis B virus genome defective for replication due to a deletion in the capsid-encoding portion of the virus, wherein the virus contains a polyadenylation signal for HBV mRNA, a polymerase reading frame, and a nucleotide sequence of up to about 195 nucleotides encoding at least one heterologous immuno-dominant epitope of a pathogenic bacteria or virus fused within the N-terminal part of the capsid-encoding portion of the virus between the polyadenylation signal and the start of the polymerase reading frame;
   wherein following infection by the virus of an isolated vertebrate hepatocyte comprising a nucleotide sequence encoding HBc for complementation of the recombinant hepatitis virus, the nucleotide sequence encoding the immuno-dominant epitope of a pathogenic bacteria or virus is expressed and the immuno-dominant epitope of a pathogenic bacteria or virus is presented at the surface of the vertebrate hepatocyte as a T cell target.

2. An immunogenic composition comprising the recombinant replication defective virus of claim 1 and a pharmaceutically acceptable carrier.

3. A recombinant hepatitis pseudo-virus comprising the recombinant replication defective hepatitis virus as claimed in claim 1 complemented by HBc, wherein the pseudo-virus replicates in vitro in human hepatocytes.

4. A cloning and/or expression vector encoding a recombinant replication defective hepatitis virus as claimed in claim 1.

5. An isolated hepatocyte cell of a vertebrate infected by the recombinant replication defective hepatitis virus as claimed in claim 1.

6. The isolated hepatocyte cell as claimed in claim 5, wherein the cell further comprises a nucleotide sequence encoding HBc for complementation of the recombinant hepatitis virus to form a hepatitis pseudo-virus, wherein the nucleotide sequence encoding the immuno-dominant epitope of a pathogenic bacteria or virus is expressed and the immuno-dominant epitope of a pathogenic bacteria or virus is presented at the surface of the hepatocyte as a T cell target.

7. An isolated hepatocyte cell of a vertebrate infected by the hepatitis pseudo-virus as claimed in claim 3, wherein the nucleotide sequence encoding the immuno-dominant epitope of a pathogenic bacteria or virus is expressed in the hepatocyte and the immuno-dominant epitope of a pathogenic bacteria or virus is presented at the surface of the hepatocyte as a T cell target.

8. An isolated eukaryotic host cell comprising a vector as claimed in claim 4.

9. A method of forming a hepatitis pseudo-virus, wherein the method comprises culturing the hepatocyte cell claimed in claim 6 under conditions for expression of a nucleotide sequence encoding the HBc, and complementation of the recombinant, replication defective hepatitis virus to form a hepatitis pseudo-virus.

10. A method of producing hepatitis pseudo-virus, wherein the method comprises:
   providing a host cell as claimed in claim 8: and
   expressing hepatitis proteins under conditions where the proteins assemble into hepatitis pseudo-virus, which are released from the host cell into the extracellular space.

11. A method as claimed in claim 10, which comprises recovering the hepatitis pseudo-virus.

12. A method of treating a patient chronically infected with hepatitis B virus, wherein the method comprises
   administering to the virus-infected patient a recombinant replication defective hepatitis virus as claimed in claim 1 in an amount sufficient to deliver the nucleotide sequence encoding the immuno-dominant epitope of a pathogenic bacteria or virus into the liver of the patient where the immuno-dominant epitope of a pathogenic bacteria or virus is expressed and presented at the surface of hepatocytes as a target for a T cell response in the patient to thereby clear virus from hepatitis virus-infected hepatocytes of the patient.

13. A method for stimulating a T cell response against cells infected with a hepatitis b virus in a patient persistently infected with said virus, wherein said method comprises administering to said patient a composition according to claim 2.

14. A method for targeting the expression of an immuno-dominant epitope of a pathogenic bacteria or virus to the surface of a vertebrate hepatocyte infected by a hepatitis B virus, wherein said method comprises providing to the vertebrate hepatocyte infected by a hepatitis B virus the recombinant replication defective virus of claim 1.

* * * * *

SEQUENCE LISTING

<160> NUMBER OF SEQ ID NOS: 26

<210> SEQ ID NO 1
<211> LENGTH: 12
<212> TYPE: DNA
<213> ORGANISM: artificial sequence
<220> FEATURE:
<223> OTHER INFORMATION: Sequence adjacent to the start codon of the polymerase gene from the HBV genome

```
<400> SEQUENCE: 1
ccgaacatgg ag                                                             12

<210> SEQ ID NO 2
<211> LENGTH: 21
<212> TYPE: DNA
<213> ORGANISM: artificial sequence
<220> FEATURE:
<223> OTHER INFORMATION: Primer sequence

<400> SEQUENCE: 2
gtggagccct caggctcagg g                                                   21

<210> SEQ ID NO 3
<211> LENGTH: 20
<212> TYPE: DNA
<213> ORGANISM: artificial sequence
<220> FEATURE:
<223> OTHER INFORMATION: Primer sequence

<400> SEQUENCE: 3
ggacaaacgg gcaacatacc                                                     20

<210> SEQ ID NO 4
<211> LENGTH: 6831
<212> TYPE: DNA
<213> ORGANISM: artificial sequence
<220> FEATURE:
<223> OTHER INFORMATION: Sequence for prHBV-1.3-III

<400> SEQUENCE: 4
gacggatcgg gagatctccc gatcccctat ggtcgactct cagtacaatc tgctctgatg         60
ccgcatagtt aagccagtat ctgctccctg cttgtgtgtt ggaggtcgct gagtagtgcg        120
cgagcaaaat ttaagctaca caaggcaag gcttgaccga caattgcatg aagaatctgc         180 ttaggggttag gcgttttgcg ctgcttcgca atctaagcag gctttcactt tctcgccaac       240
ttacaaggcc tttctgtgta acaatacct gaaccttac cccgttgccc ggcaacggcc         300
aggtctgtgc caagtgtttg ctgacgcaac ccccactggc tggggcttgg tcatgggcca        360
tcagcgcatg cgtggaacct tttcggctcc tctgccgatc catactgcgg aactcctagc       420
cgcttgtttt gctcgcagca ggtctggagc aaacattatc gggactgata actctgttgt       480
cctatcccgc aaatatacat cgtttccatg ctgctaggc tgtgctgcca actggatcct        540
gcgcgggacg tcctttgttt acgtcccgtc ggcgctgaat cctgcggacg acccttctcg       600
gggtcgcttg ggactctctc gtccccttct ccgtctgccg ttccgaccga ccacggggcg       660
cacctctctt tacgcggact ccccgtctgt gccttctcat ctgccggacc gtgtgcactt       720
cgcttcacct ctgcacgtcg catggagacc accgtgaacg cccaccaaat attgcccaag      780
gtcttacata agaggactct tggactctca gcaatgtcaa cgaccgacct tgaggcatac      840
ttcaaagact gtttgtttaa agactgggag gagttggggg aggagattag gttaaaggtc      900
tttgtactag gaggctgtag gcataaattg gtctgcgcac cagcaccatg caacttttc      960 acctctgcct aatcatctct tgttcatgtc ctactgttca gcctccaag ctgtgccttg      1020 ggtggctttg ggcatggac atcgaccctt ataagaatt tggagctact gtggagttac      1080
tctcgttttt gccttctgac ttctttcctt cagtaagctt cgaacatgga gccctatcc      1140 tatcaacact tccggagact actgttgtta gacgacgagg caggtcccct agaagaagaa      1200
ctccctcgcc tcgcagacga aggtctcaat cgccgcgtcg cagaagatct caatctcggg      1260
```

```
aatctcaatg ttagtattcc ttggactcat aaggtgggga acttactgg gctttattct    1320
tctactgtac ctgtctttaa tcctcattgg aaaacaccat cttttcctaa tatacattta    1380
caccaagaca ttatcaaaaa atgtgaacag tttgtaggcc cactcacagt taatgagaaa    1440
agaagattgc aattgattat gcctgccagg ttttatccaa aggttaccaa atatttacca    1500
ttggataagg gtattaaacc ttattatcca gaacatctag ttaatcatta cttccaaact    1560
agacactatt tacacactct atggaaggcg ggtatattat ataagagaga acaacacat    1620
agcgcctcat tttgtgggtc accatattct tgggaacaag atctacagca tggggcagaa    1680
tctttccacc agcaatcctc tgggattctt tcccgaccac cagttggatc cagccttcag    1740
agcaaacacc gcaaatccag attgggactt caatcccaac aaggacacct ggccagacgc    1800
caacaaggta ggagctggag cattcgggct gggtttcacc ccaccgcacg gaggcctttt    1860
ggggtggagc cctcaggctc agggcatact acaaactttg ccagcaaatc cgcctcctgc    1920
ctccaccaat cgccagtcag gaaggcagcc taccccgctg tctccacctt tgagaaacac    1980
tcatcctcag gccatgcagt ggaattccac aaccttccac caaactctgc aagatcccag    2040
agtgagaggc ctgtatttcc ctgctggtgg ctccagttca ggaacagtaa accctgttct    2100
gactactgcc tctcccttat cgtcaatctt ctcgaggatt ggggaccctg cgctgaacat    2160
ggagaacatc acatcaggat cctaggacc ccttctcgtg ttacaggcgg ggttttcttt    2220
gttgacaaga atcctcacaa taccgcagag tctagactcg tggtggactt ctctcaattt    2280
tctaggggga actaccgtgt gtcttggcca aaattcgcag tccccaacct ccaatcactc    2340
accaacctct tgtcctccaa cttgtcctgg ttatcgctgg atgtgtctgc ggcgttttat    2400
catcttcctc ttcatcctgc tgctatgcct catcttcttg ttggttcttc tggactatca    2460
aggtatgttg cccgtttgtc ctctaattcc aggatcctca acaaccagca cgggaccatg    2520
ccggacctgc atgactactg ctcaaggaac ctctatgtat ccctcctgtt gctgtaccaa    2580
accttcggac ggaaattgca cctgtattcc catcccatca tcctgggctt tcggaaaatt    2640
cctatgggag tgggcctcag cccgtttctc ctggctcagt ttactagtgc catttgttca    2700
gtggttcgta gggctttccc ccactgtttg gctttcagtt atatggatga tgtggtattg    2760
ggggccaagt ctgtacagca tcttgagtcc cttttttaccg ctgttaccaa ttttcttttg    2820
tctttgggta tacatttaaa ccctaacaaa acaaagagat ggggttactc tctaaatttt    2880
atgggttatg tcattggatg ttatgggtcc ttgccacaag aacacatcat acaaaaaatc    2940
aaagaatgtt ttagaaaact tcctattaac aggcctattg attggaaagt atgtcaacga    3000
attgtgggtc ttttgggttt tgctgccct tttacacaat gtggttatcc tgcgttgatg    3060
cctttgtatg catgtattca atctaagcag gctttcactt tctcgccaac ttacaaggcc    3120
tttctgtgta acaatacct gaacctttac cccgttgccc ggcaacggcc aggtctgtgc    3180
caagtgtttg ctgacgcaac ccccactggc tggggcttgg tcatgggcca tcagcgcatg    3240
cgtggaacct tttcggctcc tctgccgatc catactgcgg aactcctagc cgcttgtttt    3300
gctcgcagca ggtctggagc aaacattatc gggactgata actctgttgt cctatcccgc    3360
aaatatacat cgtttccatg gctgctaggc tgtgctgcca actggatcct gcgcgggacg    3420
tcctttgttt acgtcccgtc ggcgctgaat cctgcggacg acccttctcg gggtcgcttg    3480
ggactctctc gtccccttct ccgtctgccg ttccgaccga ccacgggcg cacctctctt    3540
tacgcggact ccccgtctgt gccttctcat ctgccggacc gtgtgcactt cgcttcacct    3600
```

-continued

```
ctgcacgtcg catggagacc accgtgaacg cccaccaaat attgcccaag gtcttacata    3660
agaggactct tggactctca gcaatgtcaa cgaccgacct tgaggcatac ttcaaagact    3720
gtttgtttaa agactgggag gagttggggg aggagattag gttaaaggtc tttgtactag    3780
gaggctgtag gcataaattg gtctgcgcac cagcaccatg caacttttc acctctgcct     3840
aatcatctct tgttcatgtc ctactgttca agcctccaag ctgtgccttg ggtggctttg    3900
gggcatggac atcgacccct ataaagaatt tggagctact gtggagttac tctcgttttt    3960
gccttctgac ttctttcctt cagtacgaga tccactagtt ctagagcggc cgccaccgcg    4020
gtggagctcc agcttttgtt ccctttagtg agggttaatt gcgcgcatgc ccgacggcga    4080
ggatctcgtc gtgacccatg gcgatgcctg cttgccgaat atcatggtgg aaaatggccg    4140
cttttctgga ttcatcgact gtggccggct gggtgtggcg gaccgctatc aggacatagc    4200
gttggctacc cgtgatattg ctgaagagct tggcggcgaa tgggctgacc gcttcctcgt    4260
gctttacggt atcgccgctc ccgattcgca gcgcatcgcc ttctatcgcc ttcttgacga    4320
gttcttctga gcgggactct ggggttcgaa atgaccgacc aagcgacgcc caacctgcca    4380
tcacgagatt tcgattccac cgccgccttc tatgaaaggt tgggcttcgg aatcgttttc    4440
cgggacgccg gctggatgat cctccagcgc ggggatctca tgctggagtt cttcgcccac    4500
cccaacttgt ttattgcagc ttataatggt tacaaataaa gcaatagcat cacaaatttc    4560
acaaataaag catttttttc actgcattct agttgtggtt tgtccaaact catcaatgta    4620
tcttatcatg tctgtatacc gtcgacctct agctagagct tggcgtaatc atggtcatag    4680
ctgtttcctg tgtgaaattg ttatccgctc acaattccac acaacatacg agccggaagc    4740
ataaagtgta aagcctgggg tgcctaatga gtgagctaac tcacattaat tgcgttgcgc    4800
tcactgcccg ctttccagtc gggaaacctg tcgtgccagc tgcattaatg aatcggccaa    4860
cgcgcgggga gaggcggttt gcgtattggg cgctcttccg cttcctcgct cactgactcg    4920
ctgcgctcgg tcgttcggct gcggcgagcg gtatcagctc actcaaaggc ggtaatacgg    4980
ttatccacag aatcagggga taacgcagga aagaacatgt gagcaaaagg ccagcaaaag    5040
gccaggaacc gtaaaaaggc cgcgttgctg gcgtttttcc ataggctccg cccccctgac    5100
gagcatcaca aaaatcgacg ctcaagtcag aggtggcgaa acccgacagg actataaaga    5160
taccaggcgt ttccccctgg aagctccctc gtgcgctctc ctgttccgac cctgccgctt    5220
accggatacc tgtccgcctt tctcccttcg ggaagcgtgg cgctttctca atgctcacgc    5280
tgtaggtatc tcagttcggt gtaggtcgtt cgctccaagc tgggctgtgt gcacgaaccc    5340
cccgttcagc ccgaccgctg cgccttatcc ggtaactatc gtcttgagtc caacccggta    5400
agacacgact tatcgccact ggcagcagcc actggtaaca ggattagcag agcgaggtat    5460
gtaggcggtg ctacagagtt cttgaagtgg tggcctaact acggctacac tagaaggaca    5520
gtatttggta tctgcgctct gctgaagcca gttaccttcg gaaaaagagt tggtagctct    5580
tgatccggca aacaaaccac cgctggtagc ggtggttttt ttgtttgcaa gcagcagatt    5640
acgcgcagaa aaaaggatc tcaagaagat cctttgatct tttctacggg gtctgacgct    5700
cagtggaacg aaaactcacg ttaagggatt ttggtcatga gattatcaaa aaggatcttc    5760
acctagatcc ttttaaatta aaaatgaagt tttaaatcaa tctaaagtat atatgagtaa    5820
acttggtctg acagttacca atgcttaatc agtgaggcac ctatctcagc gatctgtcta    5880
tttcgttcat ccatagttgc ctgactcccc gtcgtgtaga taactacgat acgggagggc    5940
ttaccatctg gccccagtgc tgcaatgata ccgcgagacc cacgctcacc ggctccagat    6000
```

```
ttatcagcaa taaaccagcc agccggaagg gccgagcgca gaagtggtcc tgcaacttta   6060
tccgcctcca tccagtctat taattgttgc cgggaagcta gagtaagtag ttcgccagtt   6120
aatagtttgc gcaacgttgt tgccattgct acaggcatcg tggtgtcacg ctcgtcgttt   6180
ggtatggctt cattcagctc cggttcccaa cgatcaaggc gagttacatg atcccccatg   6240
ttgtgcaaaa aagcggttag ctccttcggt cctccgatcg ttgtcagaag taagttggcc   6300
gcagtgttat cactcatggt tatggcagca ctgcataatt ctcttactgt catgccatcc   6360
gtaagatgct tttctgtgac tggtgagtac tcaaccaagt cattctgaga atagtgtatg   6420
cggcgaccga gttgctcttg cccggcgtca atacgggata ataccgcgcc acatagcaga   6480
actttaaaag tgctcatcat tggaaaacgt tcttcggggc gaaaactctc aaggatctta   6540
ccgctgttga gatccagttc gatgtaaccc actcgtgcac ccaactgatc ttcagcatct   6600
tttactttca ccagcgtttc tgggtgagca aaaacaggaa ggcaaaatgc cgcaaaaaag   6660
ggaataaggg cgacacggaa atgttgaata ctcatactct tcctttttca atattattga   6720
agcatttatc agggttattg tctcatgagc ggatacatat ttgaatgtat ttagaaaaat   6780
aaacaaatag gggttccgcg cacatttccc cgaaaagtgc cacctgacgt c            6831
```

<210> SEQ ID NO 5
<211> LENGTH: 180
<212> TYPE: DNA
<213> ORGANISM: artificial sequence
<220> FEATURE:
<223> OTHER INFORMATION: Polyepitope sequence from prHBV-1.3-III

<400> SEQUENCE: 5

```
gactacaagg acgacgacga caagagcctg ttcaacaccg tggccaccct gtacaccaag     60
ggcatcctgg gcttcgtgtt caccctgaag aacgccggcc tgtgcaccct ggtggccatg    120
ctgggccccg gccccggcaa ggccaagttc gtggccgcct ggaccctgaa ggctgcagcc    180
```

<210> SEQ ID NO 6
<211> LENGTH: 79
<212> TYPE: PRT
<213> ORGANISM: artificial sequence
<220> FEATURE:
<223> OTHER INFORMATION: Sequence for rHBe-III

<400> SEQUENCE: 6

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Ser Phe Glu His Gly
            20                  25                  30

Ala Pro Ile Leu Ser Thr Leu Pro Glu Thr Thr Val Val Arg Arg Arg
        35                  40                  45

Gly Arg Ser Pro Arg Arg Arg Thr Pro Ser Pro Arg Arg Arg Arg Ser
    50                  55                  60

Gln Ser Pro Arg Arg Arg Arg Ser Gln Ser Arg Glu Ser Gln Cys
65                  70                  75
```

<210> SEQ ID NO 7
<211> LENGTH: 60
<212> TYPE: PRT
<213> ORGANISM: artificial sequence
<220> FEATURE:
<223> OTHER INFORMATION: Polyepitope sequence from rHBe-III

<400> SEQUENCE: 7

Asp Tyr Lys Asp Asp Asp Lys Ser Leu Phe Asn Thr Val Ala Thr
1               5                   10                  15

Leu Tyr Thr Lys Gly Ile Leu Gly Phe Val Phe Thr Leu Lys Asn Ala
            20                  25                  30

Gly Leu Cys Thr Leu Val Ala Met Leu Gly Pro Gly Pro Gly Lys Ala
        35                  40                  45

Lys Phe Val Ala Ala Trp Thr Leu Lys Ala Ala Ala
    50                  55                  60

<210> SEQ ID NO 8
<211> LENGTH: 60
<212> TYPE: PRT
<213> ORGANISM: artificial sequence
<220> FEATURE:
<223> OTHER INFORMATION: Sequence for polyepitope III

<400> SEQUENCE: 8

Asp Tyr Lys Asp Asp Asp Lys Ser Leu Phe Asn Thr Val Ala Thr
1               5                   10                  15

Leu Tyr Thr Lys Gly Ile Leu Gly Phe Val Phe Thr Leu Lys Asn Ala
            20                  25                  30

Gly Leu Cys Thr Leu Val Ala Met Leu Gly Pro Gly Pro Gly Lys Ala
        35                  40                  45

Lys Phe Val Ala Ala Trp Thr Leu Lys Ala Ala Ala
    50                  55                  60

<210> SEQ ID NO 9
<211> LENGTH: 63
<212> TYPE: PRT
<213> ORGANISM: artificial sequence
<220> FEATURE:
<223> OTHER INFORMATION: Sequence for polyepitope IV

<400> SEQUENCE: 9

Asp Tyr Lys Asp Asp Asp Lys Glu Leu Arg Ser Leu Tyr Asn Thr
1               5                   10                  15

Val Ala Thr Leu Tyr Thr Lys Gly Ile Leu Gly Phe Val Phe Thr Leu
            20                  25                  30

Lys Asn Ala Gly Leu Cys Thr Leu Val Ala Met Leu Gly Pro Gly Pro
        35                  40                  45

Gly Lys Ala Lys Phe Val Ala Ala Trp Thr Leu Lys Ala Ala Ala
    50                  55                  60

<210> SEQ ID NO 10
<211> LENGTH: 6831
<212> TYPE: DNA
<213> ORGANISM: artificial sequence
<220> FEATURE:
<223> OTHER INFORMATION: Sequence for prHBV-1.3-IV

<400> SEQUENCE: 10
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgca atctaagcag gctttcactt tctcgccaac    240
ttacaaggcc tttctgtgta acaataccct gaacctttac ccgttgccc ggcaacggcc    300 aggtctgtgc caagtgtttg ctgacgcaac ccccactggc tggggcttgg tcatgggcca    360

```
tcagcgcatg cgtggaacct tttcggctcc tctgccgatc catactgcgg aactcctagc    420
cgcttgtttt gctcgcagca ggtctggagc aaacattatc gggactgata actctgttgt    480
cctatcccgc aaatatacat cgtttccatg gctgctaggc tgtgctgcca actggatcct    540
gcgcgggacg tcctttgttt acgtcccgtc ggcgctgaat cctgcggacg acccttctcg    600
gggtcgcttg ggactctctc gtccccttct ccgtctgccg ttccgaccga ccacggggcg    660
cacctctctt tacgcggact ccccgtctgt gccttctcat ctgccggacc gtgtgcactt    720
cgcttcacct ctgcacgtcg catggagacc accgtgaacg cccaccaaat attgcccaag    780
gtcttacata agaggactct tggactctca gcaatgtcaa cgaccgacct tgaggcatac    840
ttcaaagact gtttgtttaa agactgggag gagttggggg aggagattag gttaaaggtc    900
tttgtactag gaggctgtag gcataaattg gtctgcgcac cagcaccatg caacttttc    960 acctctgcct aatcatctct tgttcatgtc ctactgttca agcctccaag ctgtgccttg   1020
ggtggctttg ggcatggac atcgacccct ataagaatt tggagctact gtggagttac   1080
tctcgttttt gccttctgac ttctttcctt cagtaagctt cgaacatgga gccctatcc    1140 tatcaacact tccggagact actgttgtta gacgacgagg caggtcccct agaagaagaa   1200
ctccctcgcc tcgcagacga aggtctcaat cgccgcgtcg cagaagatct caatctcggg   1260
aatctcaatg ttagtattcc ttggactcat aaggtgggga actttactgg gctttattct   1320
tctactgtac ctgtctttaa tcctcattgg aaaacaccat cttttcctaa tatacattta   1380
caccaagaca ttatcaaaaa atgtgaacag tttgtaggcc cactcacagt taatgagaaa   1440
agaagattgc aattgattat gcctgccagg ttttatccaa aggttaccaa atatttacca   1500
ttggataagg gtattaaacc ttattatcca gaacatctag ttaatcatta cttccaaact   1560
agacactatt tacacactct atggaaggcg ggtatattat ataagagaga acaacacat    1620 agcgcctcat tttgtgggtc accatattct tgggaacaag atctacagca tggggcagaa   1680
tctttccacc agcaatcctc tgggattctt tcccgaccac cagttggatc cagccttcag   1740
agcaaacacc gcaaatccag attgggactt caatcccaac aaggacacct ggccagacgc   1800
caacaaggta ggagctggag cattcgggct gggtttcacc ccaccgcacg gaggccttt    1860 ggggtggagc cctcaggctc agggcatact acaaactttg ccagcaaatc cgcctcctgc   1920
ctccaccaat cgccagtcag gaaggcagcc taccccgctg tctccacctt tgagaaacac   1980
tcatcctcag gccatgcagt ggaattccac aaccttccac caaactctgc aagatcccag   2040
agtgagaggc ctgtatttcc ctgctggtgg ctccagttca ggaacagtaa accctgttct   2100
gactactgcc tctcccttat cgtcaatctt ctcgaggatt ggggaccctg cgctgaacat   2160
ggagaacatc acatcaggat tcctaggacc ccttctcgtg ttacaggcgg ggttttct    2220 gttgacaaga atcctcacaa taccgcagag tctagactcg tggtggactt ctctcaattt   2280 tctagggga actaccgtgt gtcttggcca aaattcgcag tccccaacct ccaatcactc    2340
accaacctct tgtcctccaa cttgtcctgg ttatcgctgg atgtgtctgc ggcgttttat   2400
catcttcctc ttcatcctgc tgctatgcct catcttcttg ttggttcttc tggactatca   2460
aggtatgttg cccgtttgtc ctctaattcc aggatcctca acaaccagca cgggaccatg   2520
ccggacctgc atgactactg ctcaaggaac ctctatgtat ccctcctgtt gctgtaccaa   2580
accttcggac ggaaattgca cctgtattcc catcccatca tcctgggctt tcggaaaatt   2640
cctatgggag tgggcctcag cccgtttctc ctggctcagt ttactagtgc catttgttca   2700
gtggttcgta gggctttccc ccactgtttg gctttcagtt atatggatga tgtggtattg   2760
```

```
ggggccaagt ctgtacagca tcttgagtcc cttttttaccg ctgttaccaa tttttcttttg      2820
tctttgggta tacatttaaa ccctaacaaa acaaagagat ggggttactc tctaaatttt      2880
atgggttatg tcattggatg ttatgggtcc ttgccacaag aacacatcat acaaaaaatc      2940
aaagaatgtt ttagaaaact tcctattaac aggcctattg attggaaagt atgtcaacga      3000
attgtgggtc ttttgggttt tgctgcccct tttacacaat gtggttatcc tgcgttgatg      3060
cctttgtatg catgtattca atctaagcag gctttcactt tctcgccaac ttacaaggcc      3120
tttctgtgta acaataccct gaacctttac cccgttgccc ggcaacggcc aggtctgtgc      3180
caagtgtttg ctgacgcaac ccccactggc tggggcttgg tcatgggcca tcagcgcatg      3240
cgtggaacct tttcggctcc tctgccgatc catactgcgg aactcctagc cgcttgtttt      3300
gctcgcagca ggtctggagc aaacattatc gggactgata actctgttgt cctatcccgc      3360
aaatatacat cgtttccatg gctgctaggc tgtgctgcca actggatcct gcgcgggacg      3420
tcctttgttt acgtcccgtc ggcgctgaat cctgcggacg accttctcg gggtcgcttg      3480
ggactctctc gtcccttct ccgtctgccg ttccgaccga ccacggggcg cacctctctt      3540
tacgcggact ccccgtctgt gccttctcat ctgccggacc gtgtgcactt cgcttcacct      3600
ctgcacgtcg catggagacc accgtgaacg cccaccaaat attgcccaag gtcttacata      3660
agaggactct tggactctca gcaatgtcaa cgaccgacct tgaggcatac ttcaaagact      3720
gtttgtttaa agactgggag gagttggggg aggagattag gttaaaggtc tttgtactag      3780
gaggctgtag gcataaattg gtctgcgcac cagcaccatg caacttttc acctctgcct      3840
aatcatctct tgttcatgtc ctactgttca agcctccaag ctgtgccttg ggtggctttg      3900
gggcatggac atcgacccctt ataaagaatt tggagctact gtggagttac tctcgttttt      3960
gccttctgac ttctttcctt cagtacgaga tccactagtt ctagagcggc cgccaccgcg      4020
gtggagctcc agcttttgtt cccttttagtg agggttaatt gcgcgcatgc ccgacggcga      4080
ggatctcgtc gtgacccatg gcgatgcctg cttgccgaat atcatggtgg aaaatggccg      4140
cttttctgga ttcatcgact gtggccggct gggtgtggcg gaccgctatc aggacatagc      4200
gttggctacc cgtgatattg ctgaagagct tggcggcgaa tgggctgacc gcttcctcgt      4260
gctttacggt atcgccgctc ccgattcgca gcgcatcgcc ttctatcgcc ttcttgacga      4320
gttcttctga gcgggactct ggggttcgaa atgaccgacc aagcgacgcc caacctgcca      4380
tcacgagatt tcgattccac cgccgccttc tatgaaaggt tgggcttcgg aatcgttttc      4440
cgggacgccg gctggatgat cctccagcgc ggggatctca tgctggagtt cttcgcccac      4500
cccaacttgt ttattgcagc ttataatggt tacaaataaa gcaatagcat cacaaatttc      4560
acaaataaag catttttttc actgcattct agttgtggtt tgtccaaact catcaatgta      4620
tcttatcatg tctgtatacc gtcgacctct agctagagct tggcgtaatc atggtcatag      4680
ctgtttcctg tgtgaaattg ttatccgctc acaattccac acaacatacg agccggaagc      4740
ataaagtgta aagcctgggg tgcctaatga gtgagctaac tcacattaat tgcgttgcgc      4800
tcactgcccg ctttccagtc gggaaacctg tcgtgccagc tgcattaatg aatcggccaa      4860
cgcgcgggga gaggcggttt gcgtattggg cgctcttccg cttcctcgct cactgactcg      4920
ctgcgctcgg tcgttcggct gcggcgagcg gtatcagctc actcaaaggc ggtaatacgg      4980
ttatccacag aatcagggga taacgcagga aagaacatgt gagcaaaagg ccagcaaaag      5040
gccaggaacc gtaaaaaggc cgcgttgctg gcgtttttcc ataggctccg ccccccctgac      5100
```

```
gagcatcaca aaaatcgacg ctcaagtcag aggtggcgaa acccgacagg actataaaga      5160
taccaggcgt ttccccctgg aagctccctc gtgcgctctc ctgttccgac cctgccgctt      5220
accggatacc tgtccgcctt tctcccttcg ggaagcgtgg cgctttctca atgctcacgc      5280
tgtaggtatc tcagttcggt gtaggtcgtt cgctccaagc tgggctgtgt gcacgaaccc      5340
cccgttcagc ccgaccgctg cgccttatcc ggtaactatc gtcttgagtc caacccggta      5400
agacacgact tatcgccact ggcagcagcc actggtaaca ggattagcag agcgaggtat      5460
gtaggcggtg ctacagagtt cttgaagtgg tggcctaact acggctacac tagaaggaca      5520
gtatttggta tctgcgctct gctgaagcca gttaccttcg aaaaagagt tggtagctct       5580 tgatccggca aacaaaccac cgctggtagc ggtggttttt ttgtttgcaa gcagcagatt      5640
acgcgcagaa aaaaggatc tcaagaagat cctttgatct tttctacggg gtctgacgct       5700
cagtggaacg aaaactcacg ttaagggatt ttggtcatga gattatcaaa aaggatcttc      5760
acctagatcc ttttaaatta aaaatgaagt tttaaatcaa tctaaagtat atatgagtaa      5820
acttggtctg acagttacca atgcttaatc agtgaggcac ctatctcagc gatctgtcta      5880
tttcgttcat ccatagttgc ctgactcccc gtcgtgtaga taactacgat acgggagggc      5940
ttaccatctg gccccagtgc tgcaatgata ccgcgagacc cacgctcacc ggctccagat      6000
ttatcagcaa taaaccagcc agccggaagg gccgagcgca gaagtggtcc tgcaacttta      6060
tccgcctcca tccagtctat taattgttgc cgggaagcta gagtaagtag ttcgccagtt      6120
aatagtttgc gcaacgttgt tgccattgct acaggcatcg tggtgtcacg ctcgtcgttt      6180
ggtatggctt cattcagctc cggttcccaa cgatcaaggc gagttacatg atcccccatg      6240
ttgtgcaaaa aagcggttag ctccttcggt cctccgatcg ttgtcagaag taagttggcc      6300
gcagtgttat cactcatggt tatggcagca ctgcataatt ctcttactgt catgccatcc      6360
gtaagatgct tttctgtgac tggtgagtac tcaaccaagt cattctgaga atagtgtatg      6420
cggcgaccga gttgctcttg cccggcgtca tacggggata ataccgcgcc acatagcaga      6480
actttaaaag tgctcatcat tggaaaacgt tcttcggggc gaaaactctc aaggatctta      6540
ccgctgttga tccagttcga tgtaaccac actcgtgcac ccaactgatc ttcagcatct      6600
tttactttca ccagcgtttc tgggtgagca aaaacaggaa ggcaaaatgc cgcaaaaaag      6660
ggaataaggg cgacacggaa atgttgaata ctcatactct tccttttca atattattga       6720 agcatttatc agggttattg tctcatgagc ggatacatat ttgaatgtat ttagaaaaat      6780
aaacaaatag gggttccgcg cacatttccc cgaaaagtgc cacctgacgt c                6831
```

```
<210> SEQ ID NO 11
<211> LENGTH: 189
<212> TYPE: DNA
<213> ORGANISM: artificial sequence
<220> FEATURE:
<223> OTHER INFORMATION: Polyepitope sequence from prHBV-1.3-IV

<400> SEQUENCE: 11
gactacaagg acgacgacga caaggaacta agaagcctgt acaacaccgt ggccaccctg        60
tacaccaagg gcatcctggg cttcgtgttc accctgaaga cgccggcct gtgcaccctg        120 gtggccatgc tgggccccgg ccccggcaag gccaagttcg tggccgcctg gaccctgaag       180
gctgcagcc                                                              189

<210> SEQ ID NO 12
<211> LENGTH: 142
```

-continued

<212> TYPE: PRT
<213> ORGANISM: artificial sequence
<220> FEATURE:
<223> OTHER INFORMATION: Sequence for rHBe-IV

<400> SEQUENCE: 12

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Ser Phe Asp Tyr Lys
20 25 30

Asp Asp Asp Asp Lys Glu Leu Arg Ser Leu Tyr Asn Thr Val Ala Thr
35 40 45

Leu Tyr Thr Lys Gly Ile Leu Gly Phe Val Phe Thr Leu Lys Asn Ala
50 55 60

Gly Leu Cys Thr Leu Val Ala Met Leu Gly Pro Gly Pro Gly Lys Ala
65 70 75 80

Lys Phe Val Ala Ala Trp Thr Leu Lys Ala Ala Ala Glu His Gly Ala
85 90 95

Pro Ile Leu Ser Thr Leu Pro Glu Thr Thr Val Val Arg Arg Arg Gly
100 105 110

Arg Ser Pro Arg Arg Arg Thr Pro Ser Pro Arg Arg Arg Arg Ser Gln
115 120 125

Ser Pro Arg Arg Arg Arg Ser Gln Ser Arg Glu Ser Gln Cys
130 135 140

<210> SEQ ID NO 13
<211> LENGTH: 63
<212> TYPE: PRT
<213> ORGANISM: artificial sequence
<220> FEATURE:
<223> OTHER INFORMATION: Polyetpitopn sequence from rHBe-IV

<400> SEQUENCE: 13

Asp Tyr Lys Asp Asp Asp Asp Lys Glu Leu Arg Ser Leu Tyr Asn Thr
1 5 10 15

Val Ala Thr Leu Tyr Thr Lys Gly Ile Leu Gly Phe Val Phe Thr Leu
20 25 30

Lys Asn Ala Gly Leu Cys Thr Leu Val Ala Met Leu Gly Pro Gly Pro
35 40 45

Gly Lys Ala Lys Phe Val Ala Ala Trp Thr Leu Lys Ala Ala Ala
50 55 60

<210> SEQ ID NO 14
<211> LENGTH: 3182
<212> TYPE: DNA
<213> ORGANISM: artificial sequence
<220> FEATURE:
<223> OTHER INFORMATION: Hepatitis B (virus strain) ayw genome
(Accession number V01460 )

<400> SEQUENCE: 14
aattccactg catggcctga ggatgagtgt ttctcaaagg tggagacagc ggggtaggct 60
gccttcctga ctggcgattg gtggaggcag gaggcggatt tgctggcaaa gtttgtagta 120
tgccctgagc ctgagggctc caccccaaaa ggcctccgtg cggtggggtg aaacccagcc 180
cgaatgctcc agctcctacc ttgttggcgt ctggccaggt gtccttgttg ggattgaagt 240
cccaatctgg atttgcggtg tttgctctga aggctggatc caactggtgg tcgggaaaga 300
atcccagagg attgctggtg gaaagattct gccccatgct gtagatcttg ttcccaagaa 360

```
tatggtgacc cacaaaatga ggcgctatgt gttgtttctc tcttatataa tatacccgcc    420
ttccatagag tgtgtaaata gtgtctagtt tggaagtaat gattaactag atgttctgga    480
taataaggtt taatacccct atccaatggt aaatatttgg taacctttgg ataaaacctg    540
gcaggcataa tcaattgcaa tcttcttttc tcattaactg tgagtgggcc tacaaactgt    600
tcacattttt tgataatgtc ttggtgtaaa tgtatattag gaaaagatgg tgttttccaa    660
tgaggattaa agacaggtac agtagaagaa taaagcccag taaagttccc caccttatga    720
gtccaaggaa tactaacatt gagattcccg agattgagat cttctgcgac gcggcgattg    780
agaccttcgt ctgcgaggcg agggagttct tcttctaggg gacctgcctc gtcgtctaac    840
aacagtagtc tccggaagtg ttgataggat aggggcattt ggtggtctat aagctggagg    900
agtgcgaatc cacactccga aagacaccaa atactctata actgtttctc ttccaaaagt    960
gagacaagaa atgtgaaacc acaagagttg cctgaacttt aggcccatat tagtgttgac   1020
ataactgact actaggtctc tagacgctgg atcttccaaa ttaacaccca cccaggtagc   1080
tagagtcatt agttcccccc agcaaagaat tgcttgcctg agtgcagtat ggtgaggtga   1140
acaatgctca ggagactcta aggcttcccg atacagagct gaggcggtat ctagaagatc   1200
tcgtactgaa ggaaagaagt cagaaggcaa aaacgagagt aactccacag tagctccaaa   1260
ttctttataa gggtcgatgt ccatgcccca agccaccca aggcacagct tggaggcttg    1320
aacagtagga catgaacaag agatgattag gcagaggtga aaaagttgca tggtgctggt   1380
gcgcagacca atttatgcct acagcctcct agtacaaaga cctttaacct aatctcctcc   1440
cccaactcct cccagtcttt aaacaaacag tctttgaagt atgcctcaag gtcggtcgtt   1500
gacattgctg agagtccaag agtcctctta tgtaagacct tgggcaatat ttggtgggcg   1560
ttcacggtgg tctccatgcg acgtgcagag gtgaagcgaa gtgcacacgg tccggcagat   1620
gagaaggcac agacggggag tccgcgtaaa gagaggtgcg ccccgtggtc ggtcggaacg   1680
gcagacggag aaggggacga gagagtccca agcgaccccg agaagggtcg tccgcaggat   1740
tcagcgccga cgggacgtaa acaaaggacg tcccgcgcag gatccagttg gcagcacagc   1800
ctagcagcca tggaaacgat gtatatttgc gggataggac aacagagtta tcagtcccga   1860
taatgtttgc tccagacctg ctgcgagcaa aacaagcggc taggagttcc gcagtatgga   1920
tcggcagagc agccgaaaag gttccacgca tgcgctgatg gcccatgacc aagccccagc   1980 cagtggggt tgcgtcagca aacacttggc acagacctgg ccgttgccgg gcaacggggt    2040
aaaggttcag gtattgttta cacagaaagg ccttgtaagt tggcgagaaa gtgaaagcct   2100
gcttagattg aatacatgca tacaaaggca tcaacgcagg ataaccacat tgtgtaaaag   2160
gggcagcaaa acccaaaaga cccacaattc gttgacatac tttccaatca ataggcctgt   2220
taataggaag ttttctaaaa cattctttga ttttttgtat gatgtgttct tgtggcaagg   2280
acccataaca tccaatgaca taacccataa aatttagaga gtaacccat ctctttgttt    2340 tgttagggtt taaatgtata cccaaagaca aaagaaaatt ggtaacagcg gtaaaaaggg   2400
actcaagatg ctgtacagac ttggcccca ataccacatc atccatataa ctgaaagcca    2460
aacagtgggg gaaagccta cgaaccactg aacaaatggc actagtaaac tgagccagga    2520
gaaacgggct gaggcccact cccataggaa ttttccgaaa gcccaggatg atgggatggg   2580
aatacaggtg caatttccgt ccgaaggttt ggtacagcaa caggagggat acatagaggt   2640
tccttgagca gtagtcatgc aggtccggca tggtcccgtg ctggttgttg aggatcctgg   2700
aattagagga caaacgggca acataccttg atagtccaga agaaccaaca agaagatgag   2760
```

-continued

```
gcatagcagc aggatgaaga ggaagatgat aaaacgccgc agacacatcc agcgataacc    2820
aggacaagtt ggaggacaag aggttggtga gtgattggag gttggggact gcgaattttg    2880
gccaagacac acggtagttc cccctagaaa attgagagaa gtccaccacg agtctagact    2940
ctgcggtatt gtgaggattc ttgtcaacaa gaaaaacccc gcctgtaaca cgagaagggg    3000
tcctaggaat cctgatgtga tgttctccat gttcagcgca gggtcccca  tcctcgagaa    3060 gattgacgat aagggagagg cagtagtcag aacagggttt actgttcctg aactggagcc    3120
accagcaggg aaatacaggc ctctcactct gggatcttgc agagtttggt ggaaggttgt    3180
gg                                                                   3182
```

<210> SEQ ID NO 15
<211> LENGTH: 9
<212> TYPE: PRT
<213> ORGANISM: artificial sequence
<220> FEATURE:
<223> OTHER INFORMATION: HIV-1 epitope from gag protein p17

<400> SEQUENCE: 15

Ser Leu Tyr Asn Thr Val Ala Thr Leu
1               5

<210> SEQ ID NO 16
<211> LENGTH: 8
<212> TYPE: PRT
<213> ORGANISM: artificial sequence
<220> FEATURE:
<223> OTHER INFORMATION: HIV-1 epitope from gag protein p24

<400> SEQUENCE: 16

Thr Leu Asn Ala Trp Val Lys Trp
1               5

<210> SEQ ID NO 17
<211> LENGTH: 10
<212> TYPE: PRT
<213> ORGANISM: artificial sequence
<220> FEATURE:
<223> OTHER INFORMATION: HIV-1 epitope from pol protein

<400> SEQUENCE: 17

Leu Leu Asp Thr Gly Ala Asp Asp Thr Val
1               5                   10

<210> SEQ ID NO 18
<211> LENGTH: 11
<212> TYPE: PRT
<213> ORGANISM: artificial sequence
<220> FEATURE:
<223> OTHER INFORMATION: HIV-1 epitope from pol protein

<400> SEQUENCE: 18

Val Leu Asp Val Gly Asp Ala Tyr Phe Ser Val
1               5                   10

<210> SEQ ID NO 19
<211> LENGTH: 9
<212> TYPE: PRT
<213> ORGANISM: artificial sequence
<220> FEATURE:
<223> OTHER INFORMATION: HIV-1 epitope from pol protein

<400> SEQUENCE: 19

```
Val Ile Tyr Gln Tyr Met Asp Asp Leu
1               5

<210> SEQ ID NO 20
<211> LENGTH: 9
<212> TYPE: PRT
<213> ORGANISM: artificial sequence
<220> FEATURE:
<223> OTHER INFORMATION: HIV-1 epitope from pol protein

<400> SEQUENCE: 20

Ile Leu Lys Glu Pro Val His Gly Val
1               5

<210> SEQ ID NO 21
<211> LENGTH: 9
<212> TYPE: PRT
<213> ORGANISM: artificial sequence
<220> FEATURE:
<223> OTHER INFORMATION: HIV-1 epitope from pol protein

<400> SEQUENCE: 21

Pro Leu Val Lys Leu Trp Tyr Gln Leu
1               5

<210> SEQ ID NO 22
<211> LENGTH: 11
<212> TYPE: PRT
<213> ORGANISM: artificial sequence
<220> FEATURE:
<223> OTHER INFORMATION: HIV-1 epitope from pol protein

<400> SEQUENCE: 22

Glu Ser Glu Leu Val Asn Gln Ile Ile Glu Gln
1               5                   10

<210> SEQ ID NO 23
<211> LENGTH: 10
<212> TYPE: PRT
<213> ORGANISM: artificial sequence
<220> FEATURE:
<223> OTHER INFORMATION: HIV-1 epitope from pol protein

<400> SEQUENCE: 23

Glu Leu Val Asn Gln Ile Ile Glu Gln Leu
1               5                   10

<210> SEQ ID NO 24
<211> LENGTH: 9
<212> TYPE: PRT
<213> ORGANISM: artificial sequence
<220> FEATURE:
<223> OTHER INFORMATION: HIV-1 epitope from pol protein

<400> SEQUENCE: 24

Leu Leu Trp Lys Gly Glu Gly Ala Val
1               5

<210> SEQ ID NO 25
<211> LENGTH: 9
<212> TYPE: PRT
<213> ORGANISM: artificial sequence
<220> FEATURE:
<223> OTHER INFORMATION: HIV-1 epitope from env protein

<400> SEQUENCE: 25

Arg Leu Arg Asp Leu Leu Leu Ile Val
```

```
<210> SEQ ID NO 26
<211> LENGTH: 9
<212> TYPE: PRT
<213> ORGANISM: artificial sequence
<220> FEATURE:
<223> OTHER INFORMATION: HIV-1 epitope from nef protein

<400> SEQUENCE: 26

Ala Phe His His Val Ala Arg Glu Leu
1               5
```